(12) United States Patent
Jelinek et al.

(10) Patent No.: US 12,049,622 B2
(45) Date of Patent: *Jul. 30, 2024

(54) TARGETED TRANSPOSITION FOR USE IN EPIGENETIC STUDIES

(71) Applicant: Active Motif, Inc., Carlsbad, CA (US)

(72) Inventors: Mary Anne Jelinek, Carlsbad, CA (US); Brian Stanley Egan, Carlsbad, CA (US); Joseph Fernandez, Carlsbad, CA (US)

(73) Assignee: ACTIVE MOTIF, INC., Carlsbad, CA (US)

( * ) Notice: Subject to any disclaimer, the term of this patent is extended or adjusted under 35 U.S.C. 154(b) by 40 days.

This patent is subject to a terminal disclaimer.

(21) Appl. No.: 17/705,005

(22) Filed: Mar. 25, 2022

(65) Prior Publication Data
US 2022/0356465 A1 Nov. 10, 2022

Related U.S. Application Data

(63) Continuation of application No. 16/946,073, filed on Jun. 4, 2020, now Pat. No. 11,306,307, which is a continuation of application No. 14/892,911, filed as application No. PCT/US2014/039250 on May 22, 2014, now Pat. No. 10,689,643, and a continuation of application No. 14/359,877, filed as application No. PCT/US2012/066472 on Nov. 23, 2012, now Pat. No. 9,938,524.

(60) Provisional application No. 61/826,481, filed on May 22, 2013, provisional application No. 61/629,555, filed on Nov. 22, 2011.

(51) Int. Cl.
| | | |
|---|---|---|
| *C12N 15/10* | (2006.01) | |
| *C07H 21/00* | (2006.01) | |
| *C12Q 1/6804* | (2018.01) | |
| *C12Q 1/6806* | (2018.01) | |

(52) U.S. Cl.
CPC ......... *C12N 15/1068* (2013.01); *C07H 21/00* (2013.01); *C12N 15/1006* (2013.01); *C12N 15/1034* (2013.01); *C12N 15/1065* (2013.01); *C12N 15/1093* (2013.01); *C12Q 1/6804* (2013.01); *C12Q 1/6806* (2013.01)

(58) Field of Classification Search
CPC ............ C12N 15/1068; C12N 15/1065; C12N 15/1093; C12N 15/1006; C12Q 1/6806; C12Q 2522/101; C12Q 2531/113; C12Q 2535/122; C12Q 2537/159; C12Q 2563/131; C12Q 1/6804
See application file for complete search history.

(56) References Cited

U.S. PATENT DOCUMENTS

| | | |
|---|---|---|
| 6,228,647 B1 | 5/2001 | Voytas et al. |
| 6,846,622 B1 | 1/2005 | Heffron et al. |
| 7,790,379 B2 | 9/2010 | Laemmli et al. |
| 8,829,171 B2 | 9/2014 | Steemers et al. |
| 9,005,935 B2 | 4/2015 | Belyaev |
| 9,074,251 B2 | 7/2015 | Steemers et al. |
| 2002/0051986 A1 | 5/2002 | Baez et al. |
| 2003/0124537 A1 | 7/2003 | Liu et al. |
| 2005/0130161 A1 | 6/2005 | Fraser et al. |
| 2005/0272917 A1 | 12/2005 | Jiao et al. |
| 2006/0252140 A1 | 11/2006 | Yant et al. |
| 2007/0009937 A1 | 1/2007 | Laemmli et al. |
| 2007/0190601 A1 | 8/2007 | Harvey |
| 2008/0008687 A1* | 1/2008 | Ivics ............ A61P 19/04 435/6.12 |
| 2010/0240101 A1 | 9/2010 | Lieberman et al. |
| 2012/0258892 A1 | 10/2012 | Wang |
| 2013/0011833 A1 | 1/2013 | Quake et al. |
| 2016/0060691 A1 | 3/2016 | Giresi et al. |

FOREIGN PATENT DOCUMENTS

| | | | |
|---|---|---|---|
| WO | 2002008286 A2 | 1/2002 | |
| WO | 2004069994 A2 | 8/2004 | |
| WO | 2004094456 A2 | 11/2004 | |
| WO | 2012061832 A1 | 5/2012 | |
| WO | WO-2012061832 A1 * | 5/2012 | ......... C12N 15/1065 |
| WO | 2012080591 A1 | 6/2012 | |
| WO | 2013078470 A2 | 5/2013 | |
| WO | 2012106546 A3 | 11/2013 | |
| WO | 2014142850 A1 | 9/2014 | |
| WO | 2014189957 A2 | 11/2014 | |
| WO | 2017025594 A1 | 2/2017 | |

OTHER PUBLICATIONS

Ghosh, Anirban, and Manju Bansal. "A glossary of DNA structures from A to Z." Acta Crystallographica Section D: Biological Crystallography 59.4 (2003): 620-626. (Year: 2003).*

Zayed et al.("The DNA-bending protein HMGB1 is a cellular cofactor of Sleeping Beauty transposition." Nucleic acids research 31.9 (2003): 2313-2322) (Year: 2003).*

Zayed et al. ("Development of hyperactive sleeping beauty transposon vectors by mutational analysis." Molecular Therapy 9.2 (2004): 292-304.) (Year: 2004).*

Yandell, Decoding Bacterial Methylomes. The Scientist, May 1, 20135 (5 pages).

Yant S.R. et al., "Fusion Proteins Consisting of the Sleeping Beauty Transposase and the Polydactyl Zinc Finger Protein E2C Direct Transposon Integration into a Unique Human Chromosomal Sequence," Molecular Therapy, vol. 11, Supplement 1, May 2005.

(Continued)

*Primary Examiner* — Sahana S Kaup
(74) *Attorney, Agent, or Firm* — Storella, P.C.

(57) ABSTRACT

Disclosed herein are compositions, methods and kits useful for epigenetic analysis based on the use of transposons that are targeted to specific regions of chromatin based on DNA-DNA interactions, protein-protein interactions, RNA-RNA interactions, and nucleic acid-protein interactions.

48 Claims, 42 Drawing Sheets

Specification includes a Sequence Listing.

(56) References Cited

OTHER PUBLICATIONS

Zang et al., A clustering approach for identification of enriched domains from histone modification ChIP-Seq data. Bioinformatics. Aug. 1, 2009;25(15):1952-1958.
Zhang et al., Model-based Analysis of ChIP-Seq (MACS). Genome Biol. 2008;9(9): R137 (9 pages).
Active Motif, "Molecular Identifier (MID) Analysis for TAM-ChIP Paired-End Sequencing"Catalog Nos. 53126 and 53127, 7 pages.
Active Motif, I., ChIP-IT Express Magnetic Chromatin Immunoprecipitation Kit. 2011, Active Motif, Carlsbad, California, USA (32 pages).
Adams Eddie, Ph.D., "Declaration of Eddie Adams, Ph.D. Under 37 CFR 1.132", Dated Nov. 14, 2019, 71 pages.
Adey et al, "Rapid, low-input, low-bias construction of shotgun fragment libraries by high-density in vitro transposition," 2010, 17 pages, Genome Biology.
AKST, Epigenetics Armed German E.coli. The Scientist Nov. 2012: 3 pages.
Alberts et al., Activation of SRF-Regulated Chromosomal Templates by Rho-Family GTPases Requires a Signal that Also Induces H4 Hyperacetylation. Cell. Feb. 20, 1998;92(4):475-487.
Allis, et al., Overview and Concepts, in Epigenetics, Allis, et al., Eds. 2006, Cold Spring Harbor Laboratory Press: New York. p. 23-62.
Anonymous, ChIP-IT Express Magnetic Chromatin Inmunoprecipitation Kits (version D2) Catalog Nos. 53008 & 53009. Active Motif Product Catalog 2009,:FP-32, XP002755832, (35 pages). Retrieved from the Internet: URL:http://www.biotechniques.com/multimedia/archive/00054/chip-it express manu 54059a.pdf [retrieved on Mar. 21, 2016].
Becker, A. et al. "Direct Homo- and Hetero-Interactions of MeCP2 and MBD2," PLOS One, vol. 8, Issue 1, e53730, Jan. 2013.
Bertram et al., Integrative elements for Bacillus subtilis yielding tetracycline-dependent growth phenotypes. Nucleic Acids Res. Oct. 12, 2005;33(18):e153 (11 pages).
Boeva, Valentina, "Analysis of Genomic Sequence Motifs for Deciphering Transcription Factor Binding and Transcriptional egulation in Eukaryotic Cells", Frontiers in Genetics, Feb. 23, 2016, 15 pages.
Braunstein et al., Transcriptional silencing in yeast is associated with reduced nucleosome acetylation. Genes Dev. Apr. 1993;7(4):592-604.
Bruscella et al., The Use of Chromatin Immunoprecipitation to Define . . . J. Bacteriol. Oct. 2008.; 190(20):6817-6828 (12 pages).
Buenrostro, J. et al. "Transposition of native chromatin for fast and sensitive epigenomic profiling of open chromatin, DNDNA-binding proteins and nucleosome position." Nature America, Inc. 2013; Nature Methods; Advance Online Publicaiton pp. 1-8.
Cassandri M. et al. "Zinc-finger Proteins in Health and Disease," Cell Death Discovery 3, Article No. 17071, pp. 1-45 Nov. 2, 45017.
Chu et al. Genomic Maps of Long Noncoding RNA Occupancy . . . . Mol. Cell. Nov. 18, 2011;44(4):667-678 (2 pages).
Applicant response to Non-Final Office Action for U.S. Appl. No. 14/359,877 dated Jul. 27, 2017, 10 pages.
Dahl et al., "Q2ChIP, a Quick and Quantitative Chromatin Immunoprecipitation Assay, Unravels Epigenetic Dynamics of Developmentally Regulated Genes in Human Carcinoma Cells," Feb. 1, 2007, pp. 1037-1046, Stem Cells, Norway.
Davies et al., Three-Dimensional Structure of the Tn5 Synaptic Complex Transposition Intermediate. Science. Jul. 7, 2000;289(5476):77-85.
De Silva et al. ( "Virion-associated cofactor high-mobility group DNA-binding protein-1 facilitates transposition from the herpes simplex virus/Sleeping Beauty amplicon vector platform." Human gene therapy 21.11 (2010): 1615-1622; published online Oct. 7, 2010) (Year: 2010).
Demattei et al "Site-directed integration of transgenes: transposons revisited using DNA-binding-domain technologies" (Genetica, 2010, vol. 138, pp. 531-540).

Demattel M. V. et al. "Site-directed integration of transgenes: transposons revised using DNA-binding-domain technologies" Genetica, 2010, 138, p. 531-540.
Diagenode S.A. "In Response to the Summons dated May 31, 2021 and in preparation of the oral proceedings scheduled for Jan. 25, 2022", Prepared by Maiwald Intellectual Property, Nov. 25, 2021, 26 pages.
Dirksen and Dawson, Rapid Oxime and Hydrazone Ligations with Aromatic Aldehydes for Biomolecular Labeling. Bioconjug Chem. Dec. 2008; 19(12):2543-2548.
Dostie et al., Mapping networks of physical interactions between genomic elements using 5C technology. Nat Protoc. 2007;2(4):988-1002.
Epicentre, "Nextera Sample Prep Kit (Roche Titanium-compatible)", Cat. Nos. NT09115, NT091120, NT0911-50, NT0911-96, and NTBC0950, Madison, WI, 8 pages.
EPO Communication of a Notice of Opposition issued on Oct. 6, 2020 for EP Application 14801374.1.
EPO Communication under Rule 71(3)—Intention to Grant—issued in EP 12852118.4-1404, dated Jun. 7, 2017, 61 pages.
EPO Notification of Opposition filed by Diagenode S.A.dated Oct. 13, 2020 for EP Application 14801374.1.
Extended European Search Report dated Aug. 26, 2020 for EP Application No. 19217844.0 filed May 22, 2014.
Extended European Search Report issued in EP 12852118 dated Apr. 20, 2016.
Extended European Search Report issued in EP 2999784 dated Jan. 18, 2017 (11 pages).
Fang et al., Genome-wide mapping of methylated adenine residues . . . Nat Biotechnol. Dec. 2012;30(12):1232-1239 (8 pages).
Felsenfeld, G., A Brief History of Epigenetics, in Epigenetics, Allis, et al., Eds. 2005, p. 15-22.
Feng et al., Precise targeted integration by a chimaeric transposase zinc-finger fusion protein, Nucleic Acids Research, 2010, vol. 38, No. 4, pp. 1204-1216.
Finn et al., Synthesis and Properties of DNA-PNA Chimeric Oligomers, Nucleic Acids Res. Sep. 1, 1996:24(17) 3357-3363 (7 pages).
Fredriksson et al., Multiplexed Proximity Ligation Assays to Profile Putative Plasma Biomarkers Relevant to Pancreatic and Ovarian Cancer. Clin Chem. Mar. 2008;54(3):582-589.
Furey, ChIP-seq and beyond: new and improved methodologies to detect and characterize protein—DNA interactions. Nat Rev Genet. Dec. 2012; 13(12):840-852.
Gallagher et al., A comprehensive transposon mutant library of Francisella novicida, a bioweapon surrogate. Proc Natl Acad Sci U S A. Jan. 16, 2007;104(3):1009-1014.
Gangadharan et al, "DNA Transposon Hermes Inserts into DNA in Nucleosome-free Regions in Vivo," PNAS, Dec. 21, 2010, pp. 21966-21972, Department of a Molecular Biology and Genetics Division of Biostatistics and Bioinformatics, and Department of Oncology, The Johns Hopkins University School of Medicine, Baltimore, MD.
Giresi et al. (Methods 48.3 (2009): 233-239) (Year: 2009).
Goryshin and Reznikoff, Tn5 in Vitro Transposition. J Biol Chem. Mar. 27, 1998;273(13):7367-7374.
Goryshin et al., Insertional transposon mutagenesis by electroporation of released Tn5 transposition complexes. Nat Biotechnol. Jan. 2000; 18(1):97-100.
Goryshin et al., Tn5/IS50 target recognition. Proc Natl Acad Sci U S A. Sep. 1, 1998;95(18):10716-10721.
Grewal and Moazed, Heterochromatin and Epigenetic Control of Gene Expression. Science. Aug. 3, 2003;301 ;5634):798-802.
Grewal, RNAi-dependent formation of heterochromatin and its diverse functions. Curr Opin Genet Dev. Apr. 2010; 20 (2); 134-141 (8 pages).
Guttman and Rinn, Modular regulatory principles of large non-coding RNAs. Nature Feb. 15, 2012;482(7385) 339-346 (8 pages).
Hacket et al., in "A Transposo and Transposase System for Human Application." (Mol Ther vol. 18, No. 4, pp. 674-683, published on-line Jan. 2, 2010).
Hackett et al in "A Transposon and Transposase System for Human Application." (Mol Ther vol. 18, No. 4, pp. 674-683, published online Jan. 26, 2010).

(56) References Cited

OTHER PUBLICATIONS

Ivics et al, "Targeted Sleeping Beauty Transposition in Human Cells, Molecular Therapy," (2007), pp. 1137-1144, Max Delbrück Center for Molecular Medicine, Berlin, Germany; Institute of Biochemistry, Biological Research Center of the Hungarian Academy of Sciences, Szeged, Hungary.
Jarvius et al., In Situ Detection of Phosphorylated Platelet-derived Growth Factor Receptor 13 Using a Generalized Proximity Ligation Method. Mol Cell Proteomics. Sep. 2007;6(9):1500-1509.
Jenuwein and Allis, Translating the Histone Code. Science. Aug. 10, 2001;293(5532):1074-1080.
Jones et al., Mammalian chromodomain proteins: their roles in genome organisation and expression: Bioessays. Feb. 2000;22(2):124-137.
Jones et al., Methylated DNA and MeCP2 recruit histone deacetylase to repress transcription. Nat Genet. Jun. 1998; 19(2):187-191.
Kettlun, C. et al., "Manipulating piggyBac Transposon Chromosomal Integration Site Selection in Human Cells," Molecular Therapy, vol. 19, No. 9, pp. 1636-1644, Sep. 2011.
Kidder B.L. et al. "ChIP-Seq: technical considerations for obtaining high-quality data," Nature Immunology, 2011, vol. 12, No. 10. p. 918-922, especially abstract, p. 918, 920. fig. 1.
Kidder et al in ChIP-Seq: technical considerations for obtaining high-quality data (Nature Immunology vol. 12, No. 10, Oct. 2011, pp. 918-922).
Knoepfler, Paul S. et al., "Sin Meets NuRD and Other Tails of Repression", Cell Press, vol. 99, 447-450, Nov. 24, 1999.
Knyazhanskaya et al., Approaches towards directed DNA integration by the use of retroviral integrases and transposases, Molecular biology, vol. 45, No. 6, 931-948 (published in Russian).
Knyazhanskaya et al., Approaches towards directed DNA integration by the use of retroviral integrases and transposases, Molecular biology, vol. 45, No. 6, pages renumbered to 1-20 due to English translation (English translation of D13).
Koripelly, et al, Dual Sensing of Hairpin and Quadruplex DNA Structures Using Multicolored Peptide Nucleic Acid Fluorescent Probes, Bioconjugate Chem, 2010, 21 (11), pp. 2103-2109.
Lee et al, "Studying the recruitment of Sp1 to the beta-globin promoter with an in vivo method: Protein position Identification with nuclease tail (PIN*POINT)," Feruary 1998, pp. 969-974, Proc. Natl. Acad. Sci. USA.
Li et al., ChIA-PET tool for comprehensive chromatin interaction analysis with paired-end tag sequencing. Genome Biol. 2010;11(2):R22 (13 pages).
Lieberman-Aiden et al., Comprehensive Mapping of Long-Range Interactions Reveals Folding Principles of the Human Genome. Science. Oct. 9, 2009;326(5950):289-293.
Life Science Tools and Reagents: Global Markets Apr. 2011. 2011, BCC Research, Inc., Wellesley, MA USA. (7 pages).
Luger, et al., Crystal structure of the nucleosome core particle at 2.8 A resolution. Nature. Sep. 18, 1997;389 ;6648):251-260.
Mahnke Braam and Reznikoff, Functional Characterization of the Tn5 Transposase by Limited Proteolysis. J Biol Them. May 1, 1998;273(18):10908-10913.
Mahnke Braam et al., A Mechanism for Tn5 Inhibition. Carboxyl-Terminal Dimerization. J Biol Chem. Jan. 1, 1999;274(1):86-92.
Maragathavally, K.J. et al., Chimeric Mos1 and piggyBac transposases result in site-directed integration. The FASEB Journal, 20: 1880-1882 and E1188-E1195.
Mizuucki and Baker, Chemical Mechanisms for Mobilizing DNA, in Mobile DNA II, Craig, et al., Eds. 2002, ASM Press: Washington, pp. 12-23.
Newman et al. ("An abundant evolutionarily conserved CSB—PiggyBac fusion protein expressed in Cockayne syndrome." PLoSgenetics 4.3 (2008): 14 pages.) (Year: 2008).
Novus Biologicals, "Chromatin Immunoprecipitation Troubleshooting, Novus Biologicals," Apr. 23, 2012, 2 pages, retrieved online Oct. 18, 2021 at https://www.novusbio.com/support/support-by-application/chromatin-immunoprecipitation/troubleshooting.html.

Opposition Against EP2999784B1 Filed at the European Patent Office on Sep. 30, 2020.
Ren, Yongsheng, et al., "Transcription Factor Ap-2 Functions as a Repressor That Contributes to the Liver-specific Expression of Serum Amyloid A1 Gene", The Journal of Biological Chemistry, vol. 276, No. 21, Issue of May 25, pp. 17770-17778, 2001.
Rister and Desplan, Deciphering the genome's regulatory code: The many languages of DNA. Bioessays. May 2010;32(5):381-384.
Ryuji Ikeda et al. Sleeping Beauty Transposase has an Affinity for Heterochromatin Conformation; Molecular and Cellular Biology, Mar. 2007, p. 1665-1676, vol. 27, No. 5.
Sandoval et al. (Nucleic Acids research 32. 11 (2004): 8 pages) (Year: 2004).
Sapjnikova et al.( "Biochemical observation of the rapid mobility of nuclear H MGB1." Biochimica et Biophysica Acta (BBA)—GeneStructure and Expression 1729.1 (2005): 57-63.) (Year: 2005).
Schmid et al, "ChIC and ChEC; Genomic Mapping of Chromatin Proteins," 2004, Molecular Cell, vol. 16, pp. 147-157, Cell Press.
Schmidl, Christian, et al. "ChIPmentation: fast, robust, low-input ChIP-seq for histones and transcription factors", Nat Methods, Oct. 2015; 12(10): 963-965. doi: 10.1038/nmeth.3542.
Shi et al., Efficient transposition of preformed synaptic Tn5 complexes in Trypanosoma brucei. Mal Biochem Parasitol. Apr. 30, 2002;121(1):141-144.
Simon et al., The genomic binding sites of a noncoding RNA. PNAS USA Dec. 20, 2011:108(51)20497-20502.
Solulink, Protein-Protein Conjugation Kit Solulink Inc.: San Diego. Technical Manual May 29, 2013 accessed online at: http://www.solulink.com/products/ptm/S-9010-1-ProteinProteinConjugationKit.pdf : 16 pages.
Steensel et al, "Identification of in vivo DNA targets of chromatin proteins using tethered Dam methyltransferase," Apr. 2000, pp. 424-428, Nature Biotechnology.
Steger et al., Doti UKMT4 Recruitment and H3K79 Methylation Are Ubiquitously Coupled with Gene Transcription Mammalian Cells. Mol Cell Biol. Apr. 2008;28(8):2825-2839.
Strahl and Allis, The language of covalent histone modifications. Nature. Jan. 6, 2000;403(6765):41-45.
Suganuma and Workman, Crosstalk among Histone Modifications. Cell. Nov. 14, 2008;135(4):604-607.
Suganuma et al., Tn5 Transposase-Mediated Mouse Transgenesis. Biol Reprod. Dec. 2005;73(6):1157-1163.
Syed et al, Optimized library preparation method for next-generation sequencing, Oct. 2009, pages i:ii, Nature Methods, Epicentre Biotechnologies, Madison, Wisconsin, USA.
Tan W. et al., "Fusion Proteins Consisting of HIV-1 integrase and the Designed Polydactyl Zinc Finger Protein E2C Direct Integration of Viral DNA into Specific Sites," Journal of Virology, vol. 78(3), pp. 1301-1313, Feb. 2004).
U.S. District Court, District of Delaware, "Defendant Epicypher, Inc's Initital Invalidity Contensions," Aug. 13, 2021, C.A. No. 1:20-CV-01568-MSG. 91 pages.
USPTO, Non-Final Office Action for U.S. Appl. No. 14/359,877; dated Apr. 27, 2017, 43 pages.
Vidal et al., Use of an EZ-Tn5-Based Random Mutagenesis System to Identify a Novel Toxin Regulatory Locus in Blostridium perfringens Strain 13. PLoS One. Jul. 14, 2009;4(7):e6232 (13 pages).
Vire et al., The Polycomb group protein EZH2 directly controls DNA methylation. Nature. Feb. 16, 2006;439 7078):871-874.
Wang et al, "Calling Cards Enable Multiplexed Identification of the Genomic Targets ofDNA-Binding Protein," Apr. 6, 2011, pp. 748-755, Genome Research.
Wang et al, 'Calling Cards' method for high-throughput identification of targets of yeast DNA-binding proteins, Sep. 11, 2008, pp. 1569-1577, Nature Protocols, Department of Genetics, Washington University, School of Medicine, Genome Sequencing Center, St. Louis, Missouri USA.
Wang et al, "Calling Cards for DNA-Binding Proteins in Mammalian Cells," Mar. 2012, pp. 941-949, Genetica, Department of Genetics and Center for Genome Sciences and Systems Biology, Washington University, School of Medicine, St. Louis, Missouri, USA.

(56) References Cited

OTHER PUBLICATIONS

Wang et al, "Calling Cards for DNA-Binding Proteins," Theses, Aug. 2009, Washington University in St. Louis, USA, 184 pages.

Wang et al, Calling cards for DNA-binding proteins, date (2007), pp. 1202-1209, Genome Research, Department of Genetics, Washington University, School of Medicine, Genome Sequencing Center, St. Louis, Missouri.

Xu et al., A signal-noise model for significance analysis of ChIP-seq with negative control. Bioinformatics. May 1, 2010;26(9):1199-1204.

* cited by examiner

EPICENTRE

"A-METS"  5'-GCCTCCCCTCCCGCCATCAGAGATGTGTATAAGAGACAG-3'
"p-MENTS"                     3'-TCTACACATATTCTCTGTC-PO4-5'

"B-METS"  5'-CCCCTTCCCACCCCCGCTCAGAGATGTGTATAAGAGACAG-3'
"p-MENTS"                      3'-TCTACACATATTCTCTGTC-PO4-5'

ILLUMINA

"A-METS"  5'-TCGTCCCCCAGCCGTCAGATGTGTATAAGAGACAG-3'
"p-MENTS"                    3'-TCTACACATATTCTCTGTC-PO4-5'

"B-METS"  5'-GTCTCGTGGGCTCGGAGATGTGTATAAGAGACAG-3'
"p-MENTS"                   3'-TCTACACATATTCTCTGTC-PO4-5'

Fig. 18

1) 2,2'-dithiobis (5-nitropyridine), triethylamine, acetonitrile (60%)
2) N-Hydroxysuccinimide, N,N'-dicyclohexylcarbodiimide, acetonitrile (70%)

Figure 34
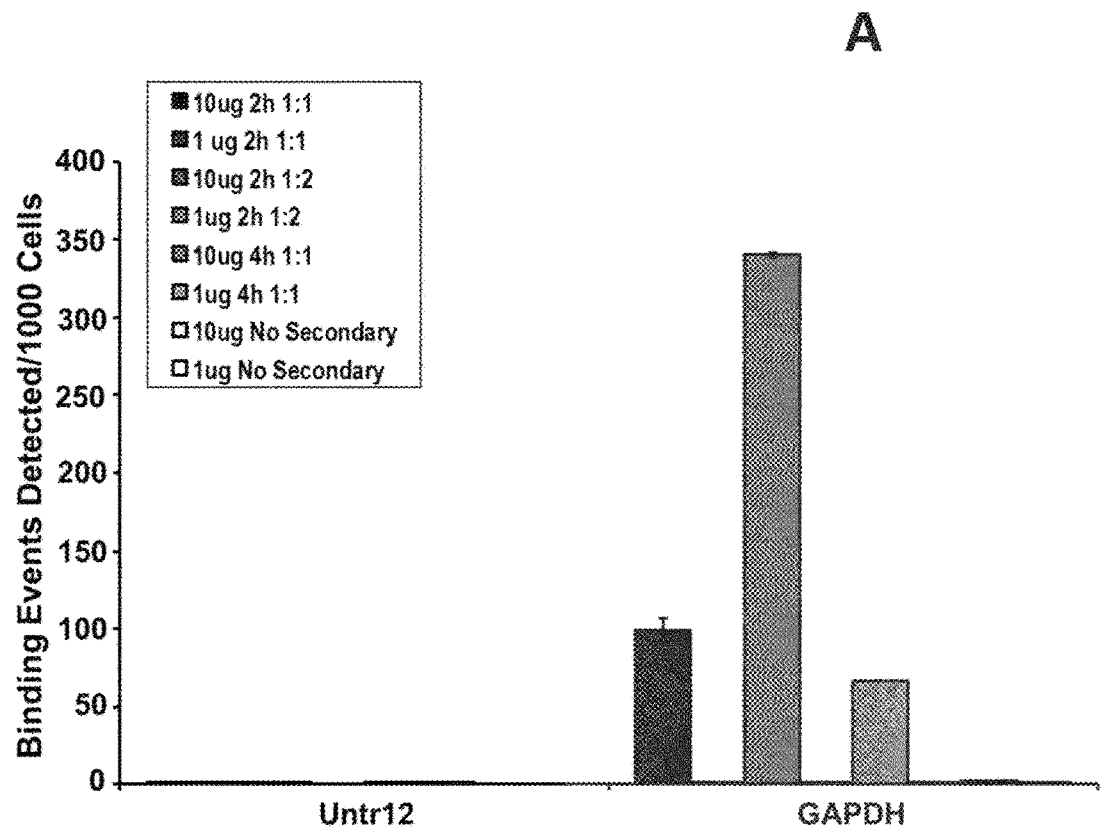
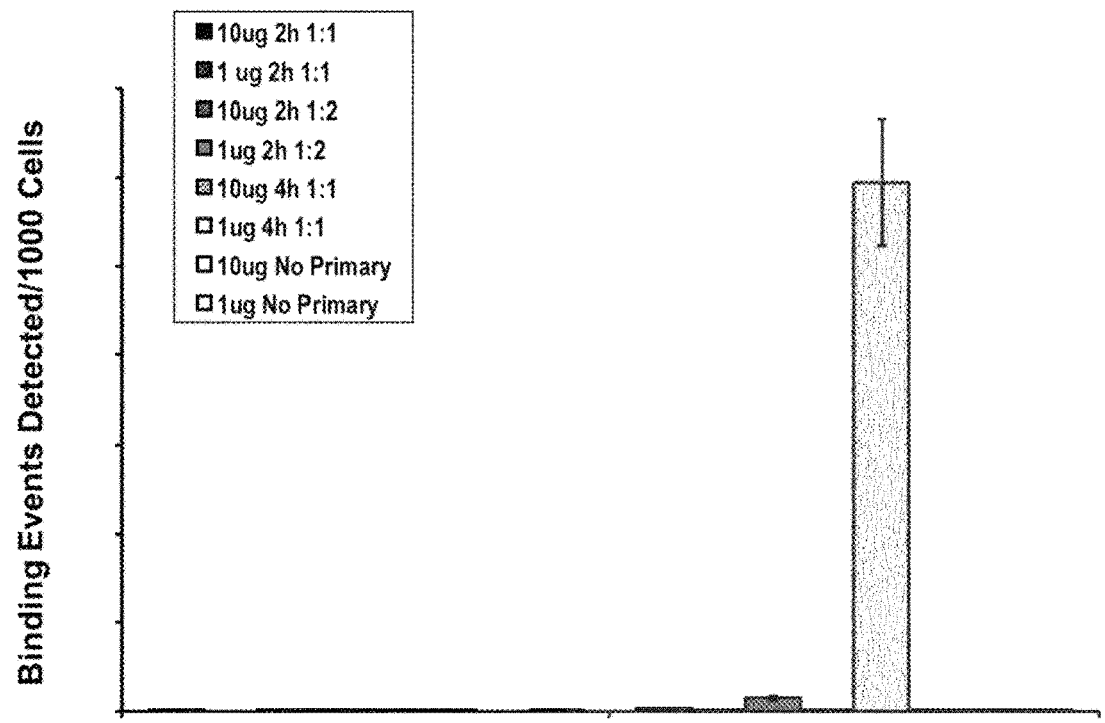

| Incubate the DNA with His-tagged MBD2b/MBD3L1 and magnetic nickel beads |

1 hour 4°C
100 ul

High/Low Salt
Binding Buffer

| Capture the methylated DNA-protein complexes with the nickel coated magnetic beads |

High/Low Salt
Binding Buffer

| Wash to remove the unmethylated DNA fragments |

Wash 4x with 200 ul Binding Buffer

| Elute the bound methylated DNA while simultaneously degrading the proteins |

100 ul Elution Buffer + Prot K
50°C 30 minutes

| DNA clean up using the ChIP DNA Purification Columns |

| The purified methylated DNA is ready for PCR analysis |

Fig. 37

TARGETED TRANSPOSITION FOR USE IN EPIGENETIC STUDIES

FIELD OF THE INVENTION

The present invention is in the field of epigenetics. More specifically, compositions, methods and kits useful for epigenetic analysis based on the use of transposons to specifically target specific regions of chromatin.

BACKGROUND OF THE DISCLOSURE

Overview of Epigenetic Mechanisms

Epigenetics is broadly defined as changes in phenotype that are heritable but do not involve changes in the DNA sequence, and, from a historical perspective, stems from long-standing studies of seemingly anomalous (i.e., non-Mendelian) and disparate patterns of inheritance in many organisms [1]. Examples include variation of embryonic growth, mosaic skin coloring, random X inactivation, and plant paramutation. Discoveries in a large number of different model systems have been pivotal in identifying the three principle epigenetic mechanisms of (i) histone modifications, (ii) DNA methylation, and (iii) non-coding RNAs, which function in concert to influence cellular processes such as gene transcription, DNA repair, imprinting, aging, and chromatin structure, as depicted in FIG. 2.

Gene transcription occurs in the context of the nucleosomal structure of chromatin. A nucleosome consists of an octamer of histone proteins (two molecules of each core histone H2A, H2B, H3, and H4) around which is wrapped 147 base pairs (bp) of DNA. Histones are small basic proteins with an unstructured amino-terminal "tail" that are the target of numerous post-translational modifications [2, 3]. Specific histone marks in the fission yeast *Saccharomyces pombe* were demonstrated to be directly operating as activating and repressing signals for gene transcription [4]. Methylation of lysine 4 and acetylation of lysine 9 of histone H3 are associated with transcriptionally active chromatin, while methylation of lysine 20 of histone H4 and methylation of lysine 9 and 27 of histone H3 are repressive marks, found in transcriptionally silent heterochromatin regions [5, 6]. The repressive histone H3 lysine 9 trimethyl-mark is bound by HP1 proteins, which in turn recruit non-coding RNAs involved in regulating heterochromatin formation [7].

Similar mechanistic links have also been identified between histone marks and DNA methylation. Highly repetitive DNA tandem repeat sequences such as those found in pericentric heterochromatin rely on the repressive H3K9 methylation mark to direct de novo DNA methylation while at promoters, EZH2, a histone lysine methyltransferase containing complex is involved [8]. Members of the methyl-CpG binding domain (MBD) family of proteins which are readers of DNA methylation are found in complexes with histone modifying enzymes (MeCP2 recruits histone deacetylases to mediate histone repressive marks [9]). Studies in multicellular organisms such as the invertebrates *Caenorhabditis elegans* and *Drosophila melanogaster* and plants such as *Arabidopsis thaliana* have generated crucial links between these epigenetic mechanisms [10].

In spite of all the advances to date, however, the epigenetics research field is still in the discovery phase, with many mechanistic questions remaining unanswered and many key players yet to be identified. Just as in the past, the continued study of epigenetic mechanisms in a variety of model organisms will be required to answer these questions. Development of enabling technologies suitable for a broad spectrum of model systems are also critical for accelerating the rate of discovery, especially since the various epigenetic mechanisms are functionally interconnected.

Chromatin Immunoprecipitation (ChIP)

ChIP was first described in 1993 following studies of the association of histone acetylation state with transcriptional gene silencing in yeast [11]. Its adaptation to mammalian cells was reported five years later, in 1998 [12]. Since its initial description, the technique has remained essentially unchanged. As described below and depicted in FIG. 1, Panel A, DNA sequence analysis is performed on the fraction of DNA isolated by immunoprecipitation with antibodies specific to the protein of interest. This technique is used in a wide variety of applications. These include profiling histone modification patterns, from their intragenic distribution through to genome-wide analysis, determining the composition of protein complexes recruited by specific histone marks, identifying regions of de novo DNA methylation, or, with some modifications to the procedure, detecting nascent non-coding RNAs.

Advances in PCR and DNA sequencing technologies have positively impacted the DNA analysis portion of the ChIP technique, which has expanded from semi-quantitative analysis of single genes using end-point PCR, to quantitative analysis with real-time PCR, through to genome-wide analysis afforded by ChIP-ChIP, wherein the captured DNA is used to probe a high-density microarray, or ChIP-Seq, wherein the captured DNA is subjected to NGS ("next generation sequencing") [6, 13]. While these improvements have increased the magnitude of sequence information available for analysis from a single reaction, the limitations associated with efficient immunocapture of protein-associated DNA have not been addressed.

Only incremental improvements, such as the introduction of magnetic beads for immunocapture in place of agarose or sepharose beads, as in Active Motifs ChIP-IT Express™ kit, have been made [14]. The improved recovery (fewer beads are lost during wash steps), reduced background (wash steps are more thorough) afforded through the use of magnetic beads has allowed for a ten-fold reduction in the sample size requirements, from 2-10 million cells to 0.1-1 million cells. In general, these lower sample requirements apply only to high affinity antibodies targeting abundant proteins, such as RNA polymerase II or histone modifications. In addition, the sample size requirement remains a considerable barrier in some research areas, such as embryology and stem cells where cell numbers are very limiting, and is further compounded by the limitation that the only a single protein can be analyzed in each ChIP experiment. The number of cells required is thus directly proportional to the number of proteins to be analyzed, impacting cost and time considerations. An additional challenge stems from the need of ultra-high affinity antibodies for use in this technique. Many antibodies qualified for use in immunofluorescence and/or immunohistochemistry, which can be used to demonstrate in situ association of the protein of interest with DNA or chromatin, or antibodies which have been shown to effectively function in immunoprecipitation, fail in ChIP applications where the target protein is present in high molecular weight multi-protein-chromatin complexes containing DNA fragments up to 1 kb (kilobase) in length. The binding affinity of the antibody for its cognate target must be strong enough to withstand the physical forces associated with constant agitation of the suspension and immobilization by the beads used to isolate the complexes.

Chirp (Chromatin Isolation by RNA Purification) and CHART (Capture Hybridization Analysis of RNA Targets)

Non-coding RNAs (ncRNAS) have multiple functions in the cell, for example, one described function is for the RNA molecule itself to function as a scaffold that directs and maintains the assembly and stability of multiprotein complexes. These complexes often contain chromatin targeting and chromatin modifying proteins that assemble into DNA as part of the overall chromatin structure.

Since ncRNAs are known to be part of important chromatin modifying complexes, techniques have been developed to identify how such RNA interacts with DNA across the genome, for example, Chirp and CHART. Both Chirp and CHART are essentially the same and are described in brief below.

1. A Series of biotinylated oligonucleotides are designed to hybridize to the ncRNA of interest.
2. Formaldehyde fixed chromatin is prepared (similar to what is done for ChIP)
3. Oligonucleotides are hybridized to the native target within the chromatin prep
4. Streptavidin beads are used to pull out the ncRNA of interest, associated proteins and associated genomic DNA
5. After isolation and clean-up of genomic DNA, libraries are prepared and the DNA is sequenced using Next-Gen sequencing platforms such as Illumina.

These techniques are very similar to ChIP but rather than using an antibody to isolate the genomic DNA associated with proteins, oligonucleotides are used to isolate the genomic DNA associated with ncRNAs [38-40].

Need for and Benefits of the Invention

The instant invention has broad and significant practical applications. These applications span all life sciences research with eukaryotic organisms, because epigenetic mechanisms are highly conserved throughout eukaryotes. The methods of this invention are more efficient than existing methods such as ChIP. These new, patentable methods enable concurrent analysis of multiple chromatin-associated proteins, eliminate the labor intensive NGS library preparation procedures, and have the potential to significantly reduce the amount of samples needed compared to traditional ChIP methods. This is relevant to not only to the stem cell and embryology research fields where samples are limiting, but also fields such as high throughput screening of large numbers of samples in clinical and pharmaceutical applications, where miniaturization is a major cost driver. In addition, ChIP analysis is limited by the small percentage of antibodies that work effectively in the method. Since the methods of the invention do not require immunoprecipitation, antibodies that do not work in ChIP can be adapted to work with the instant invention, thereby expanding the number of cellular proteins whose genomic distribution can now be determined.

SUMMARY OF THE INVENTION

One aspect of the invention concerns methods and reagents for making a nucleic acid sequence library or libraries. Such methods involve extracting and optionally fragmenting chromatin from a prepared sample, adding at least one protein-oligonucleotide conjugate comprising an extraction moiety, allowing said protein(s) to locate at its/their target protein(s) and or DNA-binding sites, and or RNA-binding sties in said chromatin fragments, tagging the nucleic acid in said chromatin fragments with said conjugate by inducing an intermolecular reaction between said oligonucleotide and said nucleic acid, extracting the nucleic acid so tagged using the extraction moiety. In other aspects, the extracted tagged nucleic acid is sequenced.

Another aspect of the invention concerns methods and reagents for making a nucleic acid sequence library or libraries. Such methods involve extracting and optionally fragmenting chromatin from a prepared sample, adding at least one oligonucleotide-transposome construct comprising an extraction moiety, allowing said oligonucleotide-transposome construct to locate at its/their DNA and/or noncoding RNA-binding sites in said chromatin, tagging the nucleic acid in said chromatin fragments with said construct by inducing an intermolecular reaction between said oligonucleotide and said nucleic acid, extracting the nucleic acid so tagged using the extraction moiety. In a related embodiment the oligonucleotide contains peptide nucleic acid that targets G-quadruplex structures. In other aspects, the extracted tagged nucleic acid is sequenced.

The methods disclosed herein can be applied to eukaryotic and prokaryotic, e.g., bacterial organisms [43-46].

The methods disclosed herein can be applied to samples in which the chromatin has been crosslinked to proteins in vivo or samples without crosslinking.

In some embodiments, the protein-oligonucleotide conjugate or oligonucleotide-transposome construct further comprises transposase and the intermolecular reaction is transposition, the extraction moiety is a biotin molecule, and/or the intermolecular reaction is selected from the group: transposition, ligation, recombination, hybridization, and topoisomerase-assisted insertion.

A related aspect of the invention concerns antibody-transposome complexes. Such complexes comprise an antibody that binds a target nucleic acid-associated protein conjugated to a transposome that comprises a transposase and a transposon cassette.

In still another related aspect, disclosed herein are protein-transposome complexes. Such complexes comprise a protein that binds, without limitation, a protein-binding partner, methylated DNA, non-coding RNA, and/or DNA-binding site. In another embodiment, the protein is an antibody or antibody fragment (both encompassed by the term antibody). In still another embodiment, the protein contains particular binding motifs, such as, without limitation, bZIP domain, DNA-binding domain, helix-loop-helix, helix-turn-helix, MG-box, leucine zipper, lexitropsin, nucleic acid simulations, zinc finger, histone methylases, recruitment proteins, Swi6, chromodomain, chromoshadow domains, bromodomains, or PHD-finger. In some embodiments, the protein is MBD2 or MBD3.

In still another related aspect, disclosed herein are oligonucleotide-transposome constructs. Such constructs comprise an oligonucleotide that targets non-coding RNA and/or G-quadruplex structures. In a related embodiment, the oligonucleotide can contain locked nucleic acids and/or peptide nucleic acid-nucleic acid chimeras.

In some embodiments, the transposome is comprised of Tn5 or TS-Tn5 transposon.

An embodiment disclosed herein are kits including reagents, protein-transposome comoplex(s) and/or oligonucleotide-transposome construct(s), and instructions for their use.

Another aspect of the invention relates to methods for performing proximity ligation. Such methods include contacting a crosslinked and fragmented chromatin sample with an antibody-oligonucleotide conjugate under dilute conditions to promote ligation of the ends of the chromatin fragment to the ends of the oligonucleotide of the antibody-oligonucleotide conjugate, wherein the oligonucleotide is double stranded and comprises at least two recognition sites for a freeing restriction enzyme, primer sites for amplification, at least one bar code sequence to identify the conjugated antibody, complementary overhangs to facilitate ligation, and optionally, a spacer for optimizing the length of the oligonucleotide, and then ligating the antibody-oligonucleotide conjugates to the crosslinked and fragmented chromatin sample.

A related aspect involves antibody-oligonucleotide conjugates useful for proximity ligation reactions. These typically comprise an antibody that binds a target nucleic acid-associated protein that is conjugated to a double-stranded oligonucleotide that comprises at least two recognition sites for a freeing restriction enzyme, primer sites for amplification, at least one bar code sequence to identify the conjugated antibody, complementary overhangs to facilitate ligation, and optionally, a spacer for optimizing the length of the oligonucleotide.

Another embodiment disclosed herein are methods to enrich for DNA methylated genomic regions using transposome-antibody/Oligonucleotide complex as described in Example 14 and FIG. 40. In an aspect of this embodiment, the enrichment is performed using unfragmented genomic DNA or Chromatin.

All publications, patents, patent applications cited herein are hereby expressly incorporated by reference for all purposes.

BRIEF DESCRIPTION OF THE DRAWINGS

FIG. 18—shows comparisons of Epicentre and Illumina oligonucleotide sequences. During the assembly of the transposome complex the transposase enzyme will bind to a 19 bp double stranded transposon DNA (purple). Illumina complete changed the sequence of the single stranded appended ends seen in black to make the subsequent tagmented DNA compatible with their index adapters and primers in the Nextera Index kit. A-METS EPICENTRE is SEQ ID NO: 9; A-METS Illumina is SEQ ID NO: 10; B-METS EPICENTRE is SEQ ID NO: 11; B-METS Illumina is SEQ ID NO: 12; p-MENTS is SEQ ID NO: 13

FIG. 34—shows optimization of TTAM-ChIP. The numbers along the x-axis directly correspond in sequence to the following conditions listed in the embedded figure legend.

FIG. 37—shows the traditional MethylCollector™ approach that is modified to include the transposase.

DETAILED DESCRIPTION OF THE EMBODIMENTS

The disclosure herein provides methods of tagging and isolating DNA or other nucleic acids that are associated with a protein or proteins of interest. Generally the methods comprise first preparing complexes of oligonucleotide tag(s) or barcode(s) with antibody(ies) that recognize protein(s) of interest in chromatin or that are otherwise associated with nucleic acids. The tagged oligonucleotide complexes may further comprise an extraction moiety, such as a biotin molecule (or other member of a high affinity binding pair), that can be used to extract or isolate the tagged nucleic acid. A "binding partner" or "member" of a high affinity binding pair (i.e., a pair of molecules wherein one of the molecules binds to the second molecule with high affinity (e.g., biotin and avidin (or streptavidin), carbohydrates and lectins, effector and receptor molecules, cofactors and enzymes, enzyme inhibitors and enzymes, and the like).

Next, when the complexes are added to the nucleic acids, the antibody(ies) recognize or bind to the protein(s) of interest that are associated with the nucleic acids. Using a variety of intermolecular reactions, the nucleic acid proximate those proteins is tagged with the complex. Thus, the proximate nucleic acid is tagged with one or more oligonucleotide bar code(s) and, optionally, a moiety that allows for purification or isolation.

One embodiment of the invention, termed "Transposase-Assisted Multi-analyte Chromatin ImmunoPrecipitation" or "TAM-ChIP", is a unique method that significantly improves ChIP, the principle technique currently used to study how histone post-translational modifications and the proteins which they recruit regulate gene expression. Traditional ChIP is a cumbersome multiday, multistep procedure that requires large numbers of cells, ultra-high affinity antibodies for the immunocapture of large protein-chromatin complexes, and is limited to the analysis of a single protein species per sample.

Figure 1:
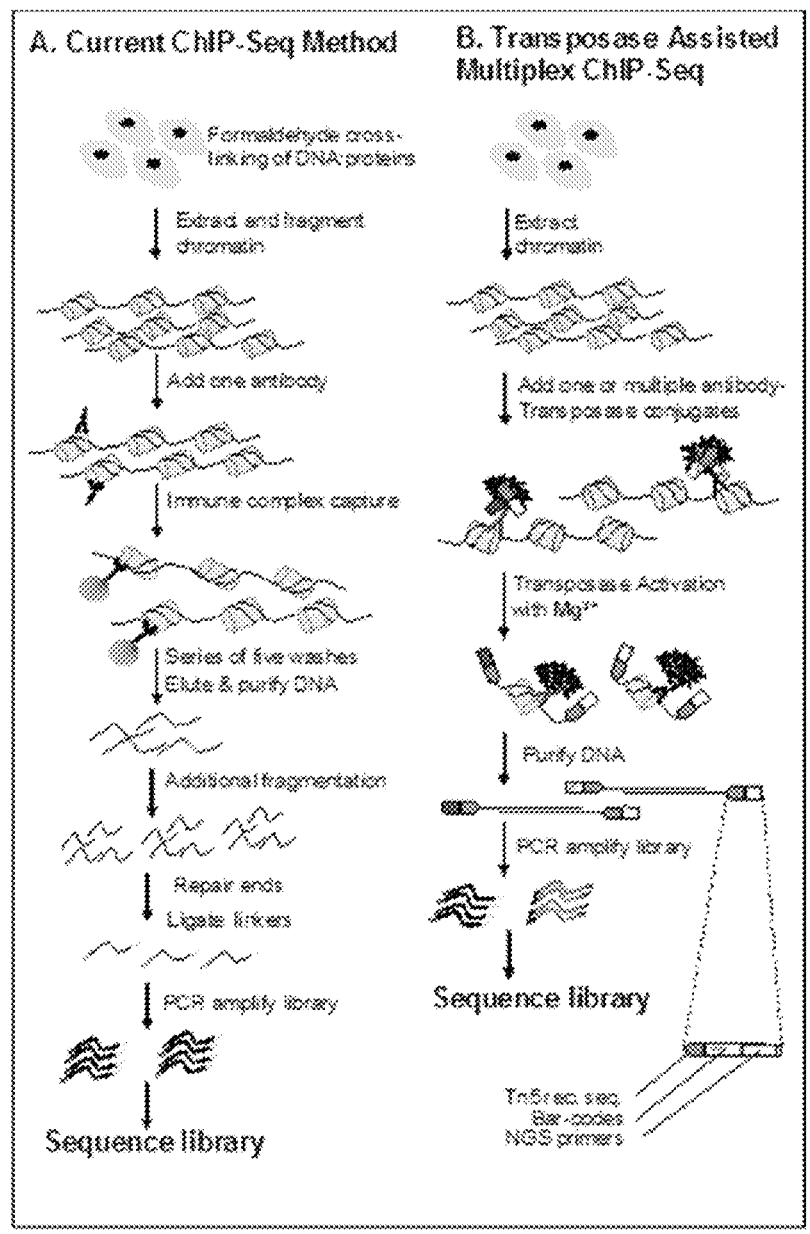
FIG. 1—shows a comparison of ChIP-Seq Methods
Figure 2:
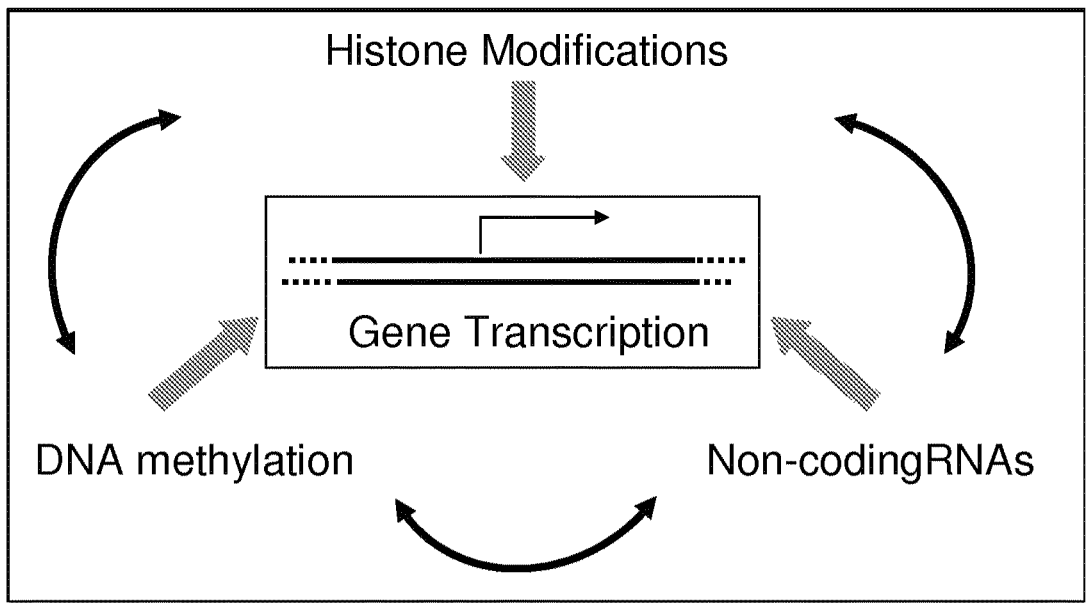
FIG. 2—shows some epigenetic mechanisms that interact to influence gene transcription.

Briefly, conventional ChIP methods involve the crosslinking of DNA and protein in live cells, isolation of crosslinked material, shearing of DNA (still bound, through crosslinking, to protein), immunoprecipitation of the crosslinked DNA-protein complexes via antibody-binding of the protein of interest (still bound to DNA), reverse-crosslinking of DNA and proteins, and the detection or sequencing of DNA molecules that were crosslinked to the immunoprecipitated DNA-protein complexes, allowing the generation of specific, DNA sequence context data (FIG. 1, Panel A). For ChIP-Seq applications, the elapsed time from formaldehyde crosslinking of cells to sequencing-ready library is typically five days. Relative to the advances made in the understanding the epigenetic mechanisms of DNA methylation and micro- or non-coding RNAs, the limitations of the ChIP technique have significantly hampered the understanding of the biological function of histone modifications.

In contrast, TAM-ChIP (FIG. 1, Panel B) removes a number of technical and sample-size barriers associated with traditional ChIP (see Table 1) by eliminating the inefficient immunoprecipitation and labor intensive library preparation steps of the method and bringing high throughput sample processing and multi-analyte capabilities to the ChIP method.

other suitable support conjugated to the other member of the selected high affinity binding pair);

unique bar code sequences (i.e., short nucleotide sequences, i.e., from 1-1,000 bases, preferably 1-50 bases, preferably fewer than 20, even more preferably fewer than 10 bases) that uniquely label an oligonucleotide species so that it can be distinguished from other oligonucleotide species in the reaction, and which correspond to a particular antibody) for antibody identification in multi-analyte applications in which multiple antibodies are used simultaneously with the same sample material;

for whole genome sequencing applications, platform-specific tags required for next generation sequencing (NGS).

In some aspects, rather than using a protein conjugated to a Transposome, the synthetic oligonucleotide described above will also contain sequences that are able to bind to non-coding RNA, such sequences may include locked nucleic acids (LNA).

In still other aspects, rather than using a protein conjugated to a Transposome, the Transposome with synthetic oligonucleotide will be conjugated to a molecule that recognizes G-quadruplex structures, such as small molecules and/or peptide nucleic acids (PNA). DNA-PNA chimeric oligomers can be synthesized using techniques known in the art [42].

The antibody-transposase conjugates are incubated with chromatin fragments extracted from isolated cells, tissue, or whole organs (or other cell-containing biological samples) to allow specific antibody-protein binding. The transposase is subsequently activated by addition of a cofactor, e.g., $Mg^{2+}$, after sample dilution to prevent inter-molecular events. Transposase activation results in insertion of the two transposase-associated oligonucleotides into the chromatin in proximity to the region where the antibody-associated DNA fragment bound, thereby producing analysis-ready

TABLE 1

|  | ChIP-Seq | | | TAM CHIP-Seq | | |
| --- | --- | --- | --- | --- | --- | --- |
|  | Steps | Reagents needed | Time | Steps | Reagents needed | Time |
| Cell fixation | 4 | 2 | 30 | 4 | 2 | 30 |
| Chromatin preparation | 5 | 2 | 30 | 1 | 1 | 5 |
| Shearing | 6 | 0 | 20 | 0 | 0 | 0 |
| ChIP reaction | 40 | 20 | 48 hours | 6 | 6 | 6 hours |
| Libraries | 12 | 19 | 8 hours | 3 | 3 | 1 hour |
|  | 67 steps | 43 reagents | 3-4 work days | 14 steps | 12 reagents | 1 work day |

TAM-ChIP enables rapid (<24 hour elapsed time) and streamlined analysis of one or several protein-chromatin interactions for analysis of a single gene all the way through to genome-wide interrogation. To achieve this, proteins, such antibodies specific for the protein(s) of interest, transcription factors, or chromodomains, such as in HP1 and Polycomb proteins are first conjugated to a transposase: transposon complex (Transposome™) charged with synthetic oligonucleotide(s) that comprise a transposon cassette containing the following features:

Transposase recognition sequences required by the for catalysis of the DNA integration reaction;

a biotin (or other) molecule conjugated to an oligonucleotide, preferably at one end, to facilitate purification of targeted DNA with streptavidin magnetic beads (or templates following a deproteination step and capture of biotin-tagged DNA fragments using streptavidin-coated magnetic beads.

Leveraging Tn5 Transposase for Improving ChIP

Figure 3:
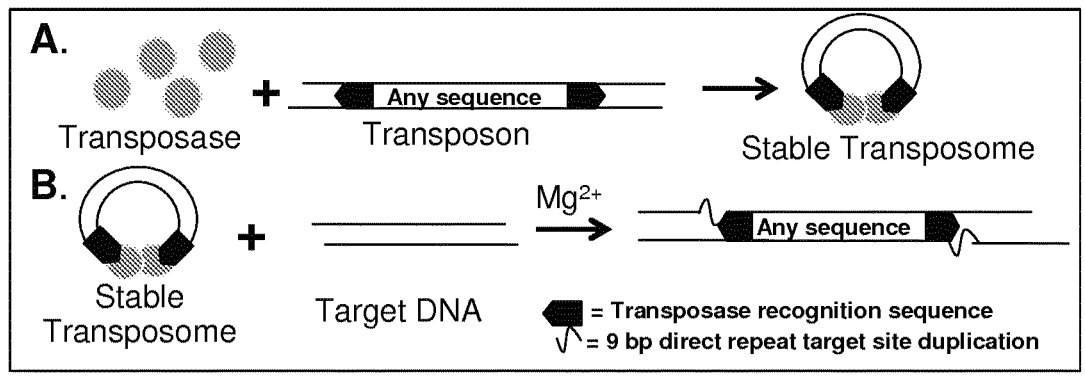
FIG. 3—shows a schematic diagram of Tn5 "cut and paste" transposition

Transposable elements are discrete DNA segments that can repeatedly insert into a few or many sites in a host genome. Transposition occurs without need for extensive DNA sequence homology or host gene functions required in classical homologous recombination [15]. Consequently, transposable elements have proven to be superb tools for molecular genetics and have been used extensively in vivo to link sequence information to gene function. More recently, in vitro applications have also been developed, specifically for Tn5, a class II "cut and paste" transposable element isolated from gram negative bacteria [16]. Catalysis involves nicking of DNA to generate nucleophilic 3' OH groups on both strands at the ends of the 19 bp Tn5 transposase DNA recognition sequence. The 5' ends are also cleaved within the synaptic complex, releasing the transposable element from the donor DNA (FIG. 3, Panel A). This mechanism allows for the formation of a stable complex between the enzyme and transposon in the absence of $Mg^{2+}$ [17], and is the basis for the in vitro transposase technologies developed by Epicentre Biotechnology (Madison, WI, USA).

Transposases are not conventional enzymes in the classical sense, in that there is no turn-over. Spontaneous product release is not required and consequently the transposase is required in stoichiometric quantities [15].

Tn5-mediated transposition is random, causing a small 9 bp duplication of the target sequence immediately adjacent to the insertion site (FIG. 3, Panel B). The result is analogous to using a restriction endonuclease with random sequence specificity that also contains a ligase activity. Epicenter's EZ-Tn5 Transposome™ technology utilizes a transposase-transposon complex which exhibits 1,000 fold greater activity than wild type Tn5, achieved by combining a mutated recombinant Tn5 transposase enzyme with two synthetic oligonucleotides containing optimized 19 bp transposase recognition sequence [16, 18], and is the basis of Epicentre's Nextera™ product used to streamline NGS library preparation. Using such a recombinant enzyme (whether naturally occurring or engineered to have improved transposition activity), transposition occurs with at efficiencies of 0.5-5%, using as little as 50 ng of purified DNA, yielding >106 transpositions per reaction. The transposome is so stable that it can be introduced via electroporation into living organisms, both prokaryotic (Gram negative and Gram positive bacteria [19-22]) and eukaryotic (yeast, trypanosome, and mice [19, 23, 24]) where in the presence of endogenous $Mg^{2+}$, transposon insertion has shown to be random and stable. The ability of the Tn5 transposase to recognize eukaryotic chromatin as a substrate is extremely significant, as it can be adapted to transform ChIP into a multi-analyte method suitable for high through-put applications.

As described above and depicted in FIG. 1, Panel B, TAM-ChIP technology development uses an antibody-transposome linking moiety to effectively conjugate the Transposome™ to a targeting antibody that binds a targeted DNA-associated protein. Binding of the antibody to its target protein in chromatin (or other nucleic acids with which the protein associates in cells under physiological conditions) optimizes transposase activity with chromatin as a DNA substrate. The TAM-ChIP method involves allowing formation of complexes between the antibody-Transposome™ conjugate and chromatin fragments containing the antibody's target protein. The samples are then diluted (to ensure transposition of the oligonucleotide payload in the transposon cassette into the same DNA fragment) and the chromatin-associated-transposase activated by the addition of the $Mg^{2+}$ co-factor, resulting in the insertion of the transposon cassette containing bar-code sequences and NGS compatible primer sites into flanking DNA regions (FIG. 1, Panel B). Following DNA purification to remove proteins, PCR amplification (or another suitable amplification process) with primers complementary to the oligonucleotides in the can be performed to generate NGS compatible libraries for sequencing.

As described herein, the transposon is loaded with oligonucleotides containing both the transpose recognition sequences and sequences for sequencing on the Illumina platform. This enzyme-DNA complex (FIG. 9 (a)) is called a transposome, and the resulting fragmented DNA into which the transposase has inserted its oligonucleotides is called tagmented DNA.

Figure 10:
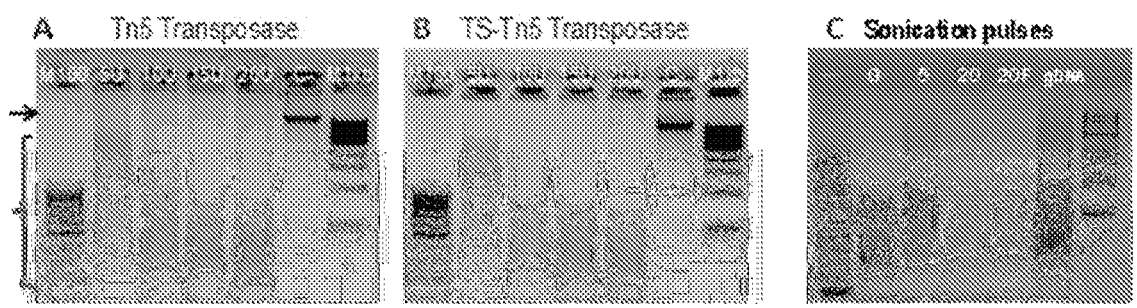
FIG. 10—shows Tn5 Transposase activity on Hela DNA and chromatin. Illumina Tagment DNA buffer and Tn5 (A) or TS-Tn5 (B) transposase, ranging from 5 to 20 Units, were added to HeLa DNA. The samples were incubated at 55° C. for 5 minutes and allowed to cool to 10° C. One fourth of the tagmented DNA was analyzed on a 1.5% agarose gel. C−, DNA with no transposase added. C. Tagmentation of Hela chromatin DNA. 25 Units of Tn5 transposome was added to 10 μg of crosslinked HeLa chromatin sonicated to varying extents. Tagmented chromatin was treated with RnaseA and Protein K and crosslinks reversed followed by purification. For the lane marked 20F, tagmentation products were first passed through a size exclusion spin column to remove low molecular weight DNA fragments and primers as well as salts and other impurities that could impede with the downstream PCR reaction. 100 ng of tagmented DNA was subjected to 15 cycles of PCR and one fifth of the PCR reaction volume was analyzed on a 1.5% agarose gel. gDNA=Naked genomic DNA subjected to tagmentation, purification and 100 ng of the purified product subjected to subsequent PCR amplification. MW markers: lowest band in M100=100 bp; Lowest band on M1kb=0.5 kB. next band=1. Arrow denotes position of input, untagemented DNA. Bracket denotes migration smear of randomly tagmented DNA fragments of varying sizes.

Applicants investigated two forms of the Tn5 enzyme for testing in TAM-ChIP. One form of the enzyme was the same as that sold in the Nextera kit (Tn5) while the second (TS-Tn5) was a temperature stable variant under development by Illumina. Applicants initially determined the compatibility of chromatin extraction buffers with the transposase enzymes and established that chromatin was recognized as a Tn5 transposase substrate. FIG. 10 shows that assembled enzyme:oligonucleotide complexes (Panel A, Tn5, Panel B, TS-Tn5) completely tagment purified genomic DNA from HeLa cells (human cervical carcinoma), a cell line routinely used in ChIP experiments. Buffer compatibility experiments established that relative to the reaction buffer provide in the Nextera kit, both transposase enzymes retained full activity in chromatin extraction buffers.

Also disclosed herein is the surprising discovery that sheering of chromatin by sonication to achieve smaller, soluble fragments is not necessary in TAM-ChIP. This unexpected result will further reduce technical barriers and equipment needs required for ChIP and other related techniques using the assisted transposon technology described herein.

The direct insertion of the oligonucleotide duplex in the transposon cassette by the transposase eliminates the need for immunoprecipitation, thereby reducing the input DNA requirement. It can also eliminate the need for ultra-high affinity antibodies, thereby expanding the application of the ChIP technique to a broader range of cellular targets which were previously excluded due to the lack of suitable antibodies. The inclusion of barcode sequences in the oligonucleotides allows for the identification of the corresponding immunoprecipitating antibody, and is the basis of the multianalyte potential of TAM-ChIP, which for the first time enables simultaneous use of multiple antibodies in the same sample and experiment. This innovation also has the benefits of further reducing sample size requirements and enables elucidation of protein co-association in sequence-specific contexts throughout the genome.

Figure 11:
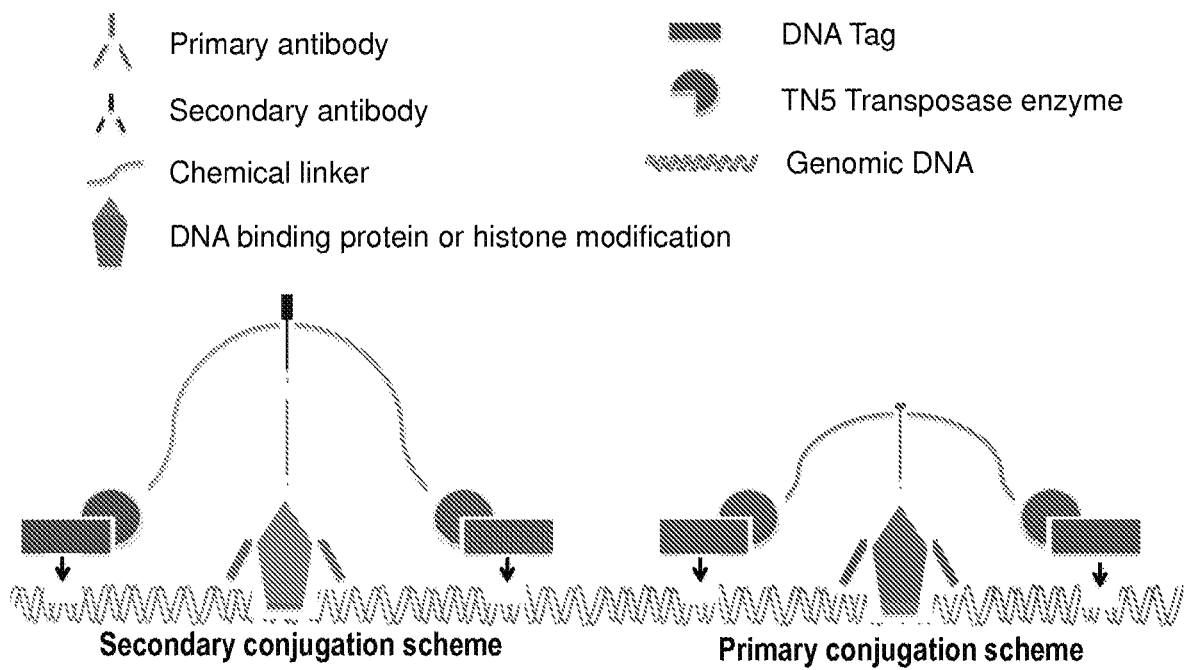
FIG. 11—shows the secondary and primary conjugation scheme.
Figure 12:
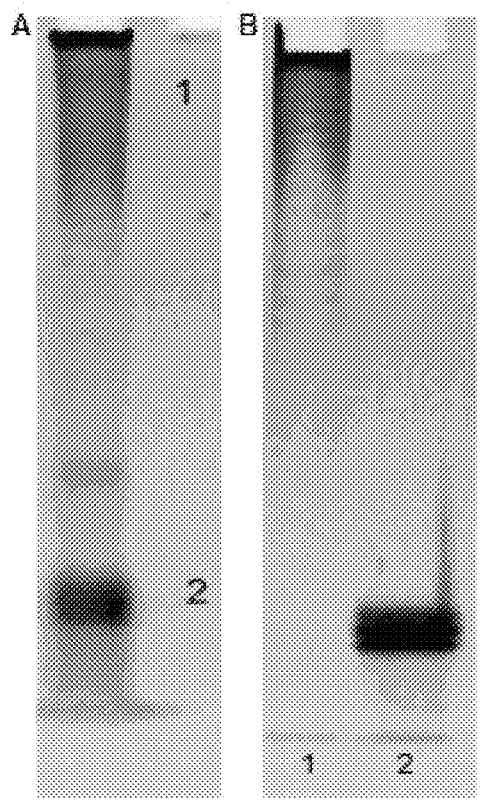
FIG. 12—shows Analysis of secondary antibody conjugate on 10% native polyacrylamide gel A. 2 μg of conjugated antibody loaded on a 10% native polyacrylamide gel and stained with GelRed nucleic acid stain. 1 indicates antibody-oligonucleotides conjugate zone and 2 oligonucleotides zone B. ¹/₁₅₀ of isolated chromatography peaks 1 and 2 from FIG. 16 loaded on a 10% native polyacrylamide gel and stained with GelRed nucleic acid stain. 1 indicates Chromatography peak "1" and 2 Chromatography peak "2". Peak "1" consists of pure antibody-oligonucleotide conjugate and is devoid of free oligonucleotide.

The construction of a functional antibody-transposome complex can be based on a primary conjugation scheme or secondary conjugation scheme as depicted in FIG. 11. Secondary antibody conjugates bind to primary antibodies and can be used in conjunction with any primary antibody, while primary antibody conjugates bind directly to their targeted protein. The DNA tag component of the primary conjugates can be changed, thus giving each primary conjugate a unique signature. Both approaches bring the TN5 Transposase enzyme into close proximity to DNA thus allowing DNA tagging to occur. Disclosed herein is a secondary conjugation scheme. This was achieved by first conjugating a mixture of the two oligonucleotides (six-molar excess) to an anti-rabbit secondary antibody such that a cleavable link between antibody and oligonucleotide was generated. Size exclusion chromatography was used to separate the antibody-oligonucleotide conjugate (FIG. 12, lane 1) from unincorporated oligonucleotides (FIG. 12, lane 2).

The functionality of this conjugate was tested in ChIP to confirm that the addition of oligonucleotides did not interfere with its ability to interact with rabbit primary antibodies. A two to three fold reduction was observed with the conjugate but was deemed not significant.

Figure 13:
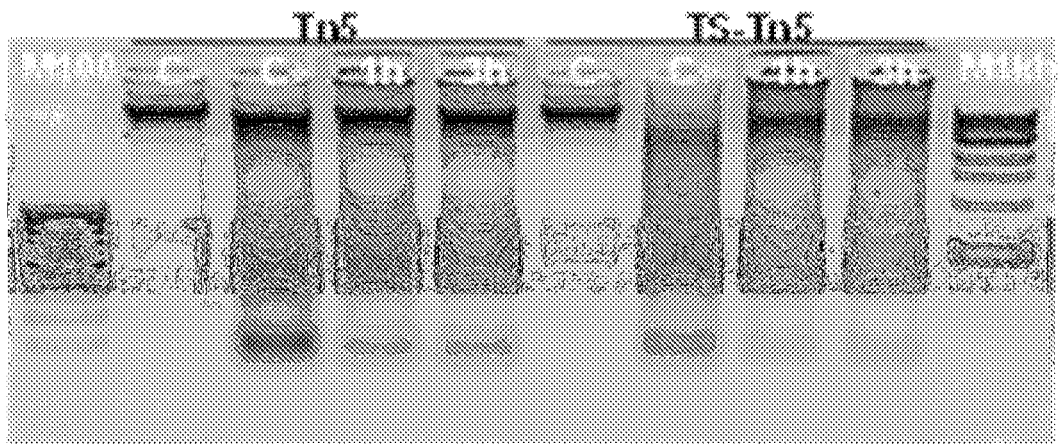
FIG. 13—shows a Comparison of fragmentation of genomic DNA by Tn5 and TS-Tn5 transposome-antibody conjugates at different temperatures and free Tn5 enzyme under standard conditions. 25 units of Tn5 or TS-Tn5 transposase assembled with antibody-oligonucleotide conjugate were added to 1 ug of genomic MCF7 DNA in Tagment DNA buffer. The samples were incubated at 55° C. for 1 hour (C+ lanes only) or 37° C. for 1 to 3 hours. Half of the tagmented DNA was analyzed on a 1.5% agarose gel. C−, no transposase. Arrow denoted untagmented input DNA. Bracket denotes tagmented DNA fragments.

The ability of the antibody-tethered oligonucleotides to form a functional transposome was also determined. Activity was first tested at 55° C. for 30 min, the standard temperature for the Tn5 transposase, and also for longer durations at 37° C. (FIG. 13) due to concerns that elevated temperatures when applied to the TAM-ChIP procedure would destabilize antibody-chromatin interactions. Tagmentation of purified genomic DNA was detected at both temperatures. However, a portion of untagmented input DNA (arrow) remained in all conditions indicating that the tagmentation was incomplete. It was noted that less untagmented DNA remained in all TS-Tn5 reactions, suggesting that the TS-Tn5-transposome-antibody complex may be more robust than its Tn5 counterpart. However, it is not clear if the incomplete tagmentation reactions with the transposome-conjugates are due to reduced transposase activity, incomplete or incorrect assembly of the transposome complex or due to steric hindrance from being antibody-tethered. However, the residual activity is still sufficient for TAM-ChIP. Primary antibody targeting of the transposome-antibody conjugate to chromatin could overcome the decrease in random transposition activity through primary antibody mediated stabilization of the transposome/antibody/chromatin complex, which would effectively drive the reaction forward.

Figure 14:
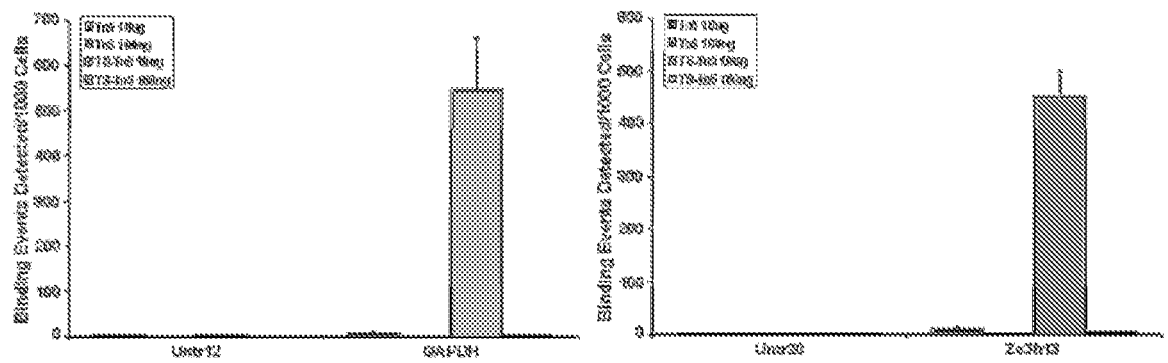
FIG. 14—shows Transposome-secondary antibody complex is directly to H3K4me3 antibody binding sites. The H3K4me3 primary antibody was incubated with 0.1 or 10 ug of chromatin overnight. Either the Tn5 or TS-Tn5 transposome-antibody conjugate was added at of 1:1 of primary antibody to secondary-transposome conjugate ratio), and incubated at 4 degrees for four hours to allow binding of the secondary antibody-transposome to the primary antibody. Samples were diluted four volumes of IP dilution buffer followed by one volume of tagmentation buffer containing $Mg^{2+}$ to activate the transposase and incubated at 37 degrees for 3 hours. The chromatin bound and tagmented by the transposomes was captured using Protein G agarose beads (Invitrogen) and eluted in buffer containing the reducing agent TCEP (Tris(2-carboxyethyl)phosphine hydrochloride) to sever the cleavable disulfide bond used to generate antibody-oligonucleotide conjugate. Proteins were removed by digestion with the protease Proteinase K and formaldehyde cross-links reversed as per established ChIP protocols. Half of the eluted DNA was subjected to 25 cycles of PCR using the approach illustrated in FIG. 2. PCR amplification products were purified using standard methods and diluted to 2 ng/ul. Quantitative PCR was performed using primers targeting the regions known to be negative (Untr12 and Untr20) or positive (GAPDH and Zc3h13) for H3K4me3 and 10 ng of DNA.

Data disclosed herein shows that the antibody-transposome construct could be directed to chromatin in a specific manner through a primary antibody that binds trimethyl-lysine at residue 4 of Histone H3 (H3K4me3), a post translation modification found in the promoter regions of transcriptionally active genes. FIG. 14 shows that, in the presence of 10 ug of chromatin, but not 0.1 μg, the TS-Tn5 transposome complex but not the Tn5 transposome complex effectively tagmented chromatin regions bound by the primary antibody. Further, the untranslated regions on chromosome 12 and 20, showed no enrichment, indicating no tagmentation by the transposase, confirming that the primary antibody was directing the transposase to chromatin fragments associated with antibody. Control reactions, lacking either the primary antibody or lacking the secondary transposome conjugate, showed no tagmentation in any of the regions analyzed. The no primary antibody control reaction confirms that tagmentation is driven solely by primary antibody binding events. The secondary antibody alone is unable to direct tagmentation of chromatin.

Figure 15:
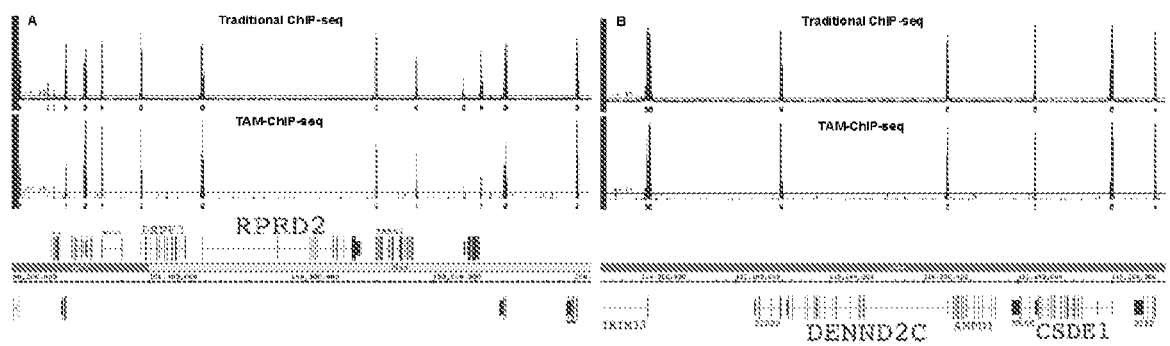
FIG. 15—NGS profile of the TAM-ChIP library relative to a traditional ChIP library. Traditional ChIP and TAM-ChIP was performed on 10 µg of MCF7 chromatin with 2 µg of H3K4me3 antibody. Libraries were prepared using standard protocols for the traditional library and as described in FIG. 6 for TAM-ChIP. The enriched DNA was sequenced on the Illumina MiSeq platform. Regions of enrichment from A, a 4 Mb region from chromosome 21, and B, a 3.05 Mb region from chromosome 13 are shown above.

Next generation sequencing data from normal ChIP and from TAM-ChIP was found to be nearly identical as shown in FIG. 15.

As stated above, transposon targeting can be achieved utilizing not only antibody-transposon targeting, but also targeting via protein-protein and/or protein-DNA interactions in which the transposon is conjugated to a protein that would target a protein-binding partner or protein-binding domain on the chromosome. Examples of such proteins include, without limitation, methyl-binding proteins, proteins containing the following domains: bZIP domain, DNA-binding domain, helix-loop-helix, helix-turn-helix, MG-box, leucine zipper, lexitropsin, nucleic acid simulations, zinc finger, histone methylases, recruitment proteins, Swi6. For example, conjugating a transposon onto MBD2, a protein that binds to the methyl group in DNA, would enable tagging chromatin DNA with the specific DNA code of the transposon where MBD2 binds-all methylated CpG binding sites (see Example 14). Similarly, binding domains, such as chromodomains [41], can be cloned into vectors and expressed in the appropriate cells to create GST-fusions proteins, which after purification can be conjugated to the Transposome using the methods described herein or known in the art. These complexes could then be isolated using a GST-binding resin. For example, using chromodomains from MPP8, CBX2, CBX7, ADD from ATRX and PWWP domain from DNMT3a would enable binding to H3K9me3, H3k27me3, H3K27me3, H3K9me3, and H3K36me3, respectively.

Transposon targeting can also be based on RNA-protein interactions, RNA-DNA interactions. For example, the TAM-CHIP methods described herein can be modified to work with Chirp and CHART. Given the similarities to ChIP it is possible to modify the TAM-ChIP protocol to work in Chirp and CHART procedures. The advantage of this approach would be in the simplification of the Chirp and CHART protocol since library generation occurs "automatically" using the transposase-targeted approach. A basic outline of how this would be achieved is listed below.

1. A series of modified (biotin, streptavidin or other attachment chemistry) oligonucleotides are designed to hybridize to the ncRNA of interest.
2. Formaldehyde fixed chromatin is prepared (similar to what is done for ChIP).
3. Oligonucleotides are hybridized to the native target within the chromatin prep.
4. Transposase enzymes preloaded with a sequencing library compatible transposon (similar to TAM-ChIP approach) and modified with a complimentary attachment chemistry are added to the material generated from Step 3 (above). These enzymes will bind to the complimentary chemistry on the hybridized oligos resulting in the intended targeting of the transposon to the sites of interest.
5. Following washing, magnesium is added to activate the transposase resulting in the integration of library adaptors to the sites of interest.
6. PCR amplification results in sequence-ready libraries
7. DNA is sequenced using Next-Gen sequencing platforms such as Illumina resulting in the genome-wide identification ncRNA interaction sites.
8. As an alternative to steps 3 and 4, the biotinylated or otherwise chemically modified oligos could be preincubated with the streptavidin or otherwise chemically modified transposase complex. This entire complex could then be hybridized to the chromatin sample.

METHODS AND REPRESENTATIVE EXAMPLES

Preferred methods, materials, and conditions for carrying out some preferred, non-limiting, representative embodiments of the invention are described below. Those of ordinary skill in the art will readily appreciate that the invention can be practiced in a number of additional embodiments using equivalent alternate techniques and materials.

Example 1: TAM-ChIP

Preliminary Data

Figure 4:
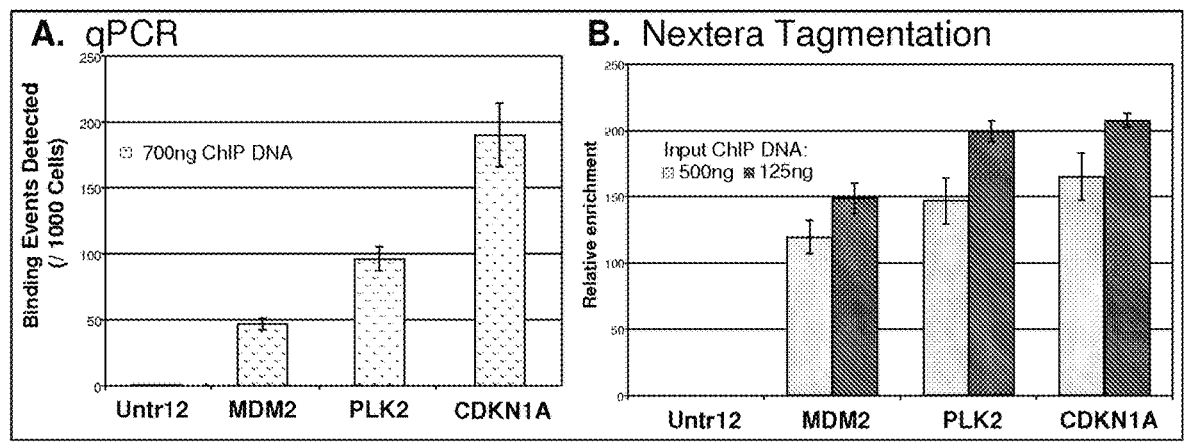
FIG. 4—shows an evaluation of Nextera Tagmentation in ChIP-Seq DNA Library Preparation. Q-PCR was used to detect enrichment of p53 binding sites in p53 immunoenriched chromatin from stimulated MCF7 human breast cancer cells.
Figure 5:
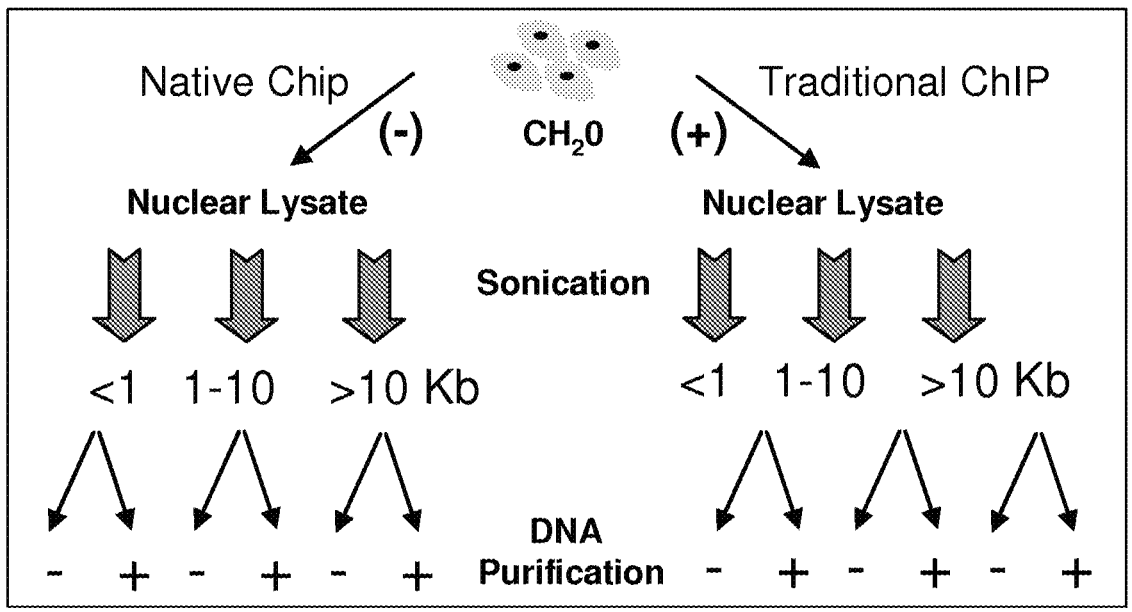
FIG. 5—shows a schematic of experiments following identification of EZ-Tn5 compatible ChIP cell lysis buffer FIG. 6—shows a schematic of conjugation scenarios FIG. 7—experiment sequence for optimal TA-ChIP methodology development FIG. 8—shows one approach for proximity ligation FIG. 9—shows a Schematic representation of Illumina-compatible sequencing library preparation generated by the Nextera Kit. Transposomes assembled with free ends appended with sequencing tags (a) are used in a tagmentation reaction to produce a 5'-tagged DNA fragment library. Limited-cycle PCR with a four-primer reaction (4pPCR) adds Illumina bridge PCR-compatible adaptor sequences (b). Optional barcoding/indexing (triangle) is incorporated into Adapter 2 (and optionally also Adapter 1) and added between the upstream bridge PCR adaptor and sequencing tag 2 (c). Features of the amplicons produced with comprise the NGS library. (Adapted from www.Epicentre.com)

In order to improve the turnaround-time of conventional ChIP-Seq services, Epicentre's Nextera™ DNA Sample Prep kit, which uses the EZ-Tn5 Transposome™ and suppression PCR to generate NGS compatible libraries, was evaluated for suitability for use with ChIP-enriched DNA. ChIP was performed in duplicate using p53 antibodies and 30 μg chromatin extracted from estrogen stimulated MCF-7 cells (a human breast cancer cell line) following established protocols, and isolated DNA was then purified. Quantitative PCR was performed on known p53 binding sites to validate the specificity of the anti-p53 ChIP reactions (FIG. 4, Panel A). Untr12 is a negative control in a gene desert on human chromosome 12 and is not expected to be bound by p53.

The Nextera transposition reaction was performed using two quantities of ChIP DNA (FIG. 4, Panel B) according to the manufacturer's protocol. The DNA libraries were purified and used for PCR according to the Nextera protocol for 18 cycles. The amplified DNA was purified and quantified by measuring absorbance at 260 nm (A260) using a Nano-Drop spectrophotometer. The amount of DNA produced in the Nextera reaction was in the range of what is typically obtained using the Illumina library protocol.

These data demonstrate the suitability of EZ-Tn5 for use with fragmented DNA substrates, and that the p53 binding sites detected in traditional ChIP are preserved and quantifiable in Nextera-generated libraries. Interestingly, a higher amount of DNA was generated in the Nextera reaction with the smaller amount of DNA isolated by ChIP, suggesting that the transposition efficiency was higher and that less input chromatin may be required for ChIP experiments when EZ-Tn5 is incorporated into the methodology.

For the methods described below, the EZ-Tn5 transposome is purchased from Epicentre Biotechnology (Madison, WI, USA) and ChIP-IT Express™ reagents and protocols are used (Active Motif, Carlsbad, CA, USA) as the ChIP reagents throughout this example. The end result is an optimized method for the ChIP-validated antibody-transposome conjugates.

The methods below are performed in human Hela cell lines, which are easily cultured in vitro to produce the necessary quantities of genomic DNA (gDNA) or chromatin required for the experiments described below. While many epigenetic research tools and consumables target researchers using vertebrate animal model systems, largely because this segment is the largest in the epigenetic research tools market, the principle epigenetic mechanisms are conserved throughout vertebrates (including the primary amino acid sequence of histones and the repertoire of post-translational modifications), although those skilled in the art will be able to adapt the reagents and methods of this invention for use with other organisms. Another compelling reason for the use of mammalian cells for the TAM-ChIP technology stems from the complexity of the genome. ChIP is far more challenging in mammalian cells, where genes represent only 1-1.5% of the genome, than in lower eukaryotes where genes represent a much large fraction of the total genome (compare with 70% in S. cerevisiae).

TABLE 2

Candidate HeLA genomic loci for qPCR analysis of transposition efficiency

| Transcriptionally Active | | | | |
|---|---|---|---|---|
| GAPDH | HOX10 | EEF1A1 | TUB1C | LDHA |
| RASSF 1A | ACTB | PPIB | PABPC1 | RPS18 |
| Transcriptionally Repressed | | | | |
| PTGER3 | HOXD13 | HBB | Untr12 | NGB |
| CFDP1 | Sat2A | MyoD | PAX2 | MYT1 |

Analytic Methods

The majority of the experiments described below require determination of transposition efficiency, and evaluation of the distribution (both abundance and range) of DNA fragments generated as a consequence of transposition. Transposition efficiency can be determined using any suitable technique, for example, by quantitative real-time PCR using a StepOnePlus RT-PCR thermocycler (Applied Biosystems) and primers complimentary to a panel of genomic loci known to be either transcriptionally active or repressed in Hela cells (Table 2, above) [25]. Transposition results in the insertion the biotin-tagged transposon oligonucleotide into the target DNA, enabling isolation of transposon-tagged DNA fragments with streptavidin-coated magnetic beads and subsequent quantitation in triplicate by real time PCR. A five-fold dilution series of fragmented Hela genomic DNA can be used as standards to generate a quantitation curve. Identical locus-specific PCR primer sets are used for both samples and standards, and transposition efficiency will be calculated as the median of the DNA recovered for all loci. The generation of tagged fragments less than about 200 bp is particularly preferred to achieve the necessary resolution of sequence reads in NGS applications. Evaluation of the abundance and range of transposon tagged-DNA fragment sizes produced by transposition events requires, for example, an Agilent 2100 Bioanalyzer, which employs a microfluidics system for electrophoretic determination of size and quantity of DNA fragments in sample volumes of 1-4 µl.

Example 2: Antibody-Transposase Conjugates

TAM-ChIP requires that the enzymatic activity of the transposase preferably be unaltered, with regards to catalytic rate and randomness of integration sites, when coupled to another protein. Conjugations with various chemistries and crosslinkers of varying length are compared using ChIP validated antibodies. This example generates functional antibody-transposome conjugates.

An extensive number of ChIP-validated antibodies are commercially available or can be developed using conventional antibody production techniques. Here, antibodies to a chromatin associated protein (RNA polymerase II) and a structural chromatin protein, a histone (anti-histone H3 trimethyl-lysine 4 (H3K4tm) mark associated with transcriptionally active chromatin), are conjugated to the EZ-Tn5 transposome using any suitable approach, two of which are described below.

Antibodies can be chemically crosslinked either to the transposase (protein-protein) or to the transposon (protein-DNA) using Hydralink Chemistry (Solulink, San Diego, CA, USA), which is stoichiometrically more efficient than traditional EDC/NHS chemistries and has been used in the development of PCR-based proximity ligation assays, recognized as the most sensitive assay for protein detection [26-28]. The chemistry involves formation of reaction between an aromatic hydrazine (hydrazinonicotinamide-HyNic) and an aromatic aldehyde (4-formylbenzamide-4FB), yielding a stable bis-arylhydrazone that is UV-traceable, absorbing at 350 nm. Conjugation reaction kinetics can be augmented 10-100 fold in the presence of aniline, leading to conjugation yields of >95%[26].

Figure 6:
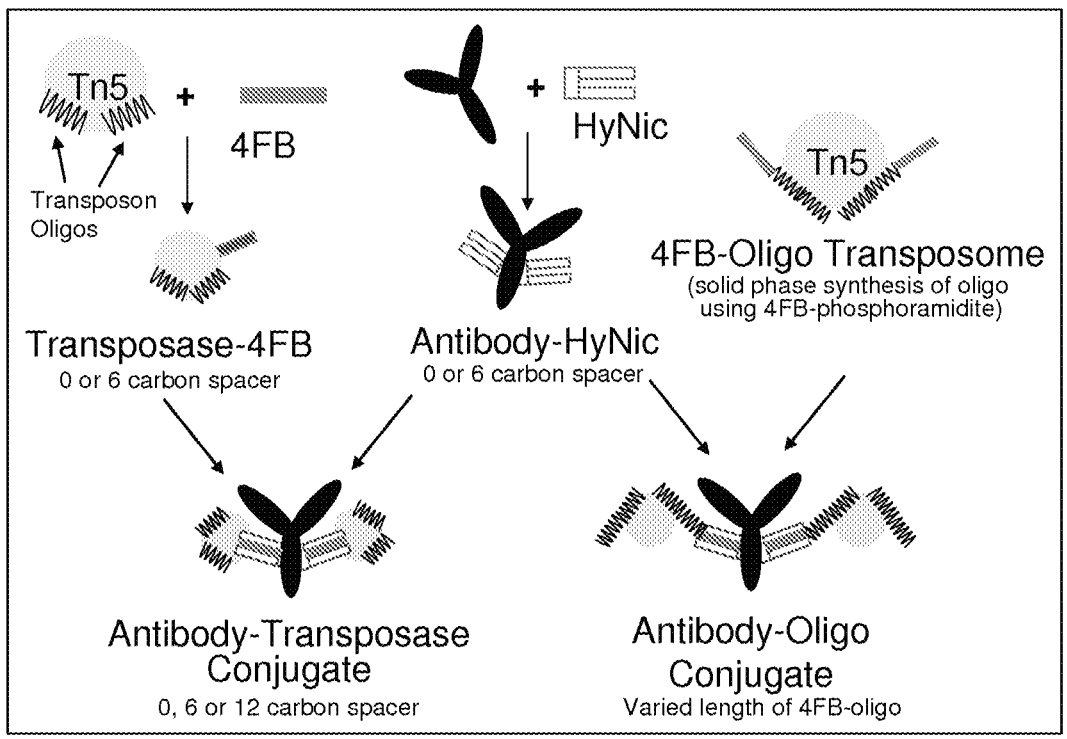

Conjugations are performed following the manufacturer's established protocols in quantities sufficient for their functional characterization described below and for their subsequent use in the methods described. Both antibody-transposase and antibody-transposon, the transposase-associated oligonucleotide (FIG. 6) conjugates is prepared using varying crosslinker lengths (0, 6 or 12 carbon side-chains) for protein-protein conjugates or transposon oligonucleotides of varying lengths (synthesized with additional 20, 40 or 60 bp), with the 4FB moiety incorporated during solid phase synthesis. Conjugate stoichiometry is determined by measuring absorption of the bis-arylhydrazone crosslinking product at 350 nm which has a molar extinction coefficient of 1600 M·1 [29]. Aliquots reserved at each step are used to monitor transposase activity by measuring transposition efficiency with lambda DNA (as above) and retained antibody recognition of antigen by dot blot analysis using established Active Motif protocols. This Example provides isolation of antibody-transposase conjugates with a stoichiometry of greater than or equal to two transposase molecules per antibody molecule in which the function of antibody and transposase is no less than 90% of their unconjugated counterparts. These conjugates are used below for the TAM-ChIP technology. Methods for conjugation of antibodies to a variety of molecules (enzymes, dyes, oligonucleotides, biotin) are well established and are considered routine. Tn5 transposase fusion proteins have been described and are functional [30, 31]. Accordingly, any suitable approach can be adapted for use in the context of this invention.

Example 3: TAM-ChIP Optimization

Examples 1 and 2 above provides the basis for performing TAM-ChIP and demonstrating its benefits relative to traditional ChIP methods. The optimized chromatin extraction and fragmentation procedure above is combined with the antibody-transposome conjugate to perform the TAM-ChIP procedure. A method of comparing the genomic representation of the sequencing libraries produced by TAM-ChIP and traditional ChIP-Seq is also provided. This is done using two steps. The first step involves optimizing sets of conditions with regards to chromatin and antibody-transposase concentrations, optimization of incubation times using transposition the analytic methods describe above as the readout. The second step is a direct comparison of the genomic representation of the DNA libraries produced by TAM-ChIP with that of conventional ChIP-Seq methods.

Figure 7:
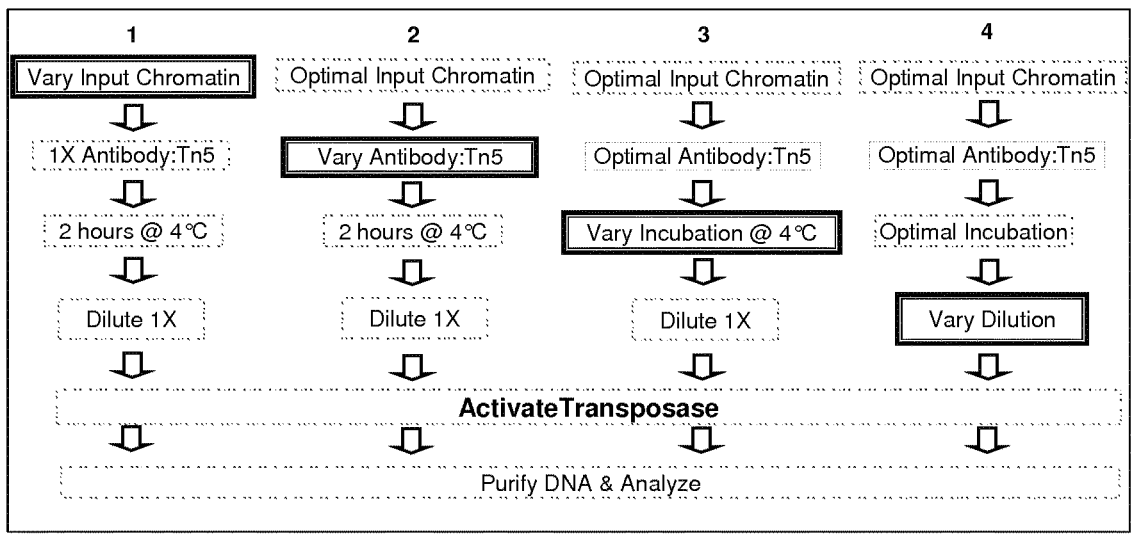

An optimal protocol can be determined using the steps depicted in FIG. 7. First, the optimal amount of chromatin substrate is determined, as this impacts both transposition efficiency and fragment size. Initially, antibody-transposase conjugates are used at a fixed amount, where in the amount of transposase enzyme present corresponds to the amount recommended in applications developed by Epicentre Biotechnology for use with 50 ng DNA.

Triplicate samples of 50, 150, and 450 ng of Hela cell chromatin (quantitated by A260) are incubated with the antibody-transposase conjugate in 100 IJI for two hours at 4° C. (FIG. 7, column 1). The chromatin-antibody complexes are diluted in LMW buffer and transposase activated by the addition of 10 mM Magnesium acetate using the optimized transposase reaction conditions developed above. Samples are treated with 201 µg Proteinase K for 1 hour at 37° C. and DNA purified using a Zymo DNA Clean & Concentrator-5 Kit (or equivalent). If formaldehyde crosslinked chromatin is used, prior to protease treatment, reversal of crosslinks is achieved by the addition of an equal volume of Reverse Cross-Linking Buffer (50 mM NaCl in 50 mM Glycine) and samples incubated at 95° C. for 15 min.

Biotin-tagged DNA fragments are captured using streptavidin magnetic beads and transposition efficiency and fragment size profiles are determined as described above. Transposition efficiency is significantly higher at the transcriptionally active genomic targets listed in Table 1 than at the transcriptionally silent regions that are analyzed by qPCR. Consequently, for these experiments transposition efficiency is calculated as a relative ratio of transposition into transcriptionally active and inactive regions, thereby providing a means for comparison of the specificity and efficacy of the antibody-transposome complexes. The range of input chromatin is expanded in subsequent experiments if transposition efficiencies are too low or tagged-DNA fragments too small, the latter a consequence of too little DNA. This set of experiments identifies the antibody-transposome conjugates with optimal activity for chromatin substrates and which chemistry is optimal for the generation of additional antibody-transposase conjugates, such as a non-immune IgG-transposase negative control required for the TAM-ChIP protocol described below.

The optimal conjugate for each of the two antibodies (RNA polymerase II and H3K4tm) is used in the following subsequent experiments (FIG. 7, columns 2 through 4) designed to optimize the effects of different antibody-transposase concentrations, antibody-chromatin incubation times, and sample dilution on transposition efficiency and fragment size. The conditions yielding optimal results are carried forward in the subsequent rounds of procedure optimization. Antibody-transposase concentrations are varied in a two-fold dilution series consisting of 2X, 1X and 0.5X; incubations of chromatin with antibody-transposase conjugates are varied for 0.5, 1, 2, and 4 hours; and sample dilution prior to transposase activation to ensure intracomplex transposition are varied as five-fold dilution series (1:X; 1:5X; 1:25X, and 1:125X, where X represents the minimal dilution factor determined using the methods described herein). The ranges of variables are expanded as warranted based on observed fragment size and transposition efficiency. These experiments identify the conditions which produce a minimum of 500 ng of <200 bp tagged-DNA fragments following 18 cycles of PCR-amounts required for the Illumina sequencing platform. These experiments result in an optimized TAM-ChIP methodology.

Example 4: Validation of NGS Libraries Generated by TAM-ChIP

The DNA libraries produced by the optimized method in developed in the preceding experiments with IgG, RNA polymerase II, and H3K4tm antibody-transposome conjugates are compared with the libraries produced via traditional ChIP-Seq performed with the same unconjugated antibodies. For traditional ChIP-Seq, Hela chromatin extracts generated for the above set of experiments are incubated with 5 µg antibody for 16 hours at 4° C. 1 µg are left unprocessed and serve as the input control. Antibody-chromatin complexes are captured using protein A coated magnetic beads, washed, eluted, and DNA purified following established procedures. ChIP with 5 µg of non-immune rabbit IgG is performed in parallel as an antibody specificity control. The ChIP-enriched and the untreated sonicated gDNA are processed according standard protocols for library preparation for sequencing in the Illumina Genome Analyzer GAll. This consists of end-repair, adaptor ligation, size-selection and PCR amplification, and all these steps are done and sequencing performed according to standard methods. The generated data from both TAM-ChIP and traditional ChIP from two independent experiments is analyzed. Reads mapped to the human genome (alignments) are analyzed to find genomic regions with significant enrichments ("peaks") over alignments obtained from either Input or IgG control DNA. Dozens of H3K4tm and RNA Polymerase II ChIP-Seq assays are performed and analyzed, and very similar results are obtained with the peak calling algorithms MACS [32], SICER [33], or CCAT[34]. In addition, software is used to extend the read alignments to the actual length of the DNA fragments (~200-250 bp), and to generate a "signal map" showing alignment ("tag") densities in 32-bp bins across the genome and reproducibility between replicates is typically ~80%. Peaks and signal maps are entered into gene annotation and sample comparison software, returning concise Excel tables showing peak metrics and location of peaks relative to genes. These are used to compare the representation of genomic sequences in the DNA libraries prepared by two methods and show concordance of genomic coverage.

Example 5: Additional TAM ChIP Embodiments

The methods established above will be recognized by those of ordinary skill in the art to be readily carried out in other embodiments, e.g., (a) those comprising antibodies from different animal hosts (rabbit, mouse, rat and goat) specific for proteins associated with either transcriptionally active euchromatin or transcriptionally silenced heterochromatin (i.e. HP1 proteins, and heterochromatin-associated histone marks), (b) TAM-ChIPs wherein antibody-transposase conjugates are be used singly or simultaneously, and with different degrees of complexity (two-plex, three-plex, etc.), including versions with each conjugate bearing a unique bar-code sequence for antibody identification, (c) those where the antibody-oligonucleotide conjugates prepared above are used in a multiple proximity ligation method (see, e.g., Example 6, below). Antibody-oligo conjugates bound to chromatin are diluted, followed by proximity ligation of the antibody-associated oligonucleotide with the associated chromatin fragment end and nicks sealed. Ligation of oligonucleotides to chromatin has been used to map chromatin higher order structures [35], where co-associating chromatin ends in isolated complexes containing higher-order structures are tagged via ligation with primers and then ligated to each other via their proximity, supporting the feasibility of this approach. Use of a reversible antibody-oligonucleotide crosslinking chemistry or the inclusion of a rare restriction endonuclease cleavage site allows liberation of the antibody from the DNA now tagged with the bar-code containing oligonucleotide which is then directly amplified for NGS using an appropriate PCR amplification strategy.

Example 6: Antibody-Oligonucleotide Conjugates and Proximity Ligation

Figure 8:
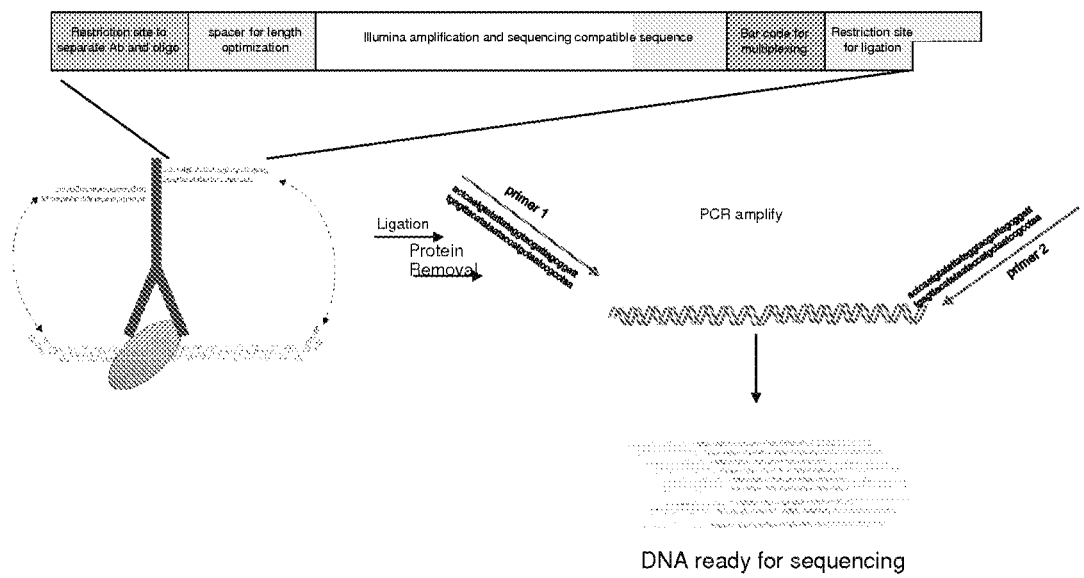

These methods use cross-linked and sonicated (or restriction digested) chromatin as a starting material. Instead of conjugation to transposase, this approach uses conjugation of an antibody to short double-stranded DNA oligonucleotides of known sequence. The conjugate is incubated with cross-linked chromatin that has been either restriction enzyme digested or sonicated, resulting in antibody binding at the intended target. Proximity-mediated ligation is performed, resulting in ligation of the antibody delivered oligos to the target-associated free genomic DNA ends (FIG. 8). Digestion of the cross-linked chromatin and the proximity ligation strategy using sonicated or restriction enzyme digested cross-linked chromatin is well established, and these methods build upon and inventively improve on those used in the 5C and Hi-C technologies (Dostie and Dekker, 2007; Lieberman-Aiden et al., 2009). The key to the ligation is to perform this step under diluted conditions which favor the interaction of DNA molecules held in close proximity. Following ligation, crosslinks can be reversed by heating to 65° C. overnight, and proteins can be removed with proteinase K treatment. The regions of interest (e.g., the regions bound by the protein of interest and targeted by the antibody) can be enriched by PCR using primers that anneal to regions within the ligated oligonucleotide sequence, and the resulting amplified DNA can be sequenced using, for example, the Illumina platform, resulting in a genome wide protein binding profile. In addition, this approach is well suited to generate binding profiles of multiple factors in the same sample. This is achieved by designing multiple oligonucleotides, each containing a unique bar code sequence, and conjugating these unique oligos to different antibodies. Multiple antibody conjugates can be added to the same sample at the same time. After sequencing, the data for the multiple targets can be sorted based on the bar code sequence.

Oligonucleotide Embodiments.

Several features can be designed into the oligonucleotide(s) that are conjugated to the antibody(ies). These features are listed below and depicted in FIG. 8.

1. The oligonucleotide is double-stranded and the 5' end of one of the strands is linked to biotin (or a member of different high affinity binding pair). The biotin is used for conjugation to the antibody.

2. There is a restriction site (e.g., Not 1, a "freeing" restriction enzyme in the context of the invention) encoded in each oligonucleotide to allow the oligonucleotide to be separated from the antibody, if needed.

3. There is a region of sequence included that functions only for the purpose of varying the oligonucleotide length. The ligation of the oligonucleotide to the free genomic ends of the captured DNA may be dependent on the length of the oligonucleotides. The entire oligonucleotide is typically about 80 nucleotides in length, although longer or shorter lengths may be optimal in a given application.

4. A region is included that is complementary to Illumina (or other suitable) primers. This region facilitates amplification of oligonucleotide-ligated genomic DNA, preferably to be compatible with sequencing on the intended (e.g., Illumina) platform.

5. There is a 4-base pair (or shorter or longer) barcode. Several different oligonucleotides can be synthesized, each having a different bar code. Oligos with different bar codes can be conjugated to different antibodies, thus allowing multiple antibodies to be used in the same reaction.

6. There is a restriction-site-compatible overhang that allows the oligonucleotide to be ligated to restriction-digested genomic DNA. The overhang may preferably be a 4 nucleotide overhang (e.g., GATC, which is compatible with Dpn II, Mbo I, and Sau3A I, digestions). In such cases, the genomic DNA is cut with a restriction enzyme that having a 4 bp recognition site, which should on average cleave the DNA every 256 bases. Alternatively, a combination of restriction enzymes having 6 bp recognition sites can be used. Alternatively, TA cloning can be used. In such embodiments, sonicated DNA is used which has gone through end repair and A overhang addition. The oligonucleotides are designed to have T overhangs.

Example 7: Alternate Antibody/Oligonucleotide Conjugation Embodiments

Any suitable chemistry can be used to achieve the antibody/oligonucleotide conjugations used in this invention. One such approach is described below.

1) The biotinylated forward strand oligonucleotide is annealed to the unbiotinylated reverse strand using standard procedures.

2) The antibody can be biotinylated using a number of available kits, for example, the Solulink Chromalink One- Shot biotinylation kit, which allows for quantitation of the number of biotins per antibody and thus allows for optimization of the number of biotins conjugated to the antibody. 3) Self-assembly of the conjugate can be achieved by mixing appropriate ratios of the biotinylated oligo, biotinylated antibody, and free streptavidin, a tetra mer with four biotin binding sites all of which can be simultaneously occupied. 4) Unconjugated antibody and oligo can be removed using streptavidin magnetic beads.

Figure 36:
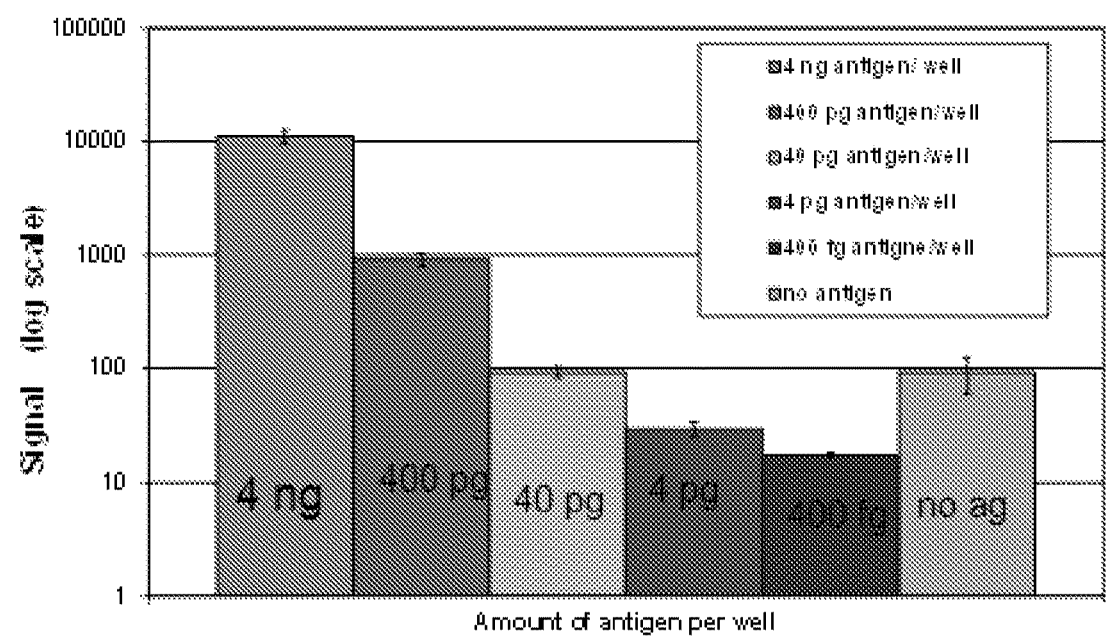
FIG. 36—Detection of goat antibody using immunoPCR. Detection antibody is oligonucleotide conjugated anti-goat IgG.

This approach has been used and validated using a ratio of 2:1:2 (oligo: free streptavidin:antibody). An anti-Goat IgG antibody was coupled to a 100 bp oligo by mixing in the presence of free streptavidin. A goat antibody serves as the antigen and was absorbed to maxisorp 96-well plates at different concentrations. The antibody/oligonucleotide conjugate was allowed to bind the antigen and excess antibody was washed away. After washing, signal was detected using PCR with primers that anneal within the conjugated oligonucleotide (FIG. 36).

Additional Examples

Figure 16:
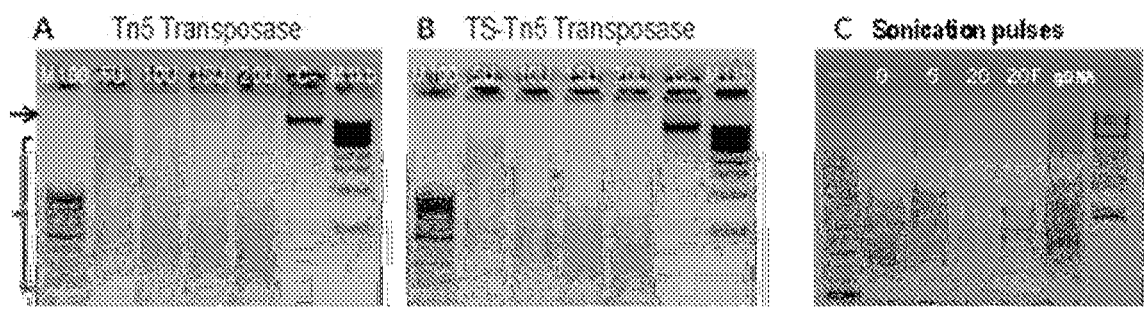
FIG. 16—shows Tn5 Transposase activity on Hela DNA and chromatin. Illumina Tagment DNA buffer and Tn5 (A) or TS-Tn5 (B) transposase, ranging from 5 to 20 Units, were added to HeLa DNA. The samples were incubated at 55° C. for 5 minutes and allowed to cool to 10° C. One fourth of the tagmented DNA was analyzed on a 1.5% agarose gel. C−, DNA with no transposase added. kb.C.Tagmentation of Hela chromatin DNA. 25 Units of Tn5 transposome was added to 10 µg of crosslinked HeLa chromatin sonicated to varying extents. Tagmented chromatin was treated with RnaseA and Protein K and crosslinks reversed followed by purification. For the lane marked 20F, tagmentation products were first passed through a size exclusion spin column to remove low molecular weight DNA fragments and primers as well as salts and other impurities that could impede with the downstream PCR reaction. 100 ng of tagmented DNA was subjected to 15 cycles of PCR and one fifth of the PCR reaction volume was analyzed on a 1.5% agarose gel. gDNA=Naked genomic DNA subjected to tagmentation, purification and 100 ng of the purified product subjected to subsequent PCR amplification. MW markers: lowest band in M100=100 bp; Lowest band on M1kb=0.5 kB. next band=1. Arrow denotes position of input, untagemented DNA. Bracket denotes migration smear of randomly tagmented DNA fragments of varying sizes.

Example 8—Compatibility of Chromatin Extraction Buffers with the Transposase Enzyme and Determination of Whether Chromatin is Recognized as a Tn5 Transposase Substrate For this analysis two forms of the Tn5 enzyme were used. One form of the enzyme was the same as that sold in the Nextera kit (Tn5) while the second (TS-Tn5) was a temperature stable variant under development by Illumina. FIG. 16 shows that assembled enzyme:oligonucleotide complexes (Panel A, Tn5, Panel B, TS-Tn5) completely tagment purified genomic DNA from HeLa cells (human cervical carcinoma), a cell line routinely used in ChIP experiments. Buffer compatibility experiments established that relative to the reaction buffer provided in the Nextera kit, both transposase enzymes retained full activity in chromatin extraction buffers.

Figure 17:
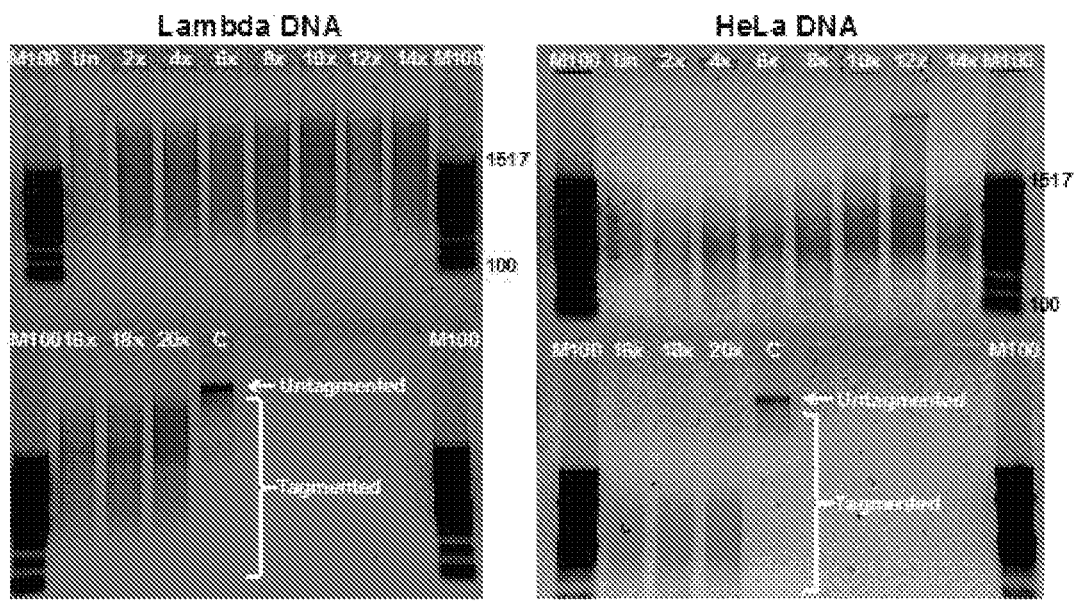
FIG. 17—Transposase efficiency on Lambda DNA and genomic HeLa DNA in 2 fold dilutions of ChIP buffer. Varying dilutions of ChIP lysis buffer containing either Lambda or genomic HeLa DNA were mixed with an equal volume of 2X Tagment DNA buffer and the Tn5 enzyme (Nextera Kit). Samples were incubated at 55° C. for 5 minutes, then cooled to 10° C. Tagmented DNA was purified and eluted in 25 µl. One fifth of the eluted DNA was analyzed on a 1% agarose gel. Un, undiluted ChIP buffer; C, DNA with no transposase added. M100, a 100 bp molecular weight DNA ladder.

Example 9—Identify the Minimum Dilution Factor with Which the Antibody-Chromatin Complex Must be Diluted Such that Transposase Efficiency is Unaffected The lysis buffer used to extract chromatin from cells for the ChIP method contains harsh detergents such as SDS (for efficient extraction) and EDTA (to inhibit nuclease activity). In TAM-ChIP, antibody-transposase complexes are directly added to chromatin in lysis buffer. Initial experiments were aimed at determining the minimum dilution factor of the chromatin in lysis buffer required to preserve full transposase activity is retained. A mock-ChIP experiment using Active Motif's ChIP lysis buffer was performed to reproduce the buffer composition present at the chromatin immunocapture step. This buffer was sequentially diluted two fold (ranging from undiluted to a 1:20 dilution) into sterile water. Transposase was added to each buffer dilution with either 50 ng of unmethylated lambda phage DNA (48.5 kb, Promega) or 1 μg of genomic HeLa DNA. FIG. 17 shows the heterogeneous population of DNA fragments produced by the random activity of the transposase which appears as a smear following agarose gel electrophoresis. The enzyme "tagmented" (defined as fragmentation of substrate DNA fragment through the cutting and insertion of appended-end oligonucleotides by the transposase) both DNA templates equally well, even in undiluted chromatin extraction buffer conditions. These data indicate that the chromatin extraction buffer does not inhibit the transposase and that no dilution of the chromatin will be needed at this step of the TAM-ChIP procedure. Thus, alteration or optimization of chromatin extraction buffer formulation is not required. We observed that the range of fragment sizes produced by the transposase differed for the two DNA templates. Lambda DNA generated higher molecular weight fragments relative to HeLa DNA. Consequently, use of the Lambda DNA as a reference DNA or positive control was discontinued for subsequent experiments. It was felt that HeLa genomic DNA would serve as a more relevant control for subsequent experiments where chromatin is used.

Figure 19:
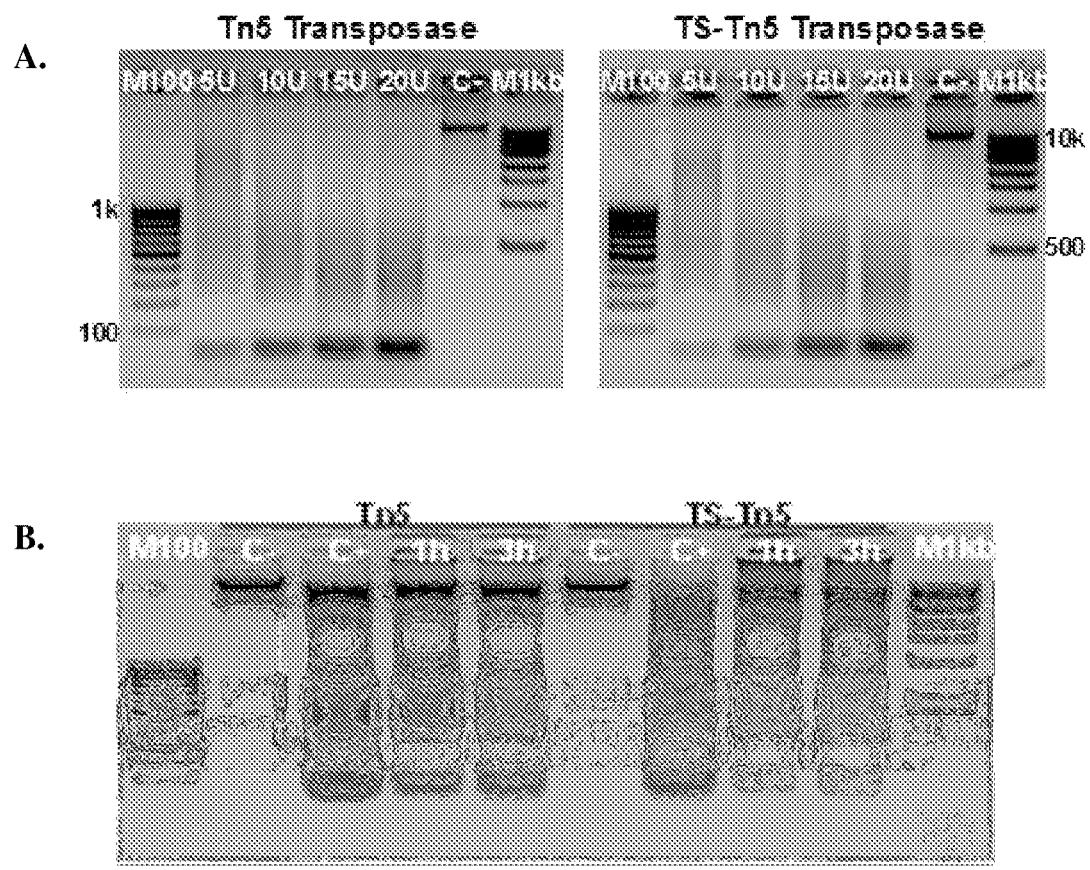
FIG. 19 (A). Activity of in house assembled Tn5 and TS-Tn5 Transposomes on genomic HeLa DNA. Illumina Tagment DNA buffer and Tn5 or TS-Tn5 transposomes (A+B), ranging from 5 to 20 Units, were added to HeLa DNA. The samples were incubated at 55° C. for 5 minutes and then allowed to cool to 10° C. One fourth of the tagmented DNA was analyzed on a 1.5% agarose gel. C−, DNA with no transposase added. MW markers: lowest band in M100=100 bp; Lowest band on M1kb=0.5 kB, next band=1 kb (B) Comparison of fragmentation of genomic DNA by Tn5 and TS-Tn5 transposome-antibody conjugates at different temperatures and free Tn5 enzyme under standard conditions. 25 units of Tn5 or TS-Tn5 transposase assembled with antibody-oligonucleotide conjugate were added to 1 ug of genomic MCF7 DNA in Tagment DNA buffer. The samples were incubated at 55° C. for 1 hour (C+ lanes only) or 37° C. for 1 to 3 hours. Half of the tagmented DNA was analyzed on a 1.5% agarose gel. C−, no transposase. Arrow denoted untagmented input DNA. Bracket denotes tagmented DNA fragments.

Example 10—Confirm Activity of Custom-Order Tn5 and TS-Tn5 Transposome Complexes Applicant manufactures all buffers, and reagents as part of its development process. To confirm that the efficiency of the transposase tagmentation reaction was equivalent with the use of Applicant's components compared to those provided in the Illumina Nextera kits. A-METS and B-METS oligonucleotides corresponding to the Illumina sequences were ordered (IDT, Inc.) and were annealed to p-MENTS (FIG. 18) to form the double stranded DNA (with appended ends) as the transposase will only bind its recognition sequence in the context of double-stranded DNA. Equal ratios of single-stranded oligonucleotides A- or B-METS together with p-MENTS were incubated at 98° C. for two minutes followed by 60 cycles of decreasing temperature of 1.3° C. per cycle. The concentration of the annealed oligonucleotides was determined on a Nanodrop spectrophotometer. The annealed oligonucleotides were analyzed on a 3% agarose gel to ensure complete annealing. Next, transposomes were assembled using both Tn5 and TS-Tn5 enzymes and the annealed oligonucleotides. Assembly occurs spontaneously in a one-hour incubation at room temperature at a 1:1 molar ratio. To confirm that these transposome complexes generated in house would tagment the DNA with the same efficiency as the EZ-Tn5 product provided in the Nextera DNA sample preparation kit (used in FIG. 18), varying amounts of Tn5 and TS-Tn5 transposomes were incubated with 1 μg of genomic HeLa DNA for 5 minutes at 55° C. and 250 ng of the tagmented DNA were analyzed on a 1.5% agarose gel. The efficiency of the newly assembled transposome complexes on genomic HeLa DNA was confirmed, with increased amount of enzyme resulting in increased tagmentation (FIG. 19), producing a larger population of DNA fragments of smaller size.

Figure 20:
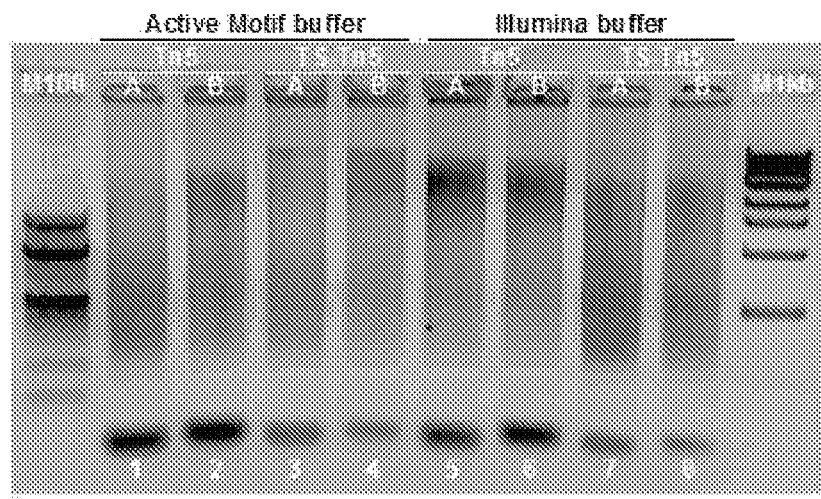
FIG. 20—Comparison of Illumina's and Applicant's tagmentation buffers. Activity of in house assembled Tn5 and TS-Tn5 transposomes on genomic HeLa DNA was determined using either a 5X Tagment buffer (lanes 1-4) made by Applicant with the 2X Illumina Tagment DNA buffer (lanes 5-8), and 5 units of Tn5 or TS-Tn5 transposomes assembled with either double stranded A-METS only or B-METS only (indicated as A or B), to genomic HeLa DNA. The samples were incubated at 55° C. for 5 minutes and then cooled to 10° C. One fourth of the tagmented DNA was analyzed on a 1.5% agarose gel.

FIG. 20 shows that Applicant's tagmentation buffer performed as well as the Illumina buffer provided in the Nextera DNA sample preparation kit.

Figure 21:
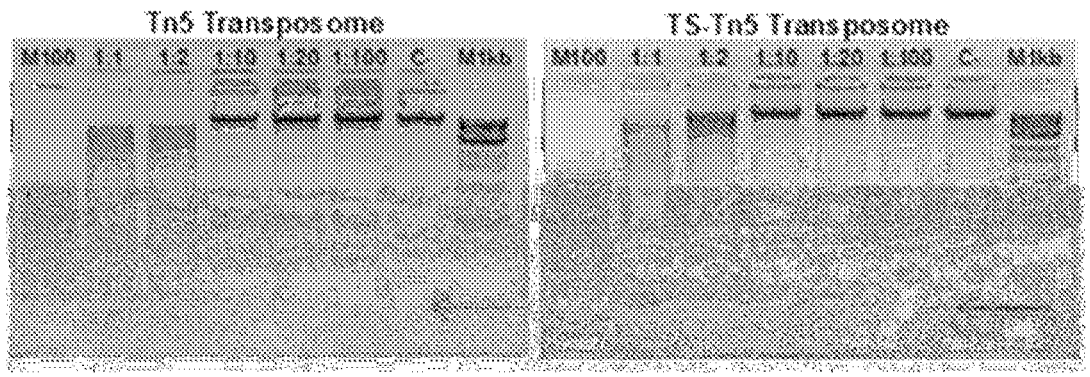
FIG. 21—Effect of varied oligonucleotide:Transposase ratios on transposome activity. Varying amounts of Tn5 and TS-Tn5 transposase were incubated with double stranded oligos at ratios ranging from 1:1 to 1:100. Tagment DNA buffer was added with 5 units enzyme to genomic HeLa DNA and incubated at 55° C. for 5 minutes and then reactions cooled to 10° C. One fourth of the tagmented DNA was analyzed on a 1.5% agarose gel. Arrows denote migration of free oligonucleotides.

It was noted that unintegrated oligonucleotides were visible in the agarose gels in FIGS. 19A and 20, raising concern that either not all enzyme was loaded with oligos or that the free oligonucleotides could interfere with transposase activity. To address these concerns, Tn5 and TS-Tn5 transposases were assembled with double stranded oligonucleotides with increasing amounts of enzyme, with ratios ranging from 1:1 to 1:100 (oligonucleotide:transposase) and tagmentation reactions preformed with genomic HeLa DNA were visualized on a 1.5% agarose gel (FIG. 21). While increasing amounts of enzyme did decrease the amount of free oligonucleotide, decreased tagmentation was detected at ratios of 1:10 to 1:100. Ratios of 1:1 and 1:2 were the most effective in tagmentation as judged by the absence of high molecular weight input DNA in these conditions, indicating that high concentrations of oligonucleotide are required to drive efficient transposome assembly. 1:1 ratios were adopted as the standard condition for subsequent experiments.

Figure 9:
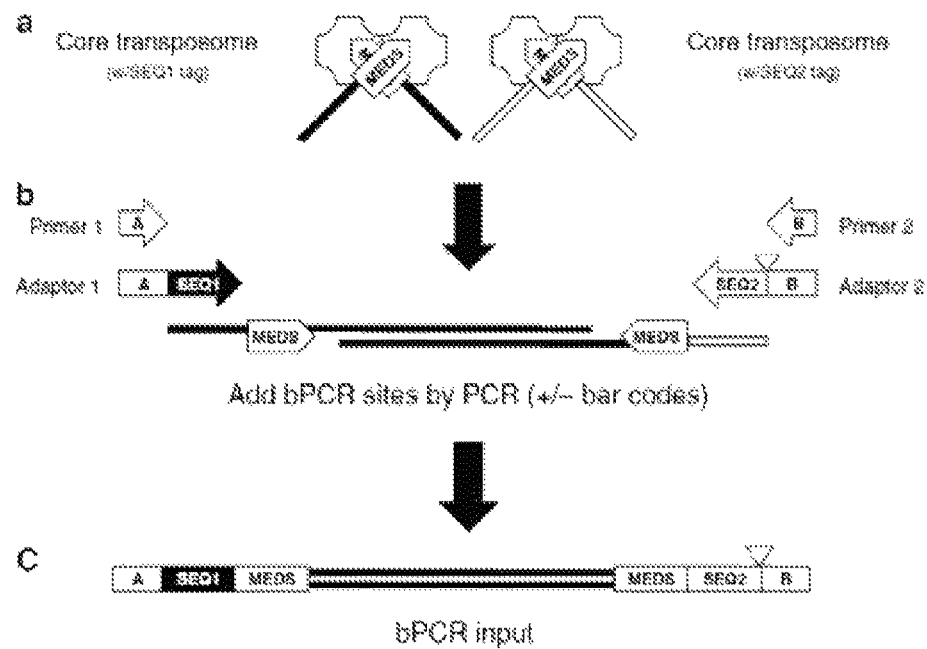

The Illumina sequencing platform requires the addition of index primers containing bar-code sequences as well as other platform-specific features to the tagmentation reaction products. These bar-codes allow for of up to 96 distinct samples to be sequenced simultaneously. These primers are added followed by a limited-cycle four-primer PCR reaction, the result of which are fragments that serve as input material for bridge PCR which generates the sequencing ready DNA library (FIG. 9). Since TAM-ChIP technology also relies on the barcoding strategy to achieve multiplexing capability, Applicants created new customized adapter and primer sequences compatible with the Illumina oligonucleotide sequences (A-METS and B-METS) and the Illumina sequencing platforms (Table 3).

TABLE 3

Adapter and Primer sequences for limited-cycle PCR

| Name | Sequence |
|---|---|
| Adapter 1a SEQ ID NO: 1 | 5'-AATGATACGGCGACCACCGAGATCTTAAGGCGAT CGTCGGCAGCGTC-3' |
| Adapter 2A SEQ ID NO: 2 | 5'-CAAGCAGAAGACGGCATACGAGATCGGTCTGTCT CGTGGGCTCGG-3' |
| Adapter 1b SEQ ID NO: 3 | 5'-AATGATACGGCGACCACCGAGATCTACACTCGTC GGCAGCGTC-3' |
| Adapter 2b SEQ ID NO: 4 | 5'-CAAGCAGAAGACGGCATACGATAGATCGCGTCTC GTGGGCTCGG-3' |
| Primer 1 SEQ ID NO: 5 | 5'-AATGATACGGCGACCACCGA-3' |
| Primer 2 SEQ ID NO: 6 | 5'-CAAGCAGAAGACGGCATACGA-3' |

Figure 22:
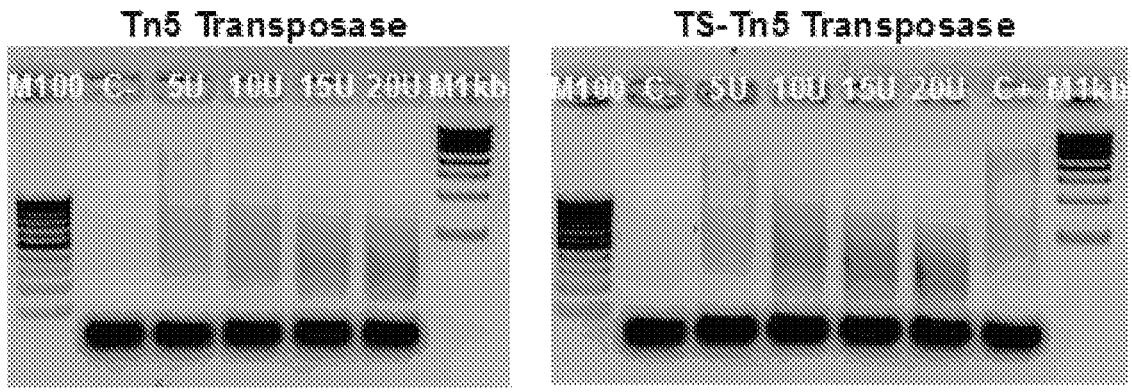
FIG. 22 Compatibility of tagmented DNA produced with in house transposomes with the Associated Nextera Index kit. Limited-cycle bridge PCR (5 cycles), using the Associated Nextera Index kit adapters and primers, on 100 ng of DNA, tagmented by the in house generated Tn5 and TS-Tn5 transposomes. One fifth of the PCR amplification was analyzed on a 1.5% agarose gel. C+ indicates genomic HeLa DNA tagmented by the Tn5 transposome. C− indicates no added transposome.

To test the compatibility of the in house designed oligonucleotides assembled into transposomes with the Illumina Associated Nextera Index kit, 100 ng of genomic DNA was tagmented by the in house assembled Tn5 and TS-Tn5 transposome complexes, and subjected to limited-cycle PCR using the four primers provided in the Illumina kit. FIG. 22 illustrates the successful amplification of the tagmented genomic HeLa DNA with the Nextera Index kit primers indicating compatibility between the various primers. Further, by increasing the amount of transposomes we were able to obtain a population of smaller fragment sizes. Note however, that the DNA fragments are largely >200 bp in length which may reflect a spacing limitation of the transposase enzyme.

Figure 23:
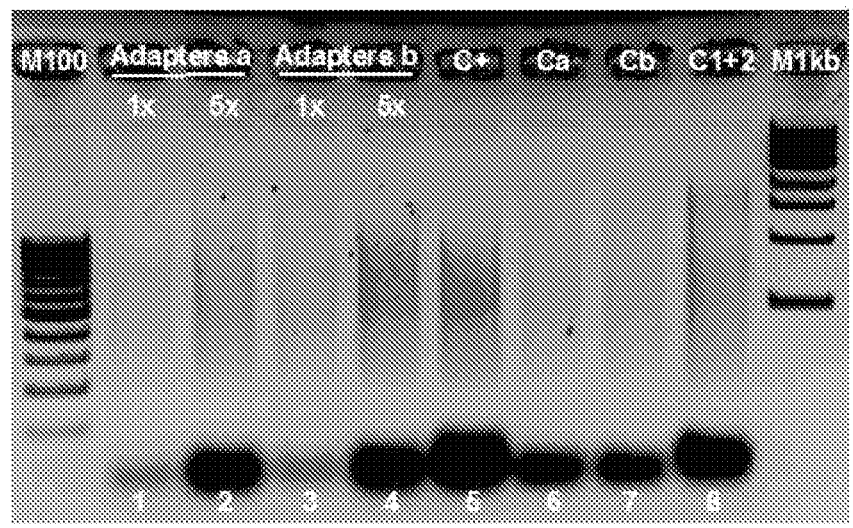
FIG. 23 shows Limited PCR of Tn5 tagmented genomic HeLa DNA with different combinations of Illumina and Applicant's primers and adapters. One fifth of each PCR reaction was run on a 1.5% agarose gel. 1X indicates 10 µM of Applicant's Primer 1+2 and 0.5 µM of each Adapter. 5X corresponds to 50 µM of Primer 1+2 and 2.5 µM of each Adapter. Lane 1 and 2: Applicant Adapter 1a and 2a plus Primer 1 and 2, Table 1. Lane 3 and 4: Applicant Adapter 1b and 2b plus Primer 1 and 2, Table 3. Lane 4 (C+): Illumina's Nextera Primer Cocktail (Primer 1 and 2, FIG. 19) and Index 1 and 2 adapters (Adapter 1 and 2, FIG. 19). Lane 5 (Ca): Nextera Primer Cocktail and Applicant's Adapters 1 and 2a (1×). Lane 6 (Cb): Nextera Primer Cocktail+Applicant's Adapters 1 and 2b (1×). Lane 7 (C1+2): Applicant's Primer 1+2 mix (1×) and Illumina's Index 1 and 2 Adapters. Unincorporated primers and adapters are visualized as the band at the bottom of the gel, increasing in intensity with increased amounts of primers and adapters.

Since the primers listed in Table 3 were based on sequences deduced form the literature and not provided by Illumina, the next experiment was performed to validate this set of in house primers. Two different versions of adapters 1 and 2 (called a and b) were synthesized (IDT, Inc). Different combinations of the primers and adapters provided by Illumina and the primers and adapters made by Applicant were used in PCR amplification of 100 ng tagmented genomic HeLa DNA. As depicted in FIG. 23, the different combinations of the of the new adapters at the 5X concentration (2.5 µM of Adapters 1a and 2a, or 1b and 2b) together with the new primers (50 µM of Primers 1 and 2) yield the same amplification as the PCR sample containing only the adapters and primers provided in the Illumina kit (FIG. 23, lane designated C+). Together these results confirm that oligonucleotides listed in Table 3 are functional, compatible with the Illumina Associated Nextera Index kit and therefore suitable for sequencing on the Illumina platform. In subsequent experiments where the four primer PCR reaction is performed, the 1b and 2b Adaptors are used at 2.5 µM with 50µM of Primers 1 and 2.

Figure 24:
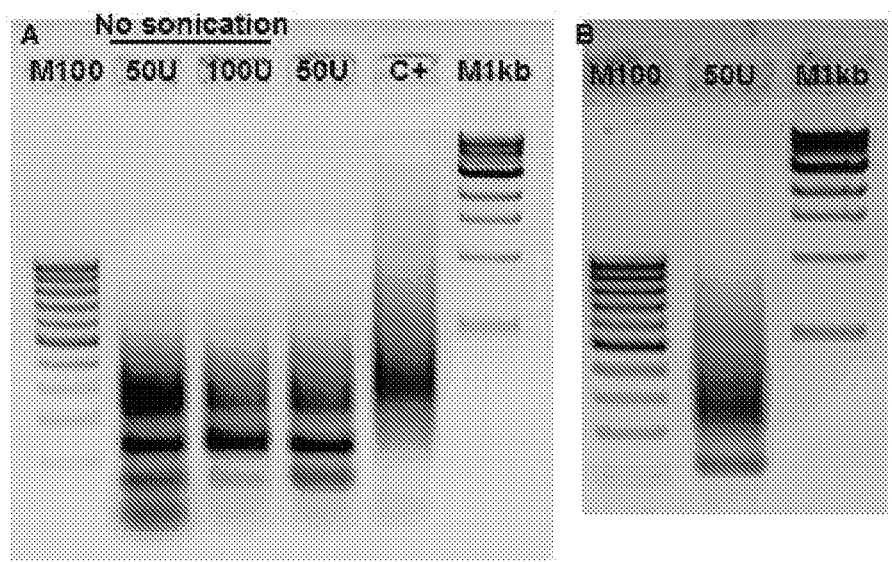
FIG. 24—Tn5 Transposase tagmentation activity on crosslinked HeLa chromatin. Tagment DNA buffer and Tn5 transposome, ranging from 50 to 100 Units, were added to 10 µg of crosslinked HeLa chromatin. The samples were incubated at 55° C. for 5 then cooled to 10° C. The tagmented chromatin was treated with RnaseA and Protein K and crosslinks reversed followed by DNA purification. 100 ng of tagmented DNA was subjected to 25 cycles of PCR. A. Half of the PCR was analyzed on a 1.5% agarose gel. C+ indicates tagmented genomic HeLa DNA. B. The remaining half of the PCR sample from lane one was purified using Agencourt AMPure XP magnetic beads to remove un-integrated adapters and primers and 500 ng of the PCR run on a 1.5% agarose gel.

Example 11—Confirm Activity of Tn5 and TS-Tn5 Transposome Complexes on Chromatin With Tn5 and TS-Tn5 activity on naked genomic DNA confirmed, the next set of experiments were aimed at verifying the activity of the Tn5 and TS-Tn5 transposases on chromatin. Formaldehyde crosslinked HeLa chromatin was mechanically sheared with Applicant's EpiShear Probe Sonicator with a cooled platform to generate chromatin fragments of less than 1 kb as per traditional ChIP protocols. 10 µg of chromatin was incubated with different amounts of Tn5 and TS-Tn5 transposome complexes. Initial experiments were performed with transposome concentrations ranging between 5 and 20 units, amounts of enzyme sufficient to tagment purified genomic DNA (data not shown). However, no or very low levels of tagmentation was detected with these amounts of enzyme when the reaction products were analyzed by agarose gel electrophoresis. These results suggested that the efficiency of the transposase on crosslinked chromatin is significantly lower, so higher enzyme amounts were used in subsequent experiments. Up to 100 units were utilized, and reaction products amplified by limited cycle PCR prior to agarose gel electrophoresis. In order to detect any tagmentation of chromatin, the number of limited cycle PCR cycles was increased from 5 to 25, and half of the PCR reaction resolved on the agarose gel (FIG. 24A). The remaining half was purified using Agencourt AMPure XP magnetic beads to remove un-integrated adapters and primers and 500 ng resolved by agarose gel electrophoresis (FIG. 24B). This material represents a DNA library suitable for use in NGS. Note in FIG. 24A that tagmentation of chromatin was successful in both unsheared and sheared conditions. It had been assumed that unsheared genomic DNA was too viscous for effective in vitro manipulations. However these results indicate that the transposome complex is able to tagment even unsheared chromatin. Further, the majority of fragments in the population range between 200-300 bp in length (Compare fragment sizes in FIG. 24 with those in FIG. 22), an ideal size for NGS library construction).

The above data establish that the transposase enzyme retains function in the buffers that are used to extract chromatin from the nuclei of mammalian cells and that both naked DNA and formaldehyde-crosslinked chromatin do indeed serve as substrates, albeit the latter with significantly reduced efficiency. In addition, in house generated tagmentation buffer, assembled transposomes and PCR primers for downstream library amplification appear functionally as robust as reagents provided in the Illumina products.

Relative to pure DNA, tagmentation of chromatin does require more enzyme; however, the end product—the range of DNA fragment size generated—are essentially identical (compare FIGS. 22 and 24). Interestingly the size of the starting chromatin (whether fragmented by sonication or intact) did not impact enzyme efficiency, an unanticipated result that will translate into a shortened the TAM-ChIP procedure. This result is suggestive that crude cell lysates containing chromatin, rather than isolated chromatin could be used as transposase substrates.

DNA fragments of less than 200 bp in length are typically used in the traditional method of NGS library preparation where DNA fragments of 100-200 bp in length are excised from an agarose gel. In all of the data shown above, whether chromatin or purified genome DNA was used a substrate, the majority of the fragments produced were larger, in the 200-300 bp range. This product range was also observed in positive control samples where only Nextera kit reagents were used. This fragment size may represent threshold for Tn5 when presented with larger DNA (1 kb or larger) substrates. The fragment sizes produced through tagmentation are still very suitable for use in NGS sequencing. While the larger fragment size could impact resolution of the sequencing reads, this could be compensated for by the randomness of the Tn5 mediated insertion events, and could result in adequate genomic coverage.

Example 12—Development of Antibody-Transposome Conjugates

Development of TAM-ChIP requires that the enzymatic activity of the transposase is retained, with regards to catalytic rate and randomness of integration sites, when coupled to an anti-rabbit secondary antibody (Jackson ImmunoResearch Laboratories Inc), as the conjugation partner (FIG. 11). Such a conjugate would be useful as a common reagent that can be used for all rabbit antibodies with diverse specificities (histone marks associated with open or closed chromatin, DNA damage, etc.)

Optimal Ratio of Primary to Secondary Antibodies.

Figure 25:
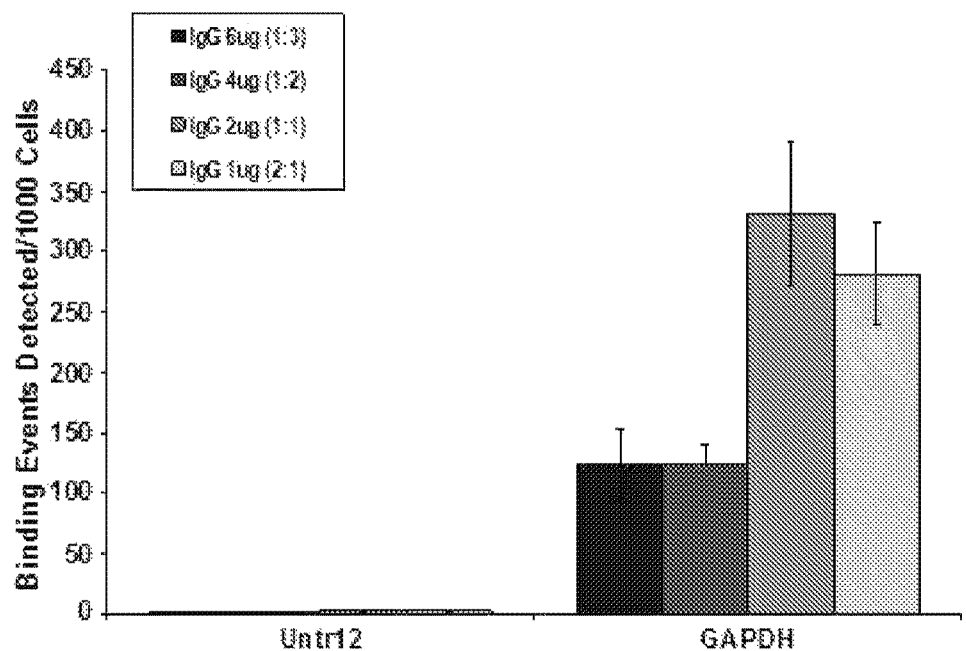
FIG. 25—shows optimal ratio of primary versus secondary antibody in ChIP. 10 μg of MCF7 crosslinked chromatin was used in ChIP for immunoprecipitation with 2 ug of H3K4me3 antibody and varying amounts of secondary IgG. The antibody bound chromatin was captured with Protein G agarose beads and subjected to Proteinase K treatment and reversal of crosslinks. 5% of the eluted IP was used for qPCR analysis with primers against Untr12 and GAPDH.

In many applications secondary antibodies are used in excess of the primary and multiple secondary antibody molecules can bind a single primary antibody molecule, thereby providing signal amplification. However, these conditions may or may not be ideal for TAM-ChIP. Initial experiments were focused on establishing the optimal ratio of primary to secondary antibodies using quantitative PCR of captured DNA as the analytical method. Chromatin was prepared essentially as described herein and Applicant's ChIP validated rabbit polyclonal specific for trimethyllysine at residue 4 of histone H3 (H3K4me3, Catalog No. 39915) was used in ChIP with varying amounts of secondary IgG (Jackson ImmunoResearch Laboratories Inc). Following enrichment, qPCR was performed using primers against untranslated region 12 (Untr12) and GAPDH. Untr12, a gene desert on chromosome 12, shows no or low H3K4me3 enrichment, while GAPDH, an actively transcribed gene that is associated with the presence of H3K4me3, shows varying enrichment depending on amount of secondary antibody. The optimal ratio of primary H3K4me3 antibody to secondary IgG is 1:1 with half the amount of primary relative to secondary (2:1) also giving a high signal (FIG. 25).

ChIP data is expressed as binding events detected per 1,000 cells which represents the average of the raw data triplicates adjusted for the amount of chromatin in the reaction, the resuspension volume and the primer efficiency. Applicant's custom ChIP service has performed and analyzed hundreds of ChIP assays with a broad range of primary antibodies and this calculation provides consistency in data analysis and allows direct comparison across samples and experiments. This scale can be converted to enrichment over input (used in some figure below) by dividing binding event values by 1,000.

Antibody-Oligonucleotide Conjugation.

The secondary antibody was conjugated to single-stranded oligonucleotides (A and B, Table 4) with appended ends containing at the 5'end two iterations of an 18-carbon long hexaethyleneglycol spacer (Sp18) and a 5' Thiol Modifier C6 S—S (ThiolC6) via thiol-maleimide/thiol exchange chemistry which targets introduced maleimide/thiol exchange residues on the antibody. The objective was to introduce a cleavable (disulfide) bond between the antibody and oligonucleotide to facilitate separation and isolation of tagmented DNA fragments in downstream steps.

TABLE 4

Sequences of single stranded oligonucleotide A and B conjugated to a 18-carbon spacer

| | |
|---|---|
| Oligonucleotide A SEQ ID NO: 7 | ThiolC6//Sp18//Sp18/TCGTCGGCAGC GTCAGATGTGTATAAGAGACAG |
| Oligonucleotide B SEQ ID NO: 8 | ThiolC6//Sp18//Sp18/GTCTCGTGGGC TCGGAGATGTGTATAAGAGACAG |

Figure 26:
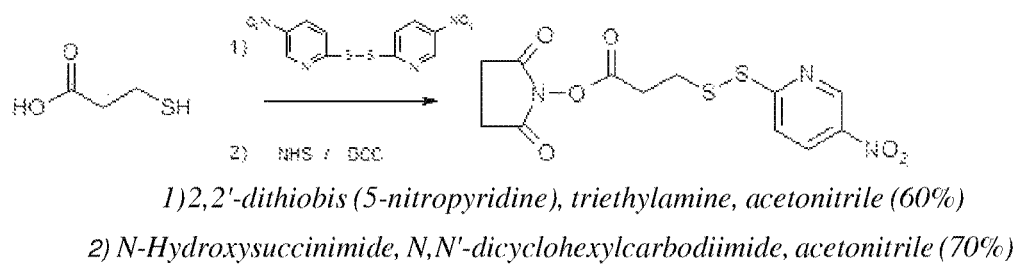
FIG. 26—shows Synthesis of nitro-SDPD. Mercaptopropionic acid in acetonitrile was treated with 2,2'-dithiobis (5-nitropyridine) in the presence of triethylamine. Citric acid solution was added and the resulting 3-([5-nitro-2-pyridyl] dithio) propionic acid was extracted with dichloromethane. The product was purified by silica gel flash chromatography. To prepare an active form, 3-([5-nitro-2-pyridyl]dithio) propionic acid and N-hydroxysuccinimide were dissolved in acetonitrile and N,N'-dicyclohexylcarbodiimide was added. Once the reaction was complete, crude nitro-SPDP was purified by preparative thin layer chromatography.

Conjugations were performed using a 6-fold molar excess of single-stranded oligonucleotides to achieve antibodies containing a minimum of 2 oligos/antibody. In the initial approach, an equimolar mixture of A and B oligo was used in the conjugation reaction. Consequent, reaction products will contain a mixture of conjugation products (A:A, A:B and B:B). To create a cleavable link between the secondary antibody and the conjugated oligonucleotides, a disulfide bond was introduced. To achieve this, the antibody had to be modified prior to forming the disulfide bond with the oligonucleotides. In a first attempt, the commercial reagent SPDP (cat #21857; Pierce) failed to give satisfactory results. However, by following another approach and synthesizing nitro-SPDP, we were able to modify the antibody. Mercaptopropionic acid in acetonitrile was treated with 2,2'-dithiobis (5-nitropyridine) in the presence of triethylamine. Citric acid solution was added and the resulting 3-([5-nitro-2-pyridyl]dithio) propionic acid was extracted with dichloromethane. The product was purified by silica gel flash chromatography. To prepare an active form, 3-([5-nitro-2-pyridyl]dithio) propionic acid and N-hydroxysuccinimide were dissolved in acetonitrile and N,N'-dicyclohexylcarbodiimide was added. Once the reaction was complete, crude nitro-SPDP was purified by preparative thin layer chromatography (FIG. 26).

During antibody activation, nitro-SPDP precipitated out of solution and subsequent successful activations were performed in the presence of DMSO. Use of DMSO may not be suitable with primary antibodies.

The Nitro-SPDP activated antibody was subsequently desalted and mixed with the A-METS and B-METS oligonucleotide at a 6-fold excess to perform the conjugation reaction involving the disulfide bond formation between nitro-SPDP residues and thiol groups of the oligonucleotides. The reaction efficiency was verified on a 10% native polyacrylamide gel (FIG. 27A) which was stained after electrophoresis with the nucleic acid stain GelRed to identify migration of DNA-protein complexes. Free oligonucleotides will migrate quickly to the bottom of the gel, while antibody-DNA complex migrating more slowly will be retained near the top of the gel. Detection of these slow migrating complexes with the DNA stain confirms the success of the conjugation reaction. The ladder effect observed where the antibody-DNA complexes migrate may be due to varying DNA:antibody molar ratios, however this was not investigated.

Figure 27:
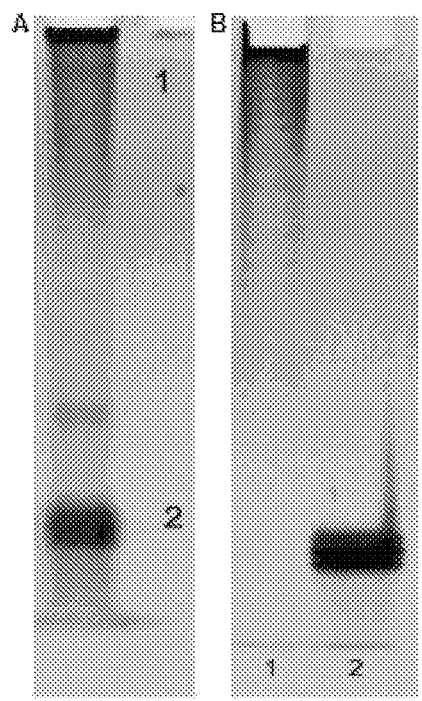
FIG. 27 shows Analysis of secondary antibody conjugate on 10% native polyacrylamide gel 2 μg of conjugated antibody loaded on a 10% native polyacrylamide gel and stained with GelRed nucleic acid stain. 1 indicates antibody-oligonucleotides conjugate zone and 2 oligonucleotides zone. A. 1/150 of isolated chromatography peaks 1 and 2 from FIG. 16 loaded on a 10% native polyacrylamide gel and stained with GelRed nucleic acid stain. 1 indicates Chromatography peak "1" and 2 Chromatography peak "2". Peak "1" consists of pure antibody-oligonucleotide conjugate and is devoid of free oligonucleotide.

Several purification and separation approaches were tested. However, both Protein A/G Spin Kit (cat #89980 from Pierce; manufacturer protocol was used) and Thiophilic Adsorbtion Kit (cat #44916 from Pierce; manufacturer protocol was used) failed to achieve the desired separation of free oligonucleotide from antibody-oligo conjugate. Only size exclusion chromatography, using a HiLoad 16/600 Superdex 75 µg column, was able to purify the antibody-oligonucleotide conjugate and remove free oligos. The antibody-oligonucleotides reaction mixture was diluted with running buffer (50 mM Tris, 200 mM NaCl pH 8 and loaded onto the HiLoad 16/600 Superdex 75 pg column. The running buffer was pumped through the column at 1 ml/min till the chromatography was completed. UV absorbance at three wavelengths was used as a detection method. FIG. 17 illustrates the AKTA size exclusion chromatography profile at three wavelengths. The absorbance at 214 nm represents mostly protein concentration and the absorbance at 260 nm and 280 nm represent mostly oligonucleotides concentration. Absorbance at 260 nm was used to determine molar incorporation of oligonucleotide. Further, the purification and separation was verified on a 10% native polyacrylamide gel by loading chromatography peaks 1 and 2 (FIG. 27B).

Functionality of Antibody-Oligonucleotide Conjugate in ChIP

Figure 28:
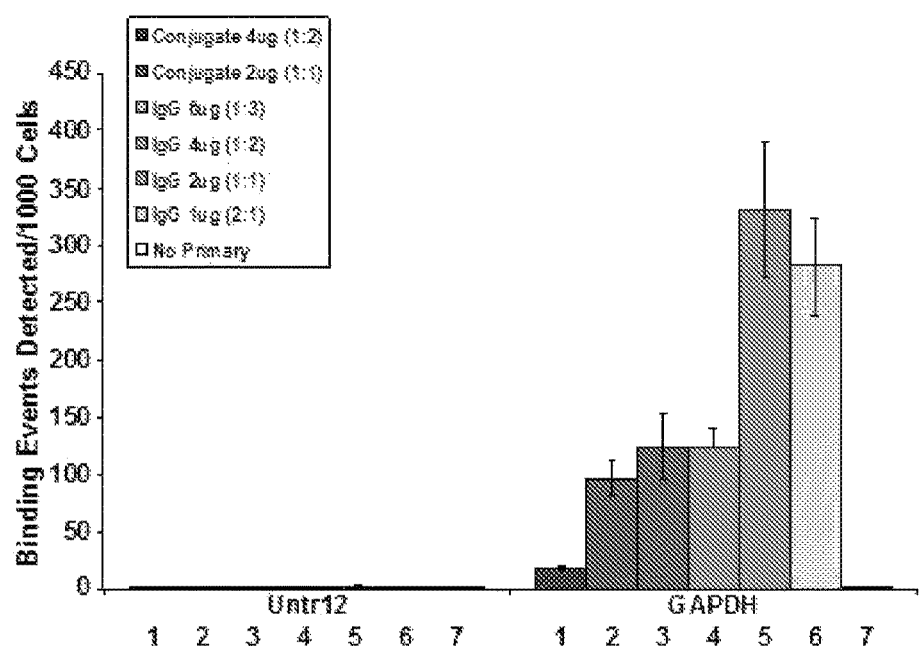
FIG. 28—shows secondary antibody retains binding activity after conjugation. 10 μg of MCF7 crosslinked chromatin was used in ChIP for immunoprecipitation with 2 μg of H3K4me3 antibody and 4 ug (1) or 2 ug (2) of secondary antibody-conjugate and compared with 6 ug (3), 4 ug (4) 2 ug (5) or 1 ug (6) of unconjugated secondary antibody and (7). No primary antibody and 2 μg of secondary antibody-conjugate.

A portion of the generated conjugate was tested by conventional ChIP to confirm that the addition of the oligonucleotides did not impair primary antibody binding. Chromatin was prepared as described above and Applicant's H3K4me3 antibody was used as the primary antibody with two different ratios of secondary antibody-conjugate. Following enrichment, qPCR was performed using primers against untranslated region 12 (Untr12) and GAPDH. As illustrated in FIG. 28 columns 1 and 2, the antibody-conjugate still possesses binding activity and the optimal ratio of primary H3K4me3 antibody to secondary antibody-conjugate is 1:1. This experiment also contains the same data shown in FIG. 26 where the non-conjugated secondary was used to enable direct comparison (columns 3-7). Thus, while the function of the conjugate is attenuated in ChIP (by three-fold), it was judged to be sufficiently robust to pursue further testing.

Functionality of Antibody-DNA Conjugate in Transposomes

A series of experiments were performed to test whether oligonucleotides now tethered to an antibody would still associate with the transposome to form a functional transposome and to determine the optimal conditions for tagmentation with the antibody/transposome complex. First, since the antibody-conjugate was constructed using single-stranded oligonucleotides, the complementing p-MENTS sequence oligonucleotides were added (FIG. 18), allowed to anneal for one hour at room temperature (1:1 molar ratio) to form double-stranded oligonucleotides. This conjugate was then incubated with the transposases at 1:1 molar ratios for one hour at room temperature to assemble the Tn5 transposome complex. The functionality of this conjugate was tested in ChIP to confirm that the addition of oligonucleotides did not interfere with its ability to interact with rabbit primary antibodies. A two to three fold reduction was observed but deemed not significant enough to be of concern for this proof of concept stage of the project.

The ability of the antibody-tethered oligonucleotides to form a functional transposome was also determined. Activity was first tested at 55° C. for 30 min, the standard temperature for the Tn5 transposase, and also for longer durations at 37° C. (FIG. 19B) due to concerns that elevated temperatures when applied to the TAM-ChIP procedure would destabilize antibody-chromatin interactions. Tagmentation of purified genomic DNA was detected at both temperatures. However, a portion of untagmented input DNA (arrow) remained in all conditions indicating that the tagmentation was incomplete. It was noted that less untagmented DNA remained in all TS-Tn5 reactions, suggesting that the TS-Tn5-transposome-antibody complex may be more robust than its Tn5 counterpart. However, it is not clear if the incomplete tagmentation reactions with the transposome-conjugates are due to reduced transposase activity, incomplete or incorrect assembly of the transposome complex or due to steric hindrance from being antibody-tethered. However, the residual activity may nonetheless be sufficient for TAM-ChIP. Primary antibody targeting of the transposome-antibody conjugate to chromatin could potentially overcome the decrease in random transposition activity through primary antibody mediated stabilization of the transposome/antibody/chromatin complex, which would effectively drive the reaction forward.

Figure 29:
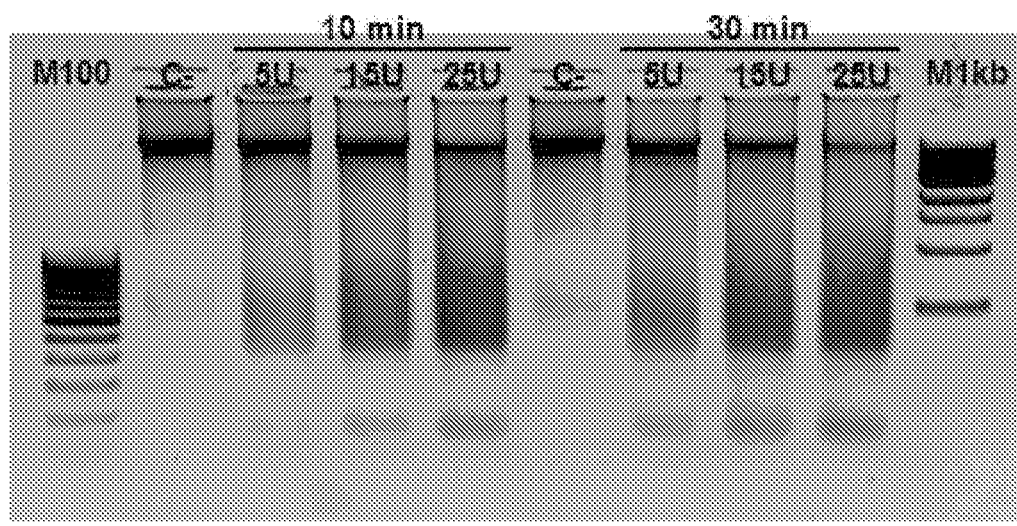
FIG. 29—Tagmentation of genomic DNA by the Tn5 transposase assembled to oligonucleotide-antibody conjugate at different concentrations and time lengths. Tagment DNA buffer and varying amounts of the Tn5 transposome-conjugate was incubated with 1 μg of genomic MCF7 DNA at 55° C. degrees for 10 and 30 minutes. Half of the tagmented DNA was analyzed on a 1.5% agarose gel. C− indicates DNA with no transposase added.

The assembled transposome was incubated with genomic MCF7 DNA at various concentrations ranging from 5 to 25 units and extending the incubation at 55° C. to 10 and 30 minutes. FIG. 29 shows that the tagmentation efficiency of the antibody/transposome complex is reduced. Untagemented input DNA co-migrating with the band in the no enzyme (C−) lanes) persists in reactions with the oligonucleotide-antibody conjugate. This can be compared with reactions in FIG. 19 where no unfragmented DNA is detectable in all enzyme containing reactions. While increasing the amount of enzyme did increase tagmentation, a longer incubation at 55° C. did not yield a significant improvement.

Figure 30:
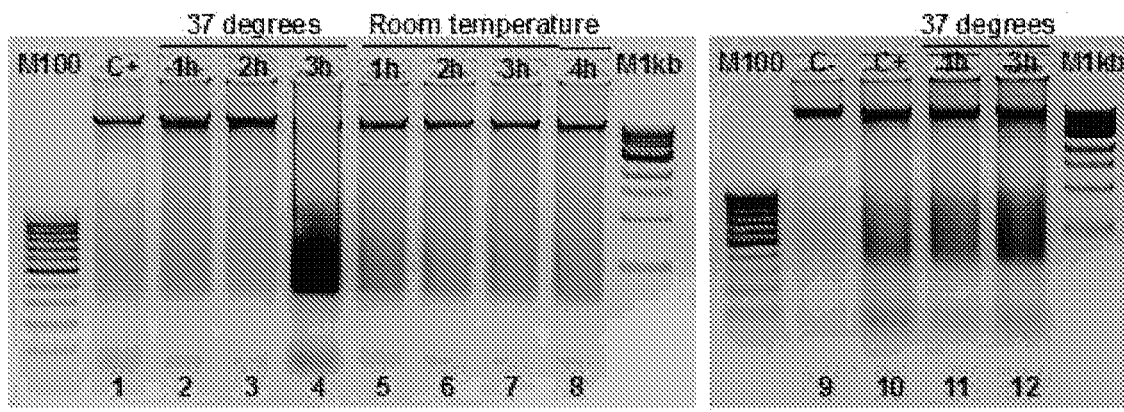
FIG. 30—Tagmentation of genomic DNA by Tn5 assembled to oligonucleotide-antibody conjugate at different temperatures. Tagment DNA buffer and 25 units of the Tn5 transposome-conjugate was incubated with 1 μg of genomic MCF7 DNA at either 37° C. or room temperature for various time lengths. Half of the tagmented DNA was analyzed on a 1.5% agarose gel. C+ indicates Tn5 transposome incubated at 55° C. for one hour.

Since TAM-ChIP requires the antibody to still be bound to its target during the tagmentation reaction, transposase activation at 55° C. could potentially adversely affect antibody to remain bound to its target protein. Therefore, the tagmentation at a lower temperature was assessed. Twenty-five units of the assembled Tn5 transposome was incubated with genomic DNA at 37° C. and room temperature for varying times to identify optimal conditions for tagmentation at lower temperatures. In the initial experiment the three hour incubation at 37° C. resulted in a strong increase in tagmentation; however, when this reaction was repeated, the same significant effect was not observed. The initial result was either an artifact of unequal sample loading on the gel (FIG. 30, compare lanes 3 and 4 with lanes 11 and 12), or this sample may have inadvertently received a higher amount of the antibody/transposome complex.

Figure 31:
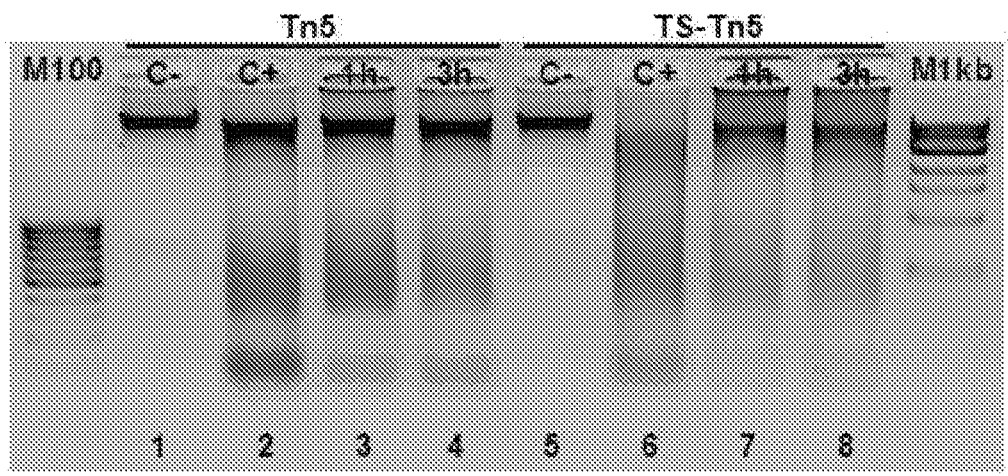
FIG. 31—shows Tn5 and TS-Tn5 Transposome-Conjugate efficiency on genomic MCF7 DNA. Tagment DNA buffer and 25 units of Tn5 or TS-Tn5 transposase assembled with antibody-oligonucleotide conjugate was added to 1 μg of genomic MCF7 DNA. The samples were incubated at 55° C. for one hour (C+) or 37° C. for one to three hours. Half of the tagmented DNA was analyzed on a 1.5% agarose gel. C−, DNA with no transposase added.

In the next experiment, twenty-five units of either the Tn5 and TS-Tn5 transposome-conjugates were added to 1 µg of genomic MCF7 DNA and incubated at either 37° C. for one or three hours or 55° C. for one hour (FIG. 31, lanes marked C+). Interestingly, although both enzymes show reduced tagmentation activity when assembled to the oligonucleotide-conjugate, the TS-Tn5 transposome exhibited higher activity than the Tn5 transposome with almost complete tagmentation at 55° C. where unfragmented DNA is undetectable (compare lanes 2 and 6 in FIG. 31).

The reason for reduced activity of the antibody/transposome complex is not clear. The incomplete tagmentation reactions with the transposome-conjugates could be due to reduced transposase activity, incomplete or incorrect assembly of the transposome complex or due to steric hindrance from being antibody-tethered. However, the residual activity may nonetheless be sufficient for TAM-ChIP. Primary antibody targeting of the transposome-antibody conjugate to chromatin could potentially overcome the decrease in random transposition activity through primary antibody mediated stabilization of the transposome/antibody/chromatin complex, which would effectively drive the reaction forward.

Summary of Results

The data in this example demonstrate the development of a conjugation strategy which was successful in the generation of an antibody-DNA conjugate. The data also demonstrate functionality of the conjugate in both ChIP and transposase functions, albeit at attenuated levels. In ChIP experiments, the same primary to secondary antibody ratio requirement was retained post-conjugation. When assembled into a transposome, tagmentation of genomic DNA was demonstrable, indicating that the antibody-transposome complex was formed and functioned.

Example 13—TAM-ChIP Validation

To test the above hypothesis that antibody localization of transposase to chromatin would overcome the attenuation of transposase activity the following prototypic TAM-ChIP experiments were performed.

Functionality of Tn5 and TS-Tn5 Transposomes Assembled with Antibody-Oligonucleotide Conjugate in ChIP A portion of the antibody-transposome complexes generated as described were used in a set of preliminary ChIP experiments. The H3K4me3 primary antibody used above was incubated with 10 µg of chromatin overnight. The transposome-antibody conjugate, either Tn5 or TS-Tn5, was added at a ratio of 1:1 of primary antibody to secondary-transposome conjugate, and incubated at 4° C. for four hours to allow binding of the secondary antibody-transposome to the primary antibody. The reaction was diluted first with four volumes of the buffer used in the immunoprecipitation step of traditional ChIP and one volume of $Mg^{2+}$ containing tagmentation buffer to activate the transposase during a three hour incubation at 37° C. Antibody bound chromatin tagmented by the transposome was captured using Protein G agarose beads (Invitrogen) and eluted following established ChIP procedures in the presence of TCEP (Tris (2-Carboxyethyl) phosphine) to reduce the disulfide bonding linking oligonucleotide with antibody. After Proteinase K treatment and reversal of formaldehyde crosslinks, achieved with a two hour incubation at 80° C., half of the eluted DNA was subjected to 25 cycles of the four primer PCR reaction shown in FIG. 9 using Primer 1+2 and Adapters 1b and 2b (Table 3) as described above FIG. 22. The PCR amplification products were purified using Agencourt AMPure XP magnetic beads and eluted in 30 µl of elution buffer. DNA concentration was measured using a Nanodrop spectrophotometer and samples were diluted to 2 ng/µl.

Following dilution, qPCR was performed on 10 ng of DNA using primers against the negative control regions Untr12 and Untr20 as well as positive control regions for H3K4me3 GAPDH and Zc3h13. FIG. 21 shows quantitation of the qPCR products for these loci.

In the above procedure, protein G agarose beads were used in lieu of the streptavidin-beads to avoid complications stemming from biotin-streptavidin interactions. Thus the oligonucleotides designed and used in this example lacked a biotin moiety.

Figure 32:
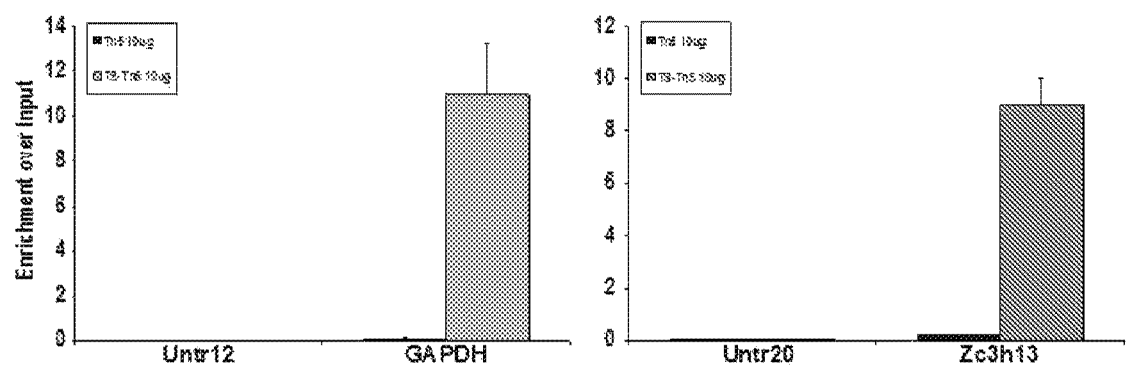
FIG. 32—shows Quantitative PCR analysis of Tn5 and TS-Tn5 transposome/antibody conjugates in ChIP with H3K4me3 primary antibody. 10 ug of cross-linked MCF7 was used in ChIP with 4 μg of H3K4me3 antibody and 4 μg secondary antibody-conjugate. Tagmentation buffer was added after allowing the secondary antibody-transposome conjugate to bind the H3K4me3 and the bound chromatin captured with Protein G agarose beads.
Figure 33:
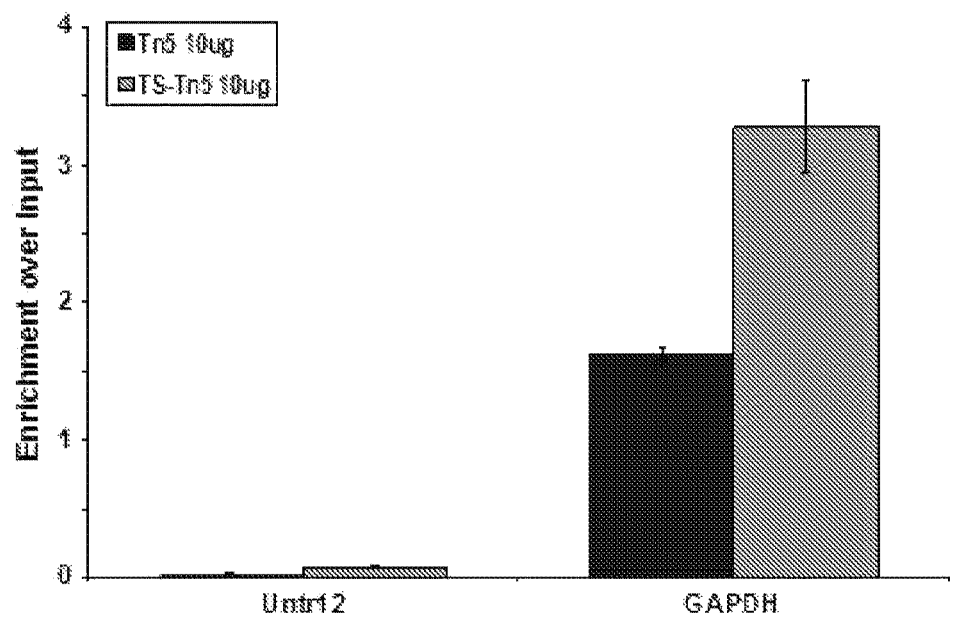
FIG. 33—QPCR profile without four primer PCR library amplification. Half of the eluted ChIP DNA from the ChIP experiment in FIG. 31 was diluted to mimic the bPCR step, purified with Agencourt AMPure beads and 10 ng subjected to qPCR using primers against Untr12 and GAPDH.

FIG. 32 shows that the TS-Tn5 but not the Tn5 transposome complex effectively tagmented the regions bound by the primary antibody at a chromatin concentration of 10 µg. The gene deserts and untranslated regions on chromosome 12 and 20 were not detected, indicating no tagmentation by the transposase at these loci. These data are consistent with those in FIG. 31, where Tn5 transposome/antibody complex exhibited lower tagmentation when compared to the TS-Tn5 transposome/antibody complex. The data in FIGS. 32 and 33 are expressed as enrichment over input and not as binding events per 1,000 cells because four primer PCR was performed prior to qPCR analysis thereby eliminating the possible equation to cell equivalents. Note this scale is three order of magnitude smaller.

One possible interpretation of these results is that the observed enrichment (FIG. 32) was not a reflection of the actual amplification of tagmented target DNA during the four primer PCR reaction but rather an amplification of untagmented H3K4me3 enriched DNA carried over from when protein G beads were used to isolate antibody/chromatin complexes ChIP. To account for this possibility, the remaining half of the eluted DNA was diluted to mimic the PCR reaction steps performed above, but not subjected to the actual four primer PCR amplification, followed by purification with Agencourt AMPure XP magnetic beads. The purified DNA was eluted in 30 µl, diluted to 2 ng/µl and qPCR performed on 10 ng of DNA using negative (Untr12) and positive (GAPDH) control primers. While FIG. 33 shows the result that would have been expected from a traditional ChIP using the H3K4me3 antibody, as in FIG. 28, the enrichment relative to input is at least three fold lower. This reduction was determined to be significant, especially when considering that the modest amount of GAPDH was detect in the Tn5 reaction in FIG. 33 translated to essentially undetectable levels following four primer PCR in FIG. 32. Thus while untagmented DNA may contribute to the signals detected in FIG. 32, it is likely small and insignificant.

Thus, the results depicted in FIG. 32 clearly demonstrate the successful and specific tagmentation of H3K4me3 antibody bound regions by the TS-Tn5 transposome while the reduced tagmentation activity of the Tn5 transposome conjugate resulted in no or undetectable levels of tagmentation of the target regions and was not used further.

To confirm the results achieved above and further optimize TAM-ChIP performance, several variables were next introduced. These included varying amounts of chromatin (10 and 1 µg), antibody-transposase concentrations (1:1 and 2:1 ratios of secondary/transposase conjugate relative to primary antibody) and incubation times of the TS-Tn5/secondary complex (2 and 4 hours) with primary antibody:chromatin complexes before transposase activation. Antibody-bound DNA was isolated as described above followed by four primer PCR. qPCR of amplified DNA was performed using primers against Untr12 and GAPDH. This experiment was performed twice with inconsistent results indicating that optimization will be required to achieve reproducibility (FIG. 34).

Both experiments showed specific association of the H3K4me3 with the GAPDH region and not with Untr12, the condition which produced the highest capture of a H3K4me3-associated genomic regions was with 10 µg chromatin in both, but for FIG. 34A, an incubation time of two hours with 1:2 ratios of primary to secondary/transposome was best, while in the experiment in FIG. 34B, an incubation time of four hours of the secondary: transposase complex that was added at a ratio of 1:1 relative to the primary antibody gave better results The experiments preformed in FIG. 34 included no primary antibody (TS-Tn5 transposome/secondary complex only) and no secondary antibody controls to ensure that the observed enrichment was actual tagmentation by the transposase at regions bound by the primary antibody and not only tagmentation of any open chromatin regions accessible to the enzyme, a control reaction with no primary antibody was performed. Samples lacking primary antibody (FIG. 34B) show no enrichment thus confirming that the observed tagmentation is taking place only at chromatin regions bound by the primary antibody. The next step in the validation of the TAM-ChIP methodology is a genome wide comparison of the libraries generated via the method developed herein with the H3K4me3 antibody and those by traditional ChIP-Seq methods with the same antibody. To that end the tagmented DNA generated in the experiments depicted in FIGS. 32 and 34 were prepared for sequencing on an Illumina platform. To confirm that the size of the generated library was within the correct range two independent library preparations were run on a 1.5% agarose gel. In both libraries a majority of fragments in the population range between 200-400 bp in length an ideal size for next generation sequencing.

Sequencing and 50-nt reads were generated on a HiSeq sequencer and aligned to the human genome (hg19). Only uniquely aligning reads were kept and duplicate reads were removed, resulting in 545,182 alignments for the TAM-ChIP sample. A control standard ChIP-Seq data set (traditional ChIP-seq on MCF7 chromatin using the H3K4me3 antibody) was down-sampled to the same number of alignments and analyzed in parallel. Signal maps were generated and the fragment densities in 32-nt bins along the genome was determined. The resulting histograms were visualized in the Integrated Genome Browser (IGB). Peak calling was performed using SICER (Zang et al., Bioinformatics 25, 1952-1958, 2009) at a standard cutoff of E-value=1. SICER identified 10,897 peaks for TAM-ChIP and 12,526 peaks for traditional ChIP, which are within expectations for this histone mark if compared to numerous previous assays and 91.5% of the TAM-ChIP peaks overlapped with the traditional ChIP peaks (FIG. 15).

Figure 35:
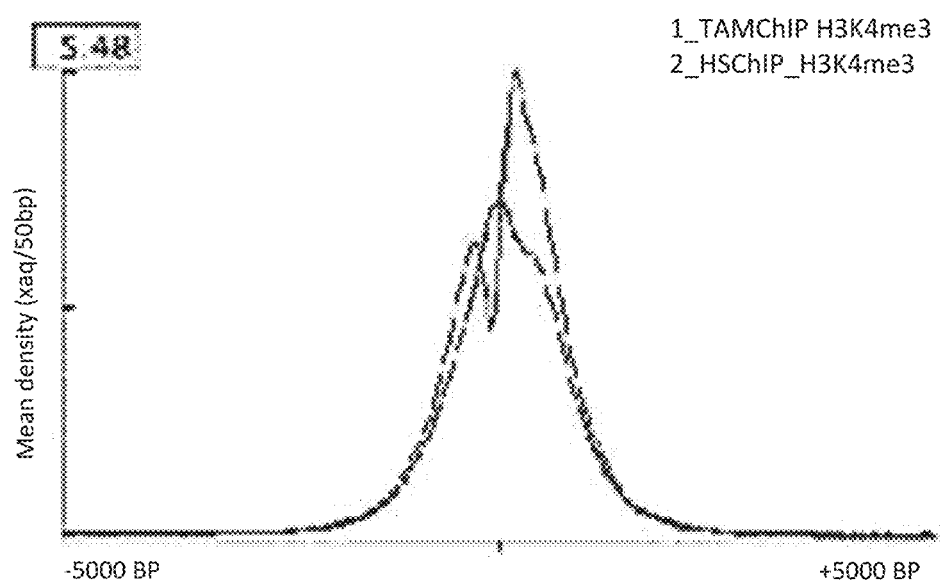
FIG. 35—SeqMINER promoter profiles of the TAM-ChIP and traditional ChIP NGS HiSeq data. Tag densities from each ChIP-seq dataset were collected within a window of 10 kb around the reference coordinates, the collected data were subjected to k-means clustering (using linear normalization). Using seqMINER, the average profile for selected clusters was automatically calculated and plotted. The H3K4me3 mean profile for traditional ChIP-seq (graph with highest peak) and TAM-ChIP-seq (graph with lowest peak) was calculated and represented.

When annotated with genes, it was found that 83.6% of the TAM-ChIP peaks and 84.2% of the traditional ChIP peaks were located in promoters (defined as −7500 to +2500 relative to TSS). In conclusion, the correlation between the TAM-ChIP and traditional ChIP data is extremely high. In both assay, highest signals were seen at the transcriptional start site (TSS), as shown in the promoter profile (−5000 to +5000) generated by seqMINER in FIG. 35, which is consistent with published results (Ye et al., 2011). The typical seqMINERS promoter profiles for H3K4me3 ChIP-seq data show double peaks as can be seen for the traditional ChIP-seq in pink. The profile for the generated TAM-ChIP library on the other hand does not show the exact same pattern. These data indicate that although the generated library was strikingly similar (91.5%) to the traditional ChIP additional optimization of the current TAM-ChIP library generation is required to achieve the optimal TAM-ChIP protocol for multi-analyte purposes.

These results indicate that the TS-Tn5 transposase can be directed in a specific manner to chromatin via an antibody specific for a chromatin associated protein—in this case, a post-translational histone modification that is associated with transcriptionally active regions of the genome. Together the results presented herein clearly establish proof of concept.

Example 14—Enrich for DNA Methylated Genomic Regions Using Transpososome-Antibody/Oligonucleotide Complex Approach: A recombinant tagged methyl-binding protein (in this case a His tagged MBD2 and/or MBD3 protein(s)) binds to methylated DNA and an anti-His antibody that has been conjugated with the same oligonucleotides containing the NGS adaptor and transposase sequences that bind to the methyl binding protein such that upon transposase activation the oligonucleotide sequence is integrated into region of DNA methylation.

Uniqueness Relative to "TAM-ChIP":
1) Uses genomic DNA as a substrate as opposed to chromatin
2) Uses DNA binding proteins instead of a primary antibody
3) An antibody that recognizes the tag on a protein delivers the oligonucleotide sequence to the DNA
4) Can be combined with other DNA modification marks, including hydroxymethylcytosine, carboxylcytosine and formylcytosine in addition to methylcytosine Here data is present utilizing the antibody directed insertion of barcodes/sequences using the transposase to determine DNA methylation levels in genomic DNA will allow this method to crossover into the field of DNA methylation, which is also analyzed at genome-wide levels and will also facilitate an emerging trend of studies that examine how distinct epigenetic regulatory mechanisms overlap or are co-integrated.

This approach enables the multianalyte capabilities of this assay as 5-mC, 5-hmC, 5-caC and 5-fC and can be performed on unfragmented DNA which would likely reduce input DNA amounts compared to over methylation enrichment technologies (e.g. MeDIP). Using this approach the library preparation step will be eliminated and it is possible that the immunoprecipitation step may also be removed.

The method described herein is based on Applicant's MethylCollector™ assay, which enriches CpG-methylated DNA from limited amounts of cell or tissue samples (FIG. 37). The method is based on the Methylated CpG Island Recovery Assay (MIRA), which utilizes the high affinity of the MBD2b/MBD3L1 complex for methylated DNA. In MethylCollector™ and MethylCollector™ Ultra His-tagged recombinant MBD2b, either alone (MethylCollector™) or in a complex with MBD3L (MethylCollector™ Ultra) to increase affinity, is incubated with fragmented DNA and it specifically binds to CpG-methylated DNA. These protein-DNA complexes are then captured with nickel-coated magnetic beads and subsequent wash steps are performed to remove fragments with little or no methylation. The methylated DNA is then eluted from the beads in the presence of Proteinase K and enriched DNA can be used in many downstream applications, such as end point or real time PCR analysis, bisulfite conversion, microarray analysis, sequencing, etc.

The first step to determine the feasibility of adapting the described MethylCollector™ protocol for use with the transposome/antibody conjugate was to confirm that MBD2b binding was retained in conditions required for the tagmentation (i.e. low magnesium and 37°). The modified MethylCollector™ protocol included the necessary steps for binding of the anti-His antibody and tagmentation of the DNA by the transposome (FIG. 38).

Figure 38:
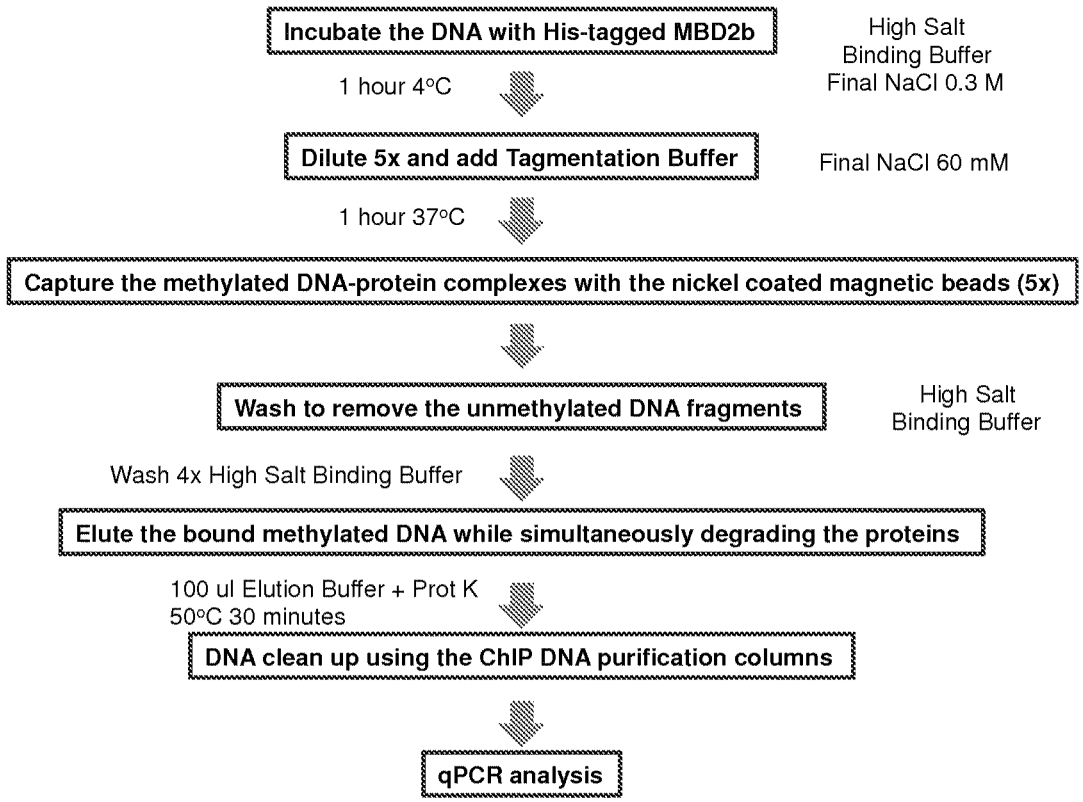
FIG. 38—shows the modified MethylCollector™ protocol to determine the feasibility of altering the current protocol to include the transposome required conditions.
Figure 39:
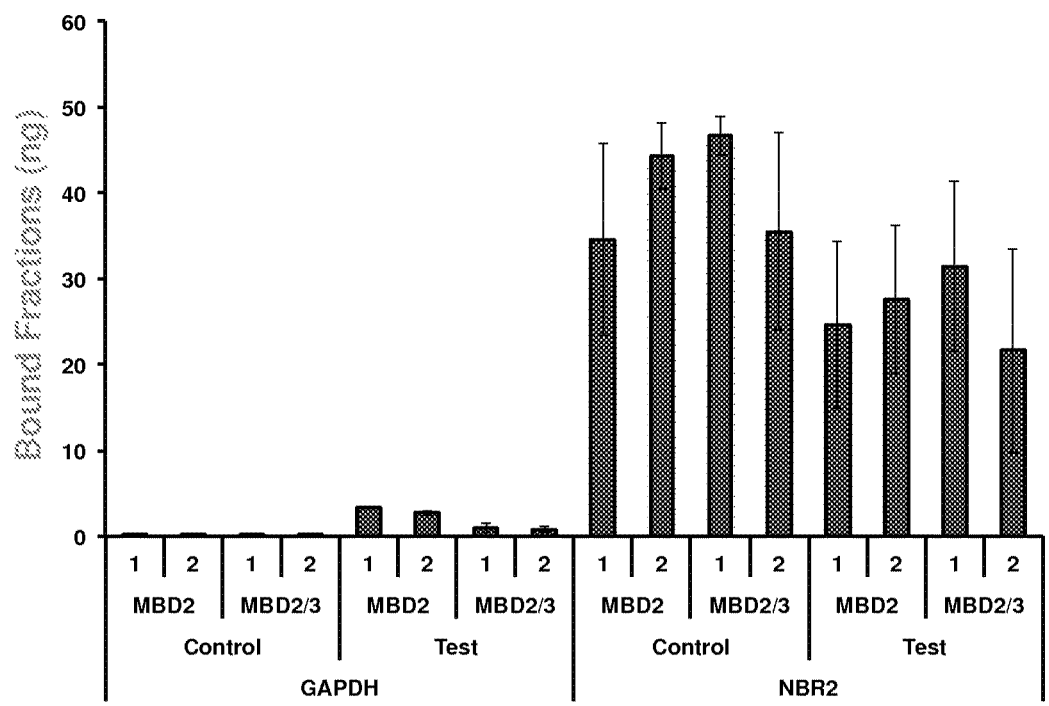
FIG. 39—shows DNA methylation enrichment using the modified MethylCollector™ protocol FIG. 40—shows the modified MethylCollector™ protocol to become TAM-MIRA.

The experiment was performed in duplicate with either 4 ug of MBD2b alone or together with MBD3L on 100 ng of fragmented human genomic DNA following either the original MethylCollector protocol (FIG. 37) or the modified protocol (FIG. 38). As depicted in FIG. 39, the modified protocol (Test) shows some loss in sensitivity, but overall the results were promising as the methylated positive control region, NBR2, show significant enrichment over the unmethylated negative control region, GAPDH.

Based on these results an antibody conjugate directed against the His tagged MBD2 was developed. The transposase recognition sequences (A- and B-METS) was conjugated to an anti-His antibody (Pierce 6His epitope tag antibody (MA1-21315)) using the same conjugation strategy as described previously. The retained activity of the conjugated antibody was confirmed by dotblot against 0-1000 ng of His-tagged recombinant MBD2b (data not shown).

After confirming the retained activity of the anti-His antibody, we further confirmed the functionality of the assembled conjugated antibody-transposome complex. Unfragmented genomic DNA was incubated with 25 units of the assembled transposome complex and incubated at 500 for five minutes, or at 37° for either 1 or 3 hours. All reactions showed the same level of tagmentation and fragmentation of the genomic DNA compared to control reactions using an unconjugated transposome complex (data not shown)

Figure 40:
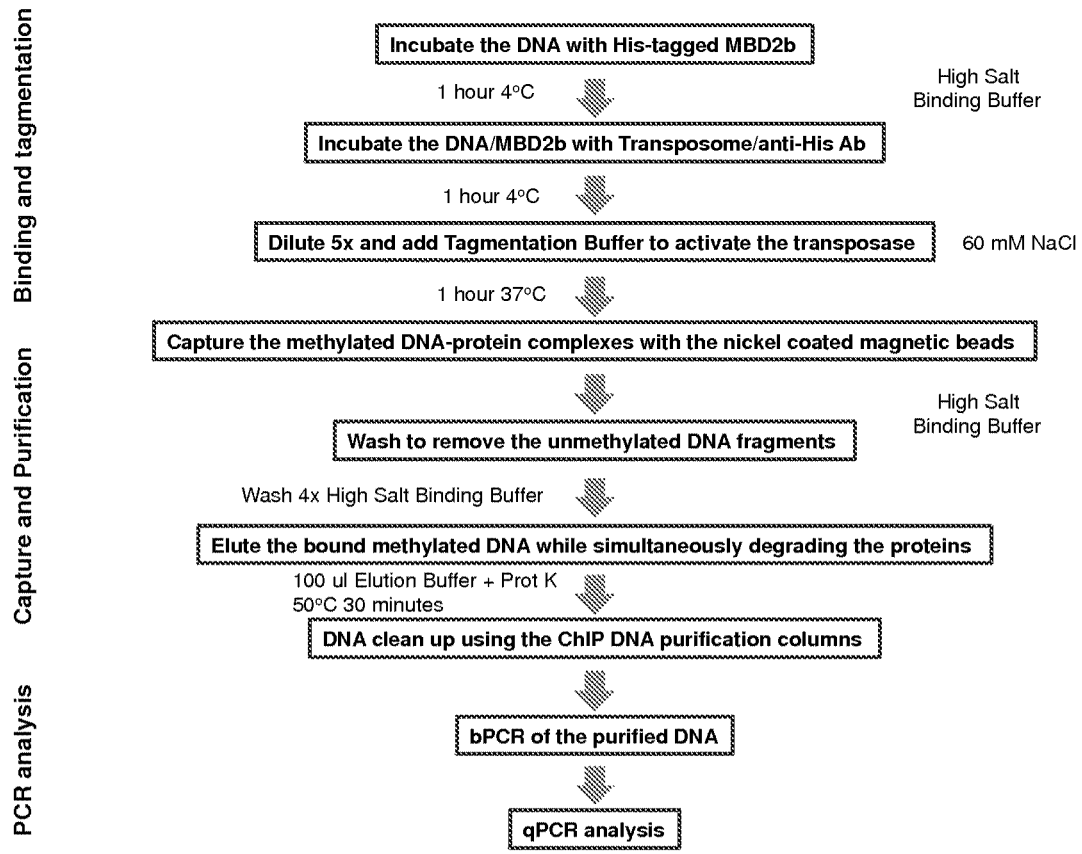

The next step was to determine the feasibility of utilizing this antibody conjugate in the MethylCollector™ assay and generating specific tagmentation by the transposome of only those regions containing DNA methylation. Applicant incubated the His-tagged MBD2b and the anti-His antibody conjugate/transposome at a 1:1 ratio (4 ug of MBD2b and 4 ug of the anti-His antibody) with 100 ng unfragmented human genomic DNA (FIG. 40). For half the samples the bound DNA was captured using the nickel coated magnetic beads prior to purification (beads 1-3) and for the other half the capture step was omitted and all DNA purified (No Beads 1-3). Each condition was performed in triplicate. The purified DNA was subjected to 25 cycles of PCR amplification using the same adapters and primers utilized in TAM-ChIP. All libraries were purified using standard methods and diluted to 2 ng/ul. Quantitative PCR was performed using primers targeting the regions known to be negative (Untr12) or positive (GEMIN4) for DNA methylation.

Figure 41:
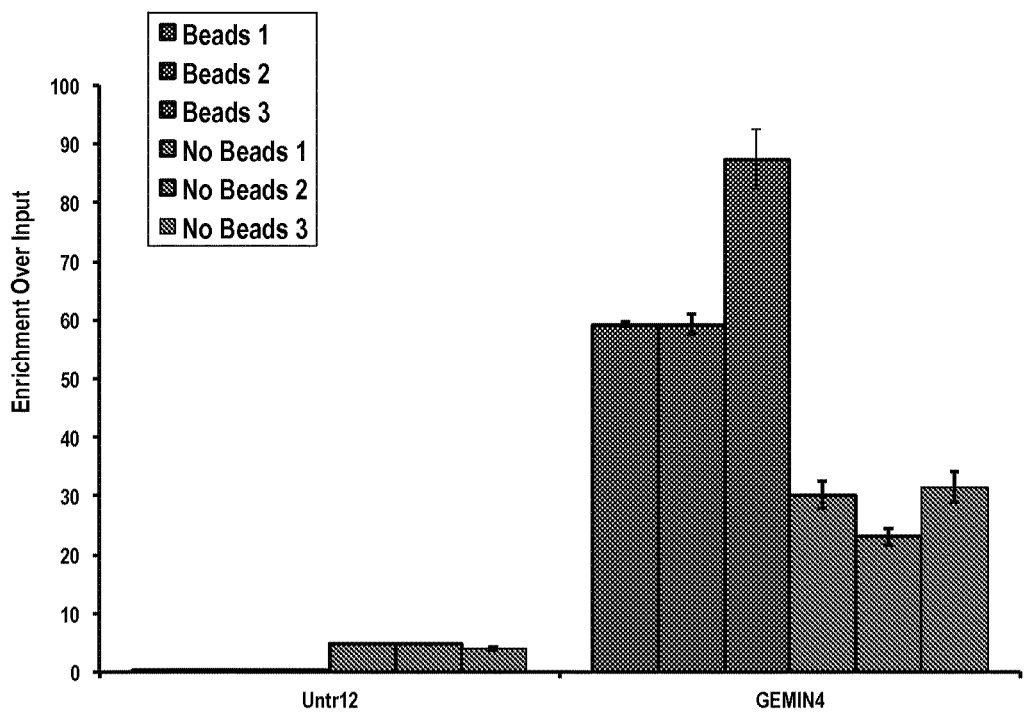
FIG. 41—shows TAM-MIRA to determine 5-mC levels in human genomic DNA.

FIG. 41 shows that the anti-His antibody conjugate-transposome complex effectively tagmented those regions bound by the MBD2 protein, such as GEMIN4. Further, the untranslated region on chromosome 12 known to be unmethylated, showed no enrichment, indicating no tagmentation by the transposase, confirming that the MBD2b protein was directing the transposase to those DNA loci associated with MBD2b.

As one of the main advantages of the TAM-MIRA™ methodology (as disclosed herein) is its putative multianalyte capability, Applicant has initiated studies to show that this approach can be applied to determine 5-hmC levels in genomic unfragmented DNA. The advantages in studying 5-hmC compared to 5-mC enrichment is that one can utilize an antibody such as the Active Motif 5-Hydroxymethylcytosine antibody that recognizes and binds both single- and double-stranded DNA. (An alternative approach is to use tagged hmc-binding proteins followed by transpososome complexes containing an antibody to the tag).

Figure 42:
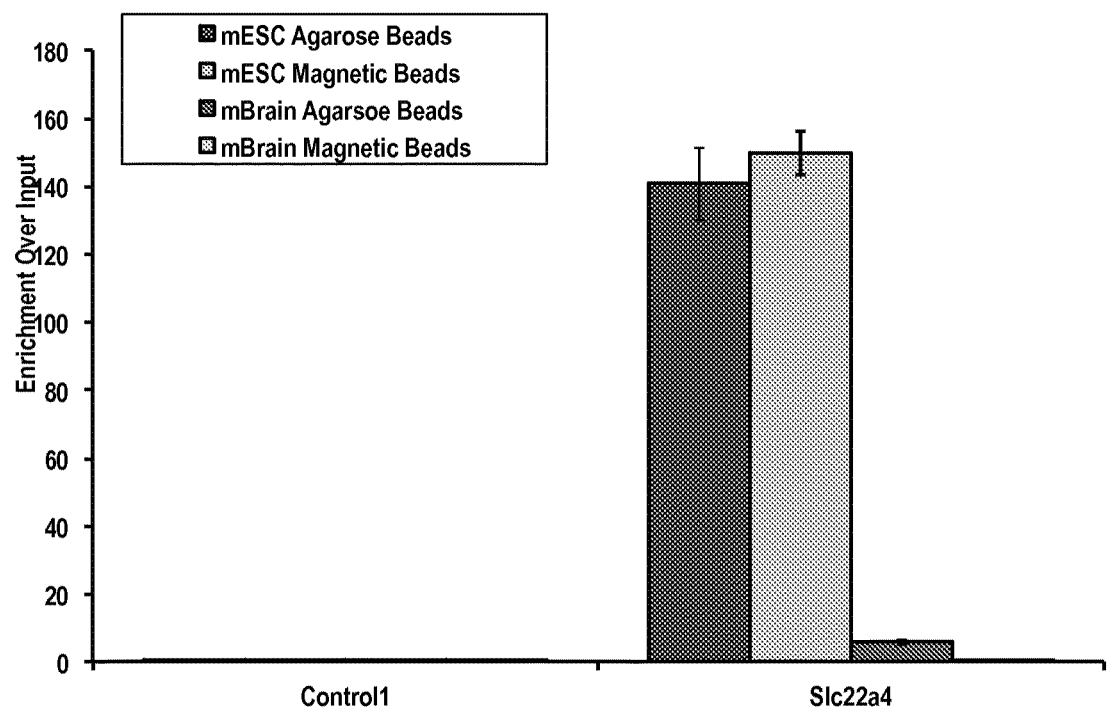
FIG. 42—shows TAM-MIRA to determine 5-hmC levels in mouse genomic DNA

Thus in this approach, Applicant incubated 100 ng of unfragmented mouse genomic DNA from brain and embryonic stem cells (ESC) with 2 ug of the primary 5-hmC antibody followed by 2 ug of the secondary antibody conjugate/transposome complex utilized in TAM-ChIP. After binding, dilution and tagmentation of the genomic DNA, the bound regions were captured using either Protein G Agarose or Magnetic beads, followed by washes and elution. The purified DNA was subjected to 25 cycles of PCR amplification using the same adapters and primers utilized in TAM-ChIP. All libraries were purified using standard methods and diluted to 2 ng/ul. Quantitative PCR was performed using primers targeting the regions known to be negative (Control 1) or positive (Slc22a4) for DNA hydroxymethylation. FIG. 42 demonstrates that the secondary antibody conjugate/transposome complex can be utilized to specifically bind and tagment only those genomic loci bound by the 5-hmc antibody. Further, the negative control region known to be depleted of 5-hMC, showed no enrichment, indicating no tagmentation by the transposase, confirming that the 5-hmC antibody was directing the secondary antibody/transposome to those DNA loci associated with hydroxymethylation.

All together the results in this Example indicate that the methodology of antibody directed tagmentation of unfragmented genomic DNA, in addition to chromatin, by the TS-Tn5 transposase can be utilized to specifically detect 5-mC and 5-hmC levels. These data also support this approach for detecting formyl and carboxylcytosine.

Those of skill in the art will recognize that many equivalent antibody/oligonucleotide conjugation strategies could be substituted for use in the invention. For example, direct via a chemical crosslinker, indirect via other proteins/biomolecules that have strong interactions, including a streptavidin-protein A fusion protein (or protein G). Protein A binds the antibody in a manner that is known not to interfere with antibody function. A single protein A/G immunoglobulin binding domain could be also used, and expressed as a fusion protein. This would then bind with biotinylated oligonucleotides. There are also biotin-binding peptides that are much smaller than the streptavidin protein. Further, as indicated herein other transposon-targeted constructs are possible including those described herein based on protein-protein interactions, RNA-protein interactions, and DNA-DNA-interactions.

REFERENCES CITED

1. Allis, et al., *Overview and Concepts*, in *Epigenetics*, Allis, et al., Eds. 2006, Cold Spring Harbor Laboratory Press: New York. p. 23-62.
2. Luger, et al., Nature, 1997. 389(6648): p. 251-60.
3. Strahl and Allis, Nature, 2000. 403(6765): p. 41-5.
4. Grewal and D. Moazed, Science, 2003. 301(5634): p. 798-802.
5. Jenuwein and Allis, Science, 2001. 293(5532): p. 1074-80.
6. Suganuma and Workman, Cell, 2008. 135(4): p. 604-7.
7. Grewal, S. I., Current Opinions in Genetics & Development, 2010. 20(2): p. 134-41.
8. Vire, et al., Nature, 2006. 439(7078): p. 871-4.
9. Jones, et al., Nature Genetics, 1998. 19(2): p. 187-91.
10. Felsenfeld, G., *A Brief History of Epigenetics*, in *Epigenetics*, Allis, et al., Eds. 2006, above, p. 15-22.
11. Braunstein, et al., Genes & Development, 1993. 7(4): p. 592-604.
12. Alberts, et al., Cell, 1998. 92(4): p. 475-87.
13. Rister and Desplan, Bioessays, 2010. 32(5): p. 381-4.
14. Active Motif, 1., *ChIP-IT Express Magnetic Chromatin immunoprecipitation Kit*. 2011, Active Motif, Carlsbad, California, USA.
15. Mizuucki and Baker, *Chemical Mechanisms for Mobilizing DNA*, in *Mobile DNA II*, Craig, et al., Eds. 2002, ASM Press: Washington, p. 12-23.
16. Goryshin and Reznikoff, Journal of Biological Chemistry, 1998. 273(13): p. 7367-74.
17. Davies, et al., Science, 2000. 289(5476): p. 77-85.
18. Goryshin, et al., PNAS USA, 1998. 95(18): p. 10716-21.

19. Goryshin, et al., Nature Biotechnology, 2000. 18(1): p. 97-100.
20. Gallagher, et al., PNAS USA, 2007. 104(3): p. 1009-14.
21. Vidal, et al., PLoS One, 2009. 4(7): p. e6232.
22. Bertram, et al., Nucleic Acids Research, 2005. 33(18): p. e153.
23. Shi, et al., Moleucular and Biochemical Parasitology, 2002. 121(1): p. 141-4.
24. Suganuma, et al., Biology of Reproduction, 2005. 73(6): p. 1157-63.
25. Steger, et al., Molecular and Cellular Biology, 2008. 28(8): p. 2825-39.
26. Dirksen and Dawson, Bioconjugate Chemistry, 2008. 19(12): p. 2543-8.
27. Fredriksson, et al., Clinical Chemistry, 2008. 54(3): p. 582-9.
28. Jarvius, et al., Molecular and Cellular Proteomics, 2007. 6(9): p. 1500-9.
29. Solulink, *Protein-Protein Conjugation Kit* Solulink Inc.: San Diego.
30. Mahnke Braam and Reznikoff, Journal of Biological Chemistry, 1998. 273(18): p. 10908-13.
31. Mahnke Braam, et al., Journal of Biological Chemistry, 1999. 274(1): p. 86-92.
32. Zhang, et al., Genome Bioi, 2008. 9(9): p. R137.
33. Zang, et al., Bioinformatics, 2009. 25(15): p. 1952-8.
34. Xu, et al., Bioinformatics, 2010. 26(9): p. 1199-204.
35. Li, et al., Genome Biology, 2010. 11(2): p. R22.
36. *Life Science Tools and Reagents: Global Markets* 2011. 2011, BCC Research, Inc., Wellesley, MAm USA.
37. *Epigenetics Market Trends* 2011. 2011, Select BioSciences, Ltd, Sudbury, UK.
38. Chu et al., Molecular Cell, 2011. 44: 667-678.
39. Simon et al., Proc. Nat. Acad. Sci. 2011. 108(51):20497-20502
40. Guttman & Rinn Nature 2012 482:339-345
41. Jones et al, BioEssays 2000. 22:124-137
42. Finn et al., Nucleic Acid Research 1996. 24(17):3357-3363.
43. Akst, The Scientist 2012 Epigenetics Armed German *E. coli.*
44. Fang et al., Nature Biotechnology 2012. 30:1232-1239
45. Bruscella, et al., 2008. J. Bacter. 190(20):6817-6828
46. Yandell, 2013. The Scientist Decoding Bacterial Methylomes

What is claimed is:

1. A collection of binding protein-transposome compositions, wherein:
   (I) compositions among the collection comprise:
      (a) a binding protein that binds a nucleic acid-associated protein or protein domain, a DNA binding site, a chromatin-associated non-coding RNA, or a target protein that binds either of these; and
      (b) a transposase:transposon complex ("transposome") comprising a transposase stably attached to a transposon cassette; wherein:
         (i) the binding protein is stably attached to the transposome; and
         (ii) the transposon cassette comprises a transposase recognition sequence required for catalysis of a DNA integration reaction, and a bar code sequence or sequences; and
   (II) wherein the collection comprises a plurality of different binding proteins and bar code sequence or sequences, and the bar code sequence or sequences uniquely identify the binding protein of the composition to which the bar code sequence or sequences are attached
   wherein the composition is comprised in a solution free of $Mg^{++}$.

2. The collection of claim 1, wherein one or more of the binding proteins bind a nucleic acid-associated protein or protein domain.

3. The collection of claim 1, wherein one or more of the binding proteins bind a DNA binding site.

4. The collection of claim 1, wherein one or more of the binding proteins bind a target protein that binds a nucleic acid-associated protein or protein domain, or a DNA binding site.

5. The collection of claim 4, wherein one or more of the binding proteins are bound to their target protein.

6. The collection of claim 5, wherein one or more of the target proteins bind a protein-binding partner, methylated DNA, non-coding RNA, or DNA binding site.

7. The collection of claim 1, wherein one or more of the binding proteins is covalently attached to the composition.

8. The collection of claim 1, wherein one or more of the compositions further comprise one or more extraction moieties.

9. The collection of claim 8, wherein one or more of the extraction moieties comprise a member of a high affinity binding pair.

10. The collection of claim 9, wherein the high affinity binding pair is selected from biotin and avidin (or streptavidin), a carbohydrate and a lectin, an effector molecule and a receptor molecule, a cofactor and an enzyme, and an enzyme inhibitor and an enzyme.

11. The collection of claim 8, wherein one or more of the extraction moieties comprise primer sites for amplification.

12. The collection of claim 9, wherein one or more of the extraction moieties comprise primer sites for amplification.

13. The collection of claim 1, 8, 9, or 12, wherein one or more of the transposon cassettes further comprise, for whole genome sequencing applications, platform-specific tags required for next generation sequencing (NGS).

14. The collection of claim 1, wherein a plurality of the target proteins comprise a binding domain selected from the group consisting of bZIP domain, DNA binding domain, helix-loop-helix, helix-turn-helix, MG-box, leucine zipper, lexitropsin, nucleic acid simulations, zinc finger, histone methylases, recruitment proteins, Swi6 and chromodomain.

15. The collection of claim 1, comprising one or more nucleic acid-associated proteins or protein domains, wherein one or more of the nucleic acid-associated proteins or protein domains are directly or indirectly bound to chromatin.

16. A binding protein-transposome composition, comprising:
   (a) a binding protein that binds a nucleic acid-associated protein or protein domain; and
   (b) a transposase:transposon complex ("transposome") comprising a transposase stably attached to a transposon cassette; wherein:
      (i) the binding protein is stably attached to the transposome; and
      (ii) the transposon cassette comprises a transposase recognition sequence required for catalysis of a DNA integration reaction, and one or more extraction moieties
   wherein the composition is comprised in a solution free of $Mg^{++}$.

17. The composition of claim 16, wherein one or more of the extraction moieties comprise primer sites for amplification.

18. The composition of claim 16, wherein one or more of the extraction moieties comprise a member of a high affinity binding pair.

19. The composition of claim 18, wherein the high affinity binding pair is selected from biotin and avidin (or streptavidin), a carbohydrate and a lectin, an effector molecule and a receptor molecule, a cofactor and an enzyme, and an enzyme inhibitor and an enzyme.

20. The composition of claim 17, wherein one or more of the extraction moieties comprise a member of a high affinity binding pair.

21. The composition of claim 16, 17 or 18, wherein the transposon cassette further comprises platform-specific tags required for next generation sequencing (NGS).

22. The composition of claim 16, 17, or 18, wherein the transposon cassette further comprises one or more bar code sequences that uniquely identify the attached binding protein.

23. The composition of claim 21, wherein the transposon cassette further comprises one or more bar code sequences that uniquely identify the attached binding protein.

24. The composition of claim 16, wherein the binding protein comprises an antibody.

25. The composition of claim 16, wherein the binding protein comprises a non-antibody protein.

26. The composition of claim 16, wherein the binding protein is covalently attached to the composition.

27. The composition of claim 16, wherein the composition is directly or indirectly bound to chromatin.

28. The composition of claim 27, wherein the binding protein is bound to a nucleic acid-associated protein or protein domain in the chromatin.

29. The composition of claim 27, wherein the binding protein is bound to a target protein that is bound to a nucleic acid-associated protein or protein domain further bound to chromatin.

30. A binding protein-transposome composition, comprising:
   (a) a binding protein that binds a target protein, wherein the target protein binds a nucleic acid-associated protein or protein domain, a chromatin-associated non-coding RNA, or a DNA binding site; and
   (b) a transposase:transposon complex ("transposome") comprising a transposase stably attached to a transposon cassette; wherein:
      (i) the binding protein is stably attached to the transposome; and
      (ii) the transposon cassette comprises a transposase recognition sequence required for catalysis of a DNA integration reaction, and one or more extraction moieties
   wherein the composition is comprised in a solution free of $Mg^{++}$.

31. The composition of claim 30, wherein the binding protein comprises an antibody.

32. The composition of claim 30, wherein the binding protein comprises a non-antibody protein.

33. The composition of claim 32, wherein the binding protein comprises Protein A, Protein G, a Protein A fusion protein or a Protein G fusion protein.

34. The composition of claim 30, wherein the binding protein is covalently attached to the composition.

35. The composition of claim 30, wherein target protein binds a nucleic acid-associated protein or protein domain.

36. The composition of claim 30, wherein target protein binds a DNA binding site.

37. The composition of claim 30, wherein the target protein binds a protein-binding partner, methylated DNA, non-coding RNA, or a DNA binding site.

38. The composition of claim 30, wherein the target protein comprises a binding domain selected from the group consisting of bZIP domain, DNA binding domain, helix-loop-helix, helix-turn-helix, MG-box, leucine zipper, lexitropsin, nucleic acid simulations, zinc finger, histone methylases, recruitment proteins, Swi6 and chromodomain.

39. The composition of claim 30, wherein one or more of the extraction moieties comprises primer sites for amplification.

40. The composition of claim 39, wherein one or more of the extraction moieties comprises a member of a high affinity binding pair.

41. The composition of claim 30, wherein one or more of the extraction moieties comprises a member of a high affinity binding pair.

42. The composition of claim 41, wherein the high affinity binding pair is selected from biotin and avidin (or streptavidin), a carbohydrate and a lectin, an effector molecule and a receptor molecule, a cofactor and an enzyme, and an enzyme inhibitor and an enzyme.

43. The composition of claim 30, 39, 40, or 41, wherein the transposon cassette further comprises one or more bar code sequences that uniquely identify the attached binding protein.

44. The composition of claim 30, 39, 40, or 41, wherein the transposon cassette further comprises, for whole genome sequencing applications, platform-specific tags required for next generation sequencing (NGS).

45. The composition of claim 43, wherein the transposon cassette further comprises, for whole genome sequencing applications, platform-specific tags required for next generation sequencing (NGS).

46. The composition of any of claims 30, 35, 36, and 37, wherein the binding protein is further bound to the target protein.

47. The composition of claim 46, wherein the target protein comprises an antibody.

48. The composition of claim 30, wherein the composition is further bound to chromatin.

* * * * *

SEQUENCE LISTING

```
<160> NUMBER OF SEQ ID NOS: 8

<210> SEQ ID NO 1
<211> LENGTH: 47
<212> TYPE: DNA
<213> ORGANISM: artificial
<220> FEATURE:
<223> OTHER INFORMATION: Adapter 1a

<400> SEQUENCE: 1
aatgatacgg cgaccaccga gatcttaagg cgatcgtcgg cagcgtc            47

<210> SEQ ID NO 2
<211> LENGTH: 45
<212> TYPE: DNA
<213> ORGANISM: Artificial
<220> FEATURE:
<223> OTHER INFORMATION: Adapter 2A

<400> SEQUENCE: 2
caagcagaag acggcatacg agatcggtct gtctcgtggg ctcgg              45

<210> SEQ ID NO 3
<211> LENGTH: 43
<212> TYPE: DNA
<213> ORGANISM: Artificial
<220> FEATURE:
<223> OTHER INFORMATION: Adapter 1b

<400> SEQUENCE: 3
aatgatacgg cgaccaccga gatctacact cgtcggcagc gtc                43

<210> SEQ ID NO 4
<211> LENGTH: 44
<212> TYPE: DNA
<213> ORGANISM: Artificial
<220> FEATURE:
<223> OTHER INFORMATION: Adapter 2b

<400> SEQUENCE: 4
caagcagaag acggcatacg atagatcgcg tctcgtgggc tcgg               44
```

```
<210> SEQ ID NO 5
<211> LENGTH: 20
<212> TYPE: DNA
<213> ORGANISM: Artificial
<220> FEATURE:
<223> OTHER INFORMATION: Primer 1

<400> SEQUENCE: 5
aatgatacgg cgaccaccga                                          20

<210> SEQ ID NO 6
<211> LENGTH: 21
<212> TYPE: DNA
<213> ORGANISM: Artificial
<220> FEATURE:
<223> OTHER INFORMATION: Primer 2

<400> SEQUENCE: 6
caagcagaag acggcatacg a                                        21

<210> SEQ ID NO 7
<211> LENGTH: 33
<212> TYPE: DNA
<213> ORGANISM: Artificial
<220> FEATURE:
<223> OTHER INFORMATION: Oligonucleotide A

<400> SEQUENCE: 7
tcgtcggcag cgtcagatgt gtataagaga cag                           33

<210> SEQ ID NO 8
<211> LENGTH: 34
<212> TYPE: DNA
<213> ORGANISM: Artificial
<220> FEATURE:
<223> OTHER INFORMATION: Oligonucleotide B

<400> SEQUENCE: 8
gtctcgtggg ctcggagatg tgtataagag acag                          34
```